United States Patent
Boggs, II et al.

(10) Patent No.: US 9,895,530 B2
(45) Date of Patent: Feb. 20, 2018

(54) SYSTEMS AND METHODS TO PLACE ONE OR MORE LEADS IN TISSUE TO ELECTRICALLY STIMULATE NERVES OF PASSAGE TO TREAT PAIN

(75) Inventors: Joseph W. Boggs, II, Chapel Hill, NC (US); Rosemary H. Zang, Avon Lake, OH (US)

(73) Assignee: SPR THERAPEUTICS, INC., Cleveland, OH (US)

( * ) Notice: Subject to any disclaimer, the term of this patent is extended or adjusted under 35 U.S.C. 154(b) by 0 days.

(21) Appl. No.: 13/605,653

(22) Filed: Sep. 6, 2012

(65) Prior Publication Data

US 2013/0238066 A1 Sep. 12, 2013

Related U.S. Application Data

(63) Continuation-in-part of application No. 12/653,023, filed on Dec. 7, 2009, now Pat. No. 8,954,153, which
(Continued)

(51) Int. Cl.
*A61N 1/05* (2006.01)
*A61N 1/04* (2006.01)
(Continued)

(52) U.S. Cl.
CPC ......... *A61N 1/0551* (2013.01); *A61N 1/0456* (2013.01); *A61N 1/0502* (2013.01);
(Continued)

(58) Field of Classification Search
CPC .. A61N 1/0551; A61N 1/0558; A61N 1/0502; A61N 1/36021; A61N 1/36017;
(Continued)

(56) References Cited

U.S. PATENT DOCUMENTS

| 5,330,515 A | 7/1994 | Rutecki et al. |
| 6,600,954 B2 * | 7/2003 | Cohen ................ A61N 1/36071 607/46 |

(Continued)

FOREIGN PATENT DOCUMENTS

| WO | 2010/014260 A1 | 2/2010 |
| WO | 2012/075497 | 6/2012 |

(Continued)

OTHER PUBLICATIONS

International Search Report for PCT/US12/53952 dated Nov. 15, 2012.
(Continued)

*Primary Examiner* — Alyssa M Alter
(74) *Attorney, Agent, or Firm* — McDonald Hopkins LLC

(57) ABSTRACT

Systems and methods are provided for applying electrical stimulation to a body by an electrode spaced from a target nerve of passage. It has been discovered that pain felt, or perceived to be felt, in a given region of the body can be treated by stimulating muscle close to a "nerve of passage" in a region that is superior (i.e., cranial or upstream toward the spinal column) to the region where pain is felt, such as in a case of post-amputation residual limb pain, or purportedly felt in the case of post-amputation phantom limb pain.

32 Claims, 26 Drawing Sheets

Related U.S. Application Data is a continuation-in-part of application No. 12/653,029, filed on Dec. 7, 2009, now abandoned, which is a continuation-in-part of application No. 13/294,875, filed on Nov. 11, 2011.

(60) Provisional application No. 61/531,462, filed on Sep. 6, 2011, provisional application No. 61/201,030, filed on Dec. 5, 2008, provisional application No. 61/412,685, filed on Nov. 11, 2010.

(51) Int. Cl.
    *A61N 1/36* (2006.01)
    *A61B 5/06* (2006.01)

(52) U.S. Cl.
    CPC ....... *A61N 1/0558* (2013.01); *A61N 1/36021* (2013.01); *A61N 1/36071* (2013.01); *A61B 5/061* (2013.01); *A61N 1/36017* (2013.01)

(58) Field of Classification Search
    CPC ... A61N 1/36071; A61N 1/0456; A61B 5/061
    USPC .................................................. 607/117, 118
    See application file for complete search history.

(56) References Cited

U.S. PATENT DOCUMENTS

| | | |
|---|---|---|
| 7,337,005 B2 | 2/2008 | Kim et al. |
| 7,369,894 B2 | 5/2008 | Gerber |
| 7,761,166 B2 | 7/2010 | Giftakis et al. |
| 7,792,591 B2 | 9/2010 | Rooney et al. |
| 2002/0099419 A1 | 7/2002 | Cohen et al. |
| 2003/0100933 A1* | 5/2003 | Ayal .................. A61N 1/36003 607/48 |
| 2005/0149154 A1* | 7/2005 | Cohen ................. A61N 1/0551 607/118 |
| 2005/0246006 A1 | 11/2005 | Daniels |
| 2006/0206166 A1 | 9/2006 | Weiner |
| 2008/0132982 A1 | 6/2008 | Gerber |
| 2009/0192567 A1 | 7/2009 | Armstrong et al. |
| 2010/0036454 A1 | 2/2010 | Bennett et al. |
| 2010/0152808 A1 | 6/2010 | Boggs, II |
| 2011/0022114 A1 | 1/2011 | Navarro |
| 2011/0054565 A1 | 3/2011 | Wacnik et al. |
| 2011/0106207 A1 | 5/2011 | Cauller et al. |

FOREIGN PATENT DOCUMENTS

| | | |
|---|---|---|
| WO | WO2013036630 | 3/2013 |
| WO | WO2014/099423 | 6/2014 |

OTHER PUBLICATIONS

International Search Report and the Written Opinion of the International Searching Authority, PCT/US2013/73647, SPR Therapeutics, LLC, Feb. 20, 2014.

International Search Report and the Written Opinion of the International Searching Authority, PCT/US2012/53952, SPR Therapeutics, LLC, Nov. 15, 2012.

Extended European Search Report for Application EP13866258.0 PCT/US2013073647, dated Sep. 5, 2016, European Patent Office, Germany.

\* cited by examiner

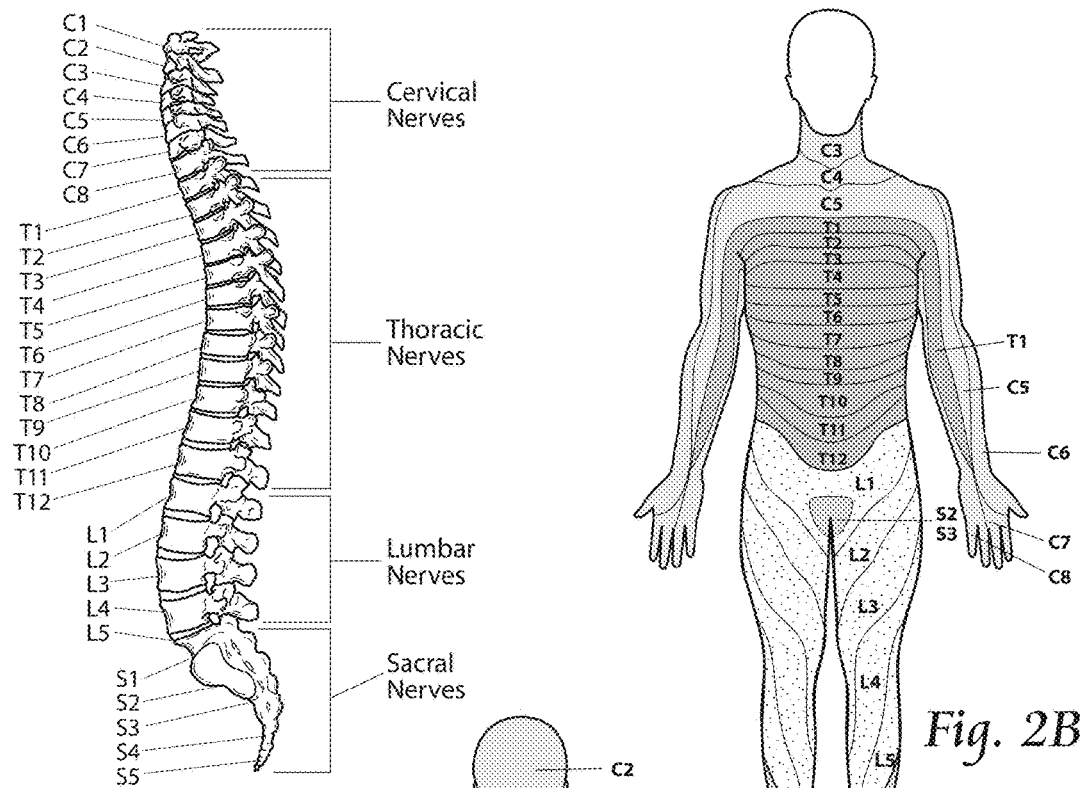
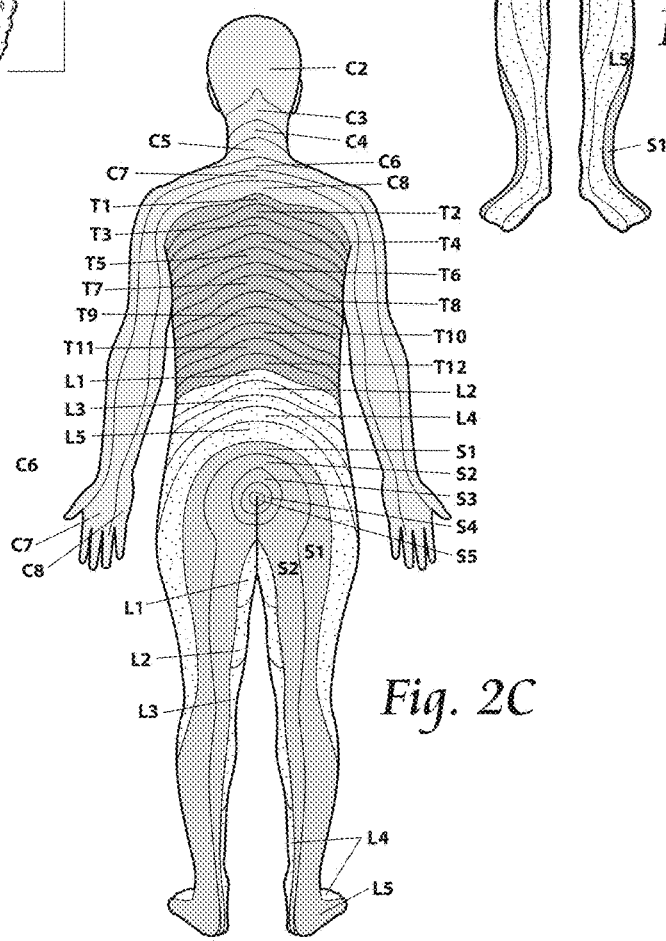
Fig. 2A
Fig. 2B
Fig. 2C

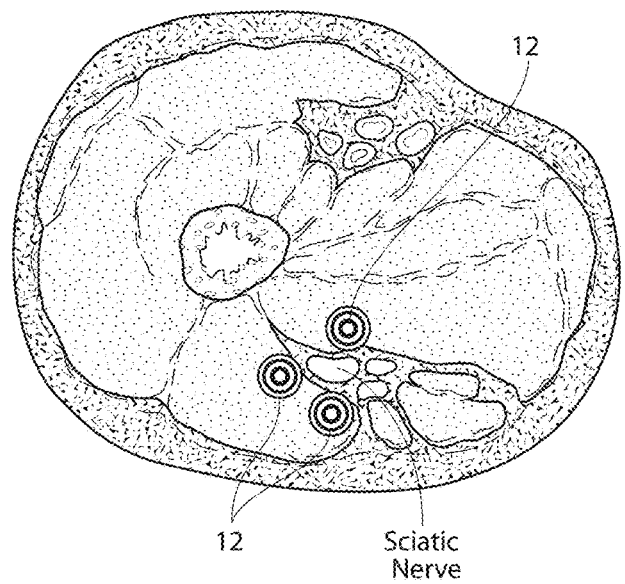
*Fig. 19A*
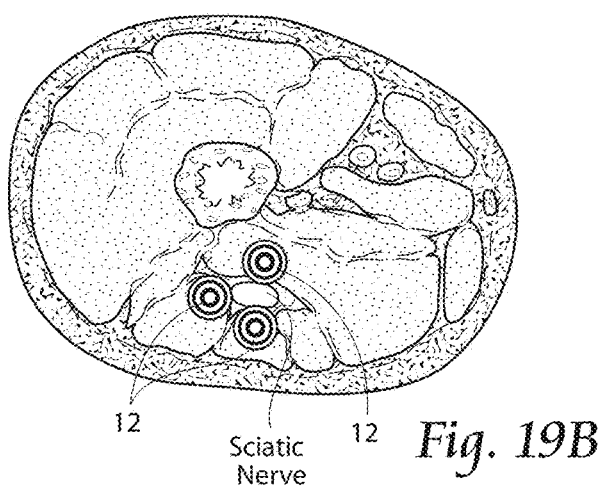
*Fig. 19B*
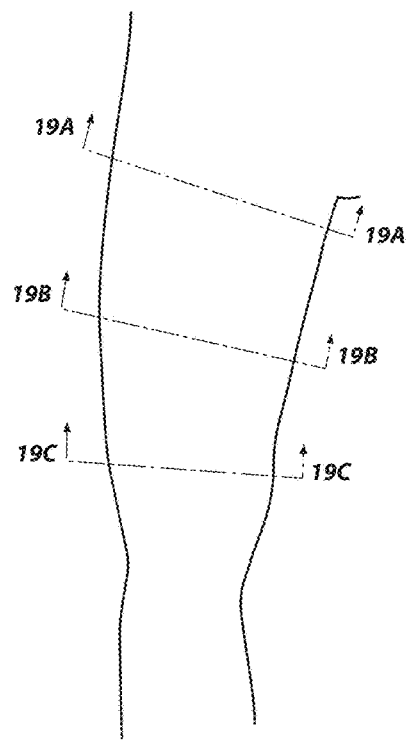
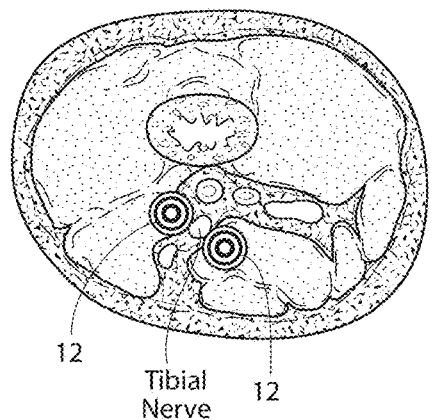
*Fig. 19C*

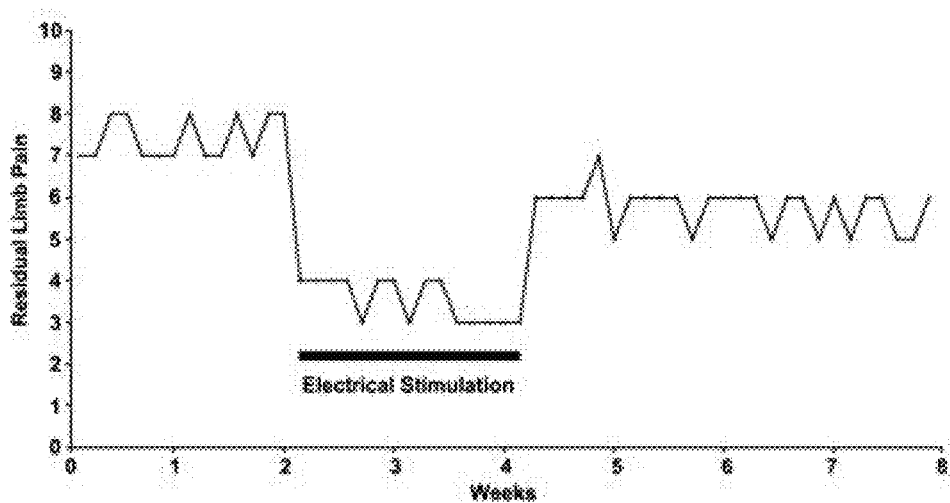

Fig. 25

| | Baseline | Stimulation Trial | | 1 Wk F/U | 4 Wk F/U |
|---|---|---|---|---|---|
| | Stim Off | Stim On | Stim On | Stim Off | Stim Off |
| | Wk 0 | Wk 3 | Wk 4 | Wk 5 | Wk 8 |
| Brief Pain Inventory Short Form (BPI-SF) | | | | | |
| BPI3- Worst pain in last week | 8 | 4 (50%) | 3 (63%) | 7 (13%) | 6 (25%) |
| BPI9- Sum of pain interference scores | 44 | 12 (71%) | 0 (100%) | 10 (76%) | 13 (69%) |
| Pain Disability Index (PDI)- sum of scores | 66 | 23 (45%) | 11 (74%) | 11 (74%) | 20 (52%) |
| BDI-II Beck Depression Inventory sum of scores | 0 | 1 (3%) | 0 (0%) | 1 (3%) | 1 (3%) |
| PGIC- Patient Global Impression of Change | n/a | Much Improved | Very Much Improved | Much Improved | Minimally Improved |

Fig. 26

SYSTEMS AND METHODS TO PLACE ONE OR MORE LEADS IN TISSUE TO ELECTRICALLY STIMULATE NERVES OF PASSAGE TO TREAT PAIN

RELATED APPLICATIONS

This application claims the benefit of U.S. Provisional Patent Application Ser. No. 61/531,462, filed 6 Sep. 2011, and entitled "Systems and Methods to Place One or More Leads in Tissue to Electrically Stimulate Nerves of Passage to Treat Pain." This application is also a continuation in part of co-pending U.S. patent application Ser. No. 12/653,023, filed 7 Dec. 2009, granted on Feb. 10, 2015 as U.S. Pat. No. 8,954,153, and entitled "Systems and Methods To Place One or More Leads in Tissue to Electrically Stimulate Nerves of Passage to Treat Pain," which is incorporated by reference in its entirety and which claims the benefit of U.S. Provisional Patent Application Ser. No. 61/201,030, filed 5 Dec. 2008, and entitled "Systems and Methods to Place One or More Leads in Tissue for Providing Functional and/or Therapeutic Stimulation."

This application is also a continuation-in-part of co-pending U.S. patent application Ser. No. 12/653,029, filed 7 Dec. 2009, and entitled "Systems and Methods To Place One or More Leads in Tissue for Providing Functional and/or Therapeutic Stimulation," which is incorporated by reference in its entirety and which claims the benefit of U.S. Provisional Patent Application Ser. No. 61/201,030, filed 5 Dec. 2008, and entitled "Systems and Methods to Place One or More Leads in Tissue for Providing Functional and/or Therapeutic Stimulation."

This application is also a continuation-in-part of co-pending U.S. patent application Ser. No. 13/294,875, filed 11 Nov. 2011, and entitled "Systems and Methods to Place One or More Leads in Tissue to Electrically Stimulate Nerves to Treat Pain," which is incorporated by reference in its entirety and which claims the benefit of U.S. Provisional Patent Application Ser. No. 61/412,685, filed 11 Nov. 2010, and entitled "Systems and Methods to Place One or More Leads in Tissue to Electrically Stimulate Nerves to Treat Pain."

STATEMENT REGARDING FEDERALLY SPONSORED RESEARCH

This invention was made with government support under grant no. R43NS066523 awarded by the National Institute of Health through the National Institute of Neurological Disorders and Stroke. The Government has certain rights in the invention.

FIELD OF INVENTION

This invention relates to systems and methods for placing one or more leads in tissue to electrically stimulate nerves to treat pain.

BACKGROUND OF THE INVENTION

The electrical stimulation of nerves, often afferent nerves, to indirectly affect the stability or performance of a physiological system can provide functional and/or therapeutic outcomes, and has been used for activating target nerves to provide therapeutic relief of pain.

While existing systems and methods can provide remarkable benefits to individuals requiring therapeutic relief, many issues and the need for improvements still remain.

Many techniques, such as non-narcotic analgesics described below, have been developed to treat pain, but all of them are ultimately insufficient.

Psychological strategies, such as biofeedback and psychotherapy, may be used as an adjunct to other therapies but are seldom sufficient, and there are few studies demonstrating efficacy.

Electrical stimulation systems have been used for the relief of pain, but widespread use of available systems is limited.

There exist both external and implantable devices for providing electrical stimulation to activate nerves and/or muscles to provide therapeutic relief of pain. These "neurostimulators" are able to provide treatment and/or therapy to individual portions of the body. The operation of these devices typically includes the use of an electrode placed either on the external surface of the skin and/or a surgically implanted electrode. In most cases, surface electrode(s), cuff-style electrode(s), paddle-style electrode(s), spinal column electrodes, and/or percutaneous lead(s) having one or more electrodes may be used to deliver electrical stimulation to the select portion of the patient's body.

One example of an indication where therapeutic treatment may be provided is for the treatment of pain, such as to provide a therapy to reduce pain in individuals with amputated limbs. Amputation leads to chronic pain in almost all (95%) patients, regardless of how much time had passed since the amputation. The pain can be extremely bothersome to amputees, significantly decrease their quality of life, correlate with increased risk of depression, and negatively affect their inter-personal relationships and their ability to return to work. The present methods of treatment, which are primarily medications, are unsatisfactory in reducing amputation-related pain, have unwanted side effects, offer a low success rate, and often lead to addiction.

Most amputees have two types of pain: residual limb (stump) pain and phantom pain. Approximately 72-85% of amputees have phantom pain and 68-76% of amputees have residual limb (stump) pain. Both stump pain and phantom limb pain are chronic pains experienced after an amputation, and they are easily distinguished by the perceived location of the pain. Stump pain is sensed in the portion of the limb that remains after amputation, and phantom limb pain is perceived in the portion of the limb that has been removed. Typically, amputee patients with severe stump pain also have severe phantom limb pain, but it is recommended that their responses to treatment be measured independently. Stump and phantom pain can be severe and debilitating to a large proportion of persons with amputations, who will unfortunately often progress through a battery of management techniques and procedures without finding relief from their pain.

It has been estimated that 80-95% of 1.7 million persons who currently live with amputations, plus the additional 185,000 persons expected to undergo amputation each year in the United States, suffer or will suffer from stump and/or phantom pain at an annual direct cost of $1.4-2.7 billion and overall associated costs of $13 billion. Severe post-amputation pain often leads to further disability, reduced quality of life, and frequently interferes with the simple activities of daily life more than the amputation itself, and no available therapy is sufficient to manage it.

Many techniques have been developed to treat post-amputation pain, but all of them are ultimately insufficient. One review indicated that none of the then 68 treatments available for post-amputation pain were uniformly successful, and later reviews have found that little has changed;

there remains a large need for an effective method of treating stump and phantom pain. Some studies report that as few as 1% of amputees with severe phantom and stump pain receive lasting benefit from any of the available treatments. Presently, most patients are managed with medications, but approximately a third of amputees still report severe (intensity of 7-10 on a scale of 0-10) phantom and stump pain.

Non-narcotic analgesics, such as acetaminophen or non-steroidal anti-inflammatory drugs (NSAIDS), have relatively minor side effects and are commonly used for several types of pain. However, they are general, non-targeted attempts that are rarely sufficient in managing moderate to severe chronic post-amputation pain.

The use of narcotic analgesics, such as N-methyl-D-aspartate (NDMA) antagonists, has shown only minor success with inconsistent results. Narcotics carry the risk of addiction and side effects, such as nausea, confusion, vomiting, hallucinations, drowsiness, dizziness, headache, agitation, and insomnia. Several trials of multiple narcotic agents have failed to show statistically significant improvement in phantom pain.

Physical methods, such as adjusting a prosthesis, may be helpful to reduce post-amputation pain, but generally only if such pain is due to poor prosthetic fit. Other physical treatments, including acupuncture, massage, and percussion or heating/cooling of the stump, have few complications but also have limited data to support their use and have not been well accepted clinically.

Psychological strategies, such as biofeedback and psychotherapy, may be used as an adjunct to other therapies but are seldom sufficient, and there are few studies demonstrating efficacy and these approaches are not specific to stump or phantom pain. Mirror-box therapy has demonstrated mixed results and is not widely used in clinical practice.

Many surgical procedures have been attempted, but few are successful and most are contraindicated for the majority of the amputee patients. Because neuromas may be implicated with stump and phantom pain, there have been many attempts to remove them surgically, but ultimately a new neuroma usually develops each time a nerve is cut and the pain relief only lasts for the time that it takes for a new neuroma to form, usually about three weeks. Furthermore, neuroablative procedures carry the risk of producing deafferentation pain, and any surgical procedure has a greater chance of failure than success.

Thus, present medical treatments of stump and phantom pain are inadequate, and most sufferers resort to living with pain that is poorly controlled with medications.

Electrical stimulation systems hold promise for relief of post-amputation pain, but widespread use of available systems is limited.

Transcutaneous electrical nerve stimulation (TENS) has been cleared by the FDA for treatment of pain. TENS systems are external neurostimulation devices that use electrodes placed on the skin surface to activate target nerves below the skin surface. TENS has a low rate of serious complications, but it also has a relatively low (i.e., less than 25%) long-term rate of success.

Application of TENS has been used to treat pain successfully, but it has low long-term patient compliance, because it may cause additional discomfort by generating cutaneous pain signals due to the electrical stimulation being applied through the skin, and the overall system is bulky, cumbersome, and not suited for long-term use.

In addition, several clinical and technical issues associated with surface electrical stimulation have prevented it from becoming a widely accepted treatment method. First, stimulation of cutaneous pain receptors cannot be avoided resulting in stimulation-induced pain that limits patient tolerance and compliance. Second, electrical stimulation is delivered at a relatively high frequency to prevent stimulation-induced pain, which leads to early onset of muscle fatigue in turn preventing patients from properly using their arm. Third, it is difficult to stimulate deep nerves and/or muscles with surface electrodes without stimulating overlying, more superficial nerves and/or muscles resulting in unwanted stimulation. Finally, clinical skill and intensive patient training is required to place surface electrodes reliably on a daily basis and adjust stimulation parameters to provide optimal treatment. The required daily maintenance and adjustment of a surface electrical stimulation system is a major burden on both patient and caregiver.

Spinal cord stimulation (SCS) systems are FDA approved as implantable neurostimulation devices marketed in the United States for treatment of pain. Similar to TENS, when SCS evokes paresthesias that cover the region of pain, it confirms that the location of the electrode and the stimulus intensity should be sufficient to provide pain relief and pain relief can be excellent initially, but maintaining sufficient paresthesia coverage is often a problem as the lead migrates along the spinal canal.

Spinal cord stimulation is limited by the invasive procedure and the decrease in efficacy as the lead migrates. When it can produce paresthesias in the region of pain, spinal cord stimulation is typically successful initially in reducing pain, but over time the paresthesia coverage and pain reduction is often lost as the lead migrates away from its target.

Lead migration is the most common complication for spinal cord stimulators occurring in up to 45-88% of the cases. When the lead migrates, the active contact moves farther from the target fibers and loses the ability to generate paresthesias in the target area. SCS systems attempt to address this problem by using leads with multiple contacts so that as the lead travels, the next contact in line can be selected to be the active contact.

Peripheral nerve stimulation may be effective in reducing pain, but it previously required specialized surgeons to place cuff- or paddle-style leads around the nerves in a time consuming procedure.

Immediately following an amputation, all patients experience short-term (postoperative) pain, but it usually resolves within a month as the wound heals. In contrast, a long-term pain often develops and persists in the residual limb, and may be perceived in the phantom limb, after the amputated limb has healed. Residual limb pain and phantom limb pain are thought to have a peripheral and central component, and both components may be mediated by stimulating the peripheral nerves that were transected during amputation.

Neuromas develop when a peripheral nerve is cut and the proximal portion produces new axon growth that forms a tangled mass as it fails to connect with the missing distal portion of the nerve. All amputations produce neuromas and not all neuromas are painful, but neuromas are thought to be a major source of pain after amputation. Neuromas may generate spontaneous activity, and the level of activity in afferent fibers innervating the region of pain has been linked to the level of post-amputation pain.

As previously described, electrical stimulation has been used and shown to be effective in treating amputee pain, but present methods of implementation have practical limitations that prevent widespread use. External systems are too cumbersome, and implanted spinal cord stimulation systems often have problems of lead migration along the spinal canal, resulting in either the need for frequent reprogramming or clinical failure.

Percutaneous, intramuscular electrical stimulation for the treatment of post-stroke shoulder pain has been studied as an alternative to surface electrical stimulation. A feasibility study and a pilot study showed significant reduction in pain and no significant adverse events when using percutaneous, intramuscular electrical stimulation in shoulder muscles.

This form of percutaneous, intramuscular electrical stimulation can be characterized as "motor point" stimulation of muscle. To relieve pain in the target muscle, the percutaneous lead is placed in the muscle that is experiencing the pain near the point where a motor nerve enters the muscle (i.e., the motor point). In "motor point" stimulation of muscle, the muscle experiencing pain is the same muscle in which the lead is placed. In "motor point" stimulation of muscle, the pain is felt and relieved in the area where the lead is located.

SUMMARY OF THE INVENTION

The invention provides systems and methods for placing one or more leads in tissue for providing electrical stimulation to tissue to treat pain in a manner unlike prior systems and methods. Systems and methods according to the present invention may be utilized to reduce pain, such as that experienced by amputees. Most amputees have two types of pain: residual limb (stump) pain and phantom pain. The systems and methods of the present invention are adapted to reduce either and/or both types of pain by stimulating target nerves of passage. It is to be appreciated that amputation may include any or all portions of a limb, including any arm or leg in both humans and animals.

The invention provides systems and methods incorporate a discovery that pain felt in a given region of the body can be treated, not by motor point stimulation of muscle in the local region where pain is felt, but by stimulating muscle close to a "nerve of passage" in a region that is superior (i.e., cranial or upstream toward the spinal column) to the region where pain is felt. Neural impulses comprising pain felt in a given muscle or cutaneous region of the body pass through spinal nerves that arise from one or more nerve plexuses. The spinal nerves in a nerve plexus, which comprise trunks that divide by divisions and/or cords into branches, comprise "nerves of passage." It has been discovered that applying stimulation in a muscle or other tissue (including adipose or connective tissue) near a targeted nerve of passage relieves pain that manifests itself in a region that is inferior (i.e., caudal or downstream from the spinal column) from where stimulation is actually applied.

Phantom limb pain (one type of post-amputation pain) is one example of the effectiveness of "nerves of passage" stimulation, because the area from which phantom pain is perceived as emanating does not physically exist. A lead cannot be physically placed in the region(s) (e.g. muscles and/or other tissues and/or structures including adipose tissue, bones, joints, ligaments, connective tissue) that hurt, because those regions (e.g. muscles and/or other tissues) were amputated. Still, by applying stimulation in a region (e.g. a muscle and/or other tissue including adipose) that has not been amputated near a targeted nerve of passage that, before amputation, natively innervated the amputated region(s), phantom limb pain can be treated.

Chronic or acute pain in existing, non-amputated muscles can also be treated by "nerves of passage" stimulation. By applying stimulation in an existing muscle near a targeted nerve of passage that caudally innervates the region where chronic or acute pain is manifested, the pain can be treated.

In "nerves of passage" stimulation, an electrode, which may be supported on a wire lead, can be placed in a muscle or other tissue that is conveniently located near a nerve trunk that passes by the lead on the way to the painful area. On "nerves of passage" stimulation, the lead is placed in a muscle that is not the target (painful) muscle, but rather a muscle that is upstream from the painful region, because the proximal muscle presents a convenient and useful location to place the lead or electrode.

The systems and methods make possible the treatment of pain (e.g. acute, sub-acute or sub-chronic, and/or chronic) in which cases muscle contraction cannot be evoked or is otherwise undesirable (e.g. in the case of amputation pain in which the target area has been amputated is no longer physically present), or other cases of nerve damage either due to a degenerative diseases or condition such as diabetes of impaired vascular function (in which the nerves are slowly degenerating, progressing from the periphery), or due to other disorders, trauma, surgery or other reasons it may be undesirable or is contra-indicated to place an electrode or lead in or near that region(s) of pain. The systems and methods make possible the placement stimulation leads in regions distant from the motor point or region of pain, e.g., where easier access or more reliable access or a clinician-preferred access be accomplished; or in situations where the motor nerve point is not available, damaged, traumatized, or otherwise not desirable; or in situations where it is desirable to stimulate more than one motor point with a single lead; or for cosmetic reasons; or to shorten the distance between the lead and its connection with a pulse generator; or to avoid tunneling over a large area. Additionally, where only a single electrode is utilized, risks of complications and number of system components may be minimized.

Other types of pain may also be treated according to the present invention, including without limitation neuropathic pain, post-surgical pain (e.g. pain following knee surgery or total knee arthroplasty (TKA)), joint pain, complex regional pain syndrome (CRPS), and neuropathies (such as diabetic neuropathy).

Other features and advantages of the inventions are set forth in the following specification and attached drawings.

BRIEF DESCRIPTION OF THE DRAWINGS

FIG. 2A is a schematic anatomic view of a human spine, showing the various regions and the vertebrae comprising the regions.

FIGS. 2B and 2C are schematic anatomic views of the dermatome boundaries of a human.

FIGS. 19A, 19B, and 19C are schematic sectional anatomic views of a system for applying nerve of passage stimulation along a sciatic/tibial nerve.

FIG. 25 is a graph of daily-reported worst pain felt over previous twenty-four hours as reported over an eight-week period, including a two-week initial baseline period, a two-week stimulation period, and a four-week follow-up period FIG. 26 is a table indicating outcome measures collected during baseline (Visit 1), after the first week of stimulation (Visit 3), after the second week of stimulation (Visit 4), after the first week of follow-up (F/U) (Visit 5), and after the fourth week of follow-up (Visit 6). Percent change from baseline is reported in parentheses (%) where applicable.

DESCRIPTION OF THE PREFERRED EMBODIMENTS

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

Any elements described herein as singular can be pluralized (i.e., anything described as "one" can be more than one). Any species element of a genus element can have the characteristics or elements of any other species element of that genus. The described configurations, elements or complete assemblies and methods and their elements for carrying out the invention, and variations of aspects of the invention can be combined and modified with each other in any combination.

I. The Peripheral Nervous System (Anatomic Overview)

Figure 1A:
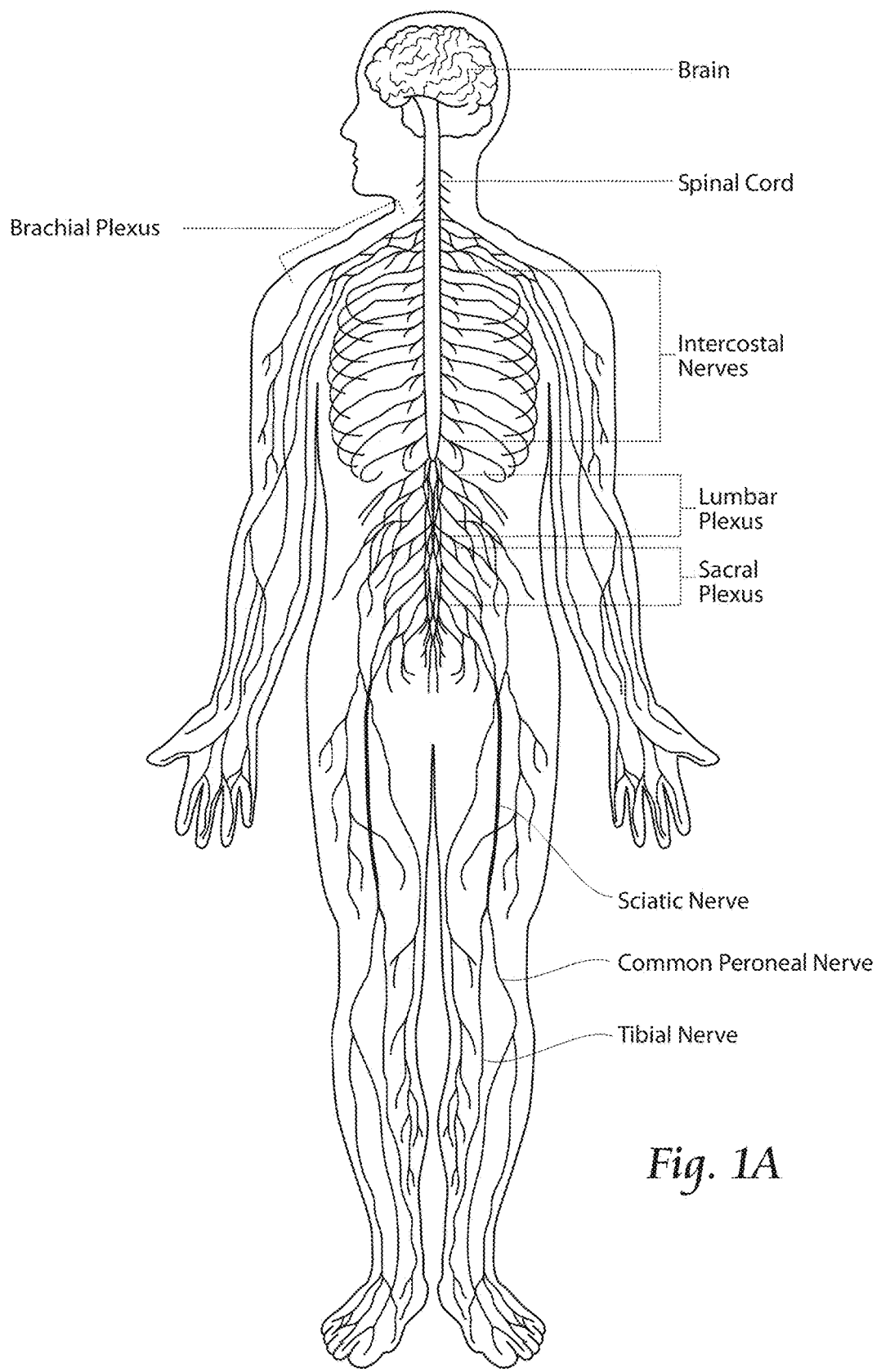
FIGS. 1A and 1B are schematic anatomic views, respectively anterior and lateral, of a human peripheral nervous system.
Figure 1B:
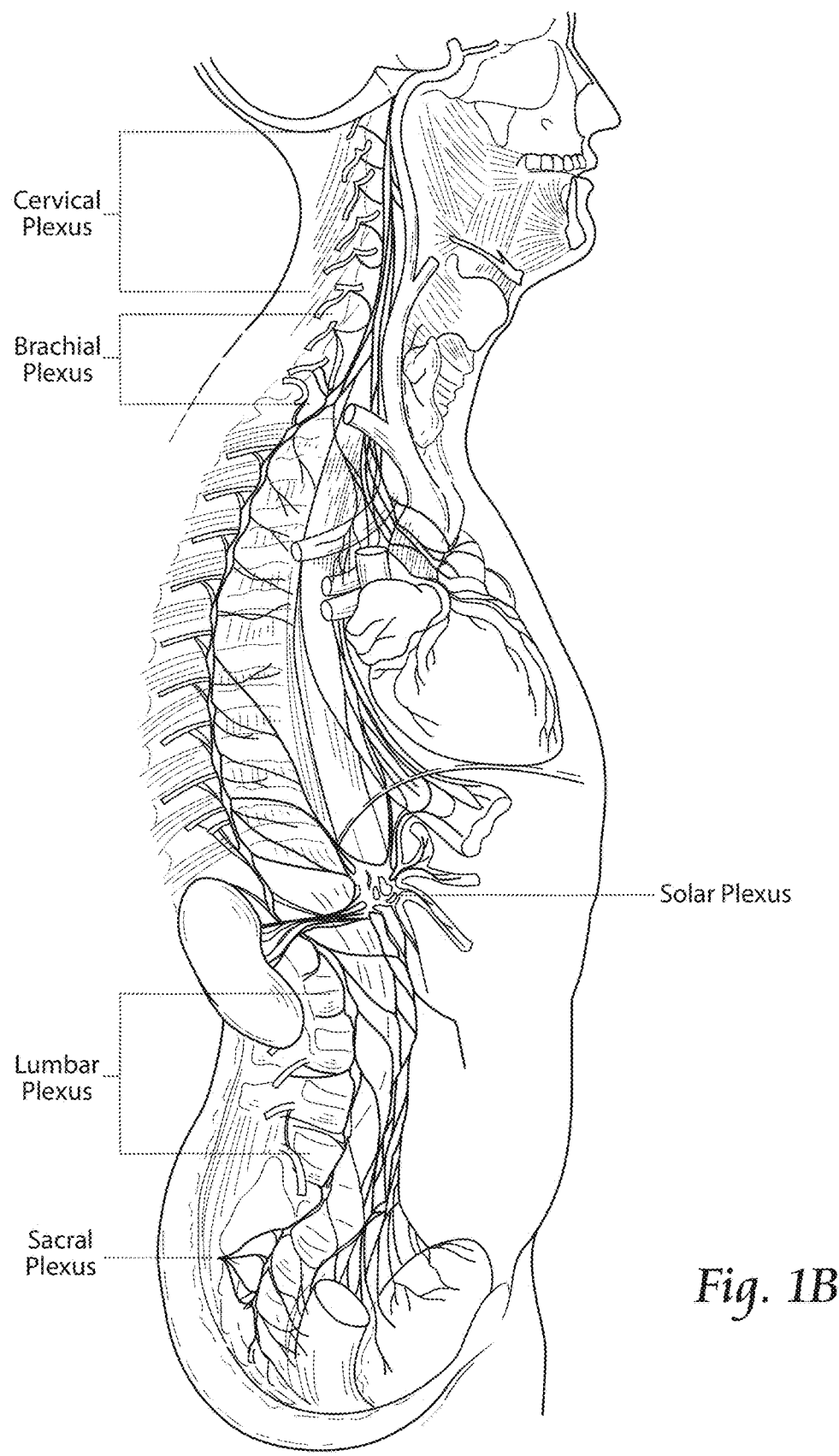

As generally shown in FIGS. 1A and 1B, the peripheral nervous system consists of nerve fibers and cell bodies outside the central nervous system (the brain and the spinal column) that conduct impulses to or away from the central nervous system. The peripheral nervous system is made up of nerves (called spinal nerves) that connect the central nervous system with peripheral structures. The spinal nerves of the peripheral nervous system arise from the spinal column and exit through intervertebral foramina in the vertebral column (spine). The afferent, or sensory, fibers of the peripheral nervous system convey neural impulses to the central nervous system from the sense organs (e.g., the eyes) and from sensory receptors in various parts of the body (e.g., the skin, muscles, etc.). The efferent, or motor, fibers convey neural impulses from the central nervous system to the effector organs (muscles and glands).

The somatic nervous system (SNS) is the part of the peripheral nervous system associated with the voluntary control of body movements through the action of skeletal muscles, and with reception of external stimuli, which helps keep the body in touch with its surroundings (e.g., touch, hearing, and sight). The system includes all the neurons connected with skeletal muscles, skin and sense organs. The somatic nervous system consists of efferent nerves responsible for sending central nervous signals for muscle contraction. A somatic nerve is a nerve of the somatic nervous system.

A. Spinal Nerves

A typical spinal nerve arises from the spinal cord by rootlets which converge to form two nerve roots, the dorsal (sensory) root and the ventral (motor) root. The dorsal and ventral roots unite into a mixed nerve trunk that divides into a smaller dorsal (posterior) primary ramus and a much larger ventral (anterior) primary ramus. The posterior primary rami serve a column of muscles on either side of the vertebral column, and a narrow strip of overlying skin. All of the other muscle and skin is supplied by the anterior primary rami.

The nerve roots that supply or turn into peripheral nerves can be generally categorized by the location on the spine where the roots exit the spinal cord, i.e., as generally shown in FIG. 2A, cervical (generally in the head/neck, designated C1 to C8), thoracic (generally in chest/upper back, designated T1 to T12), lumbar (generally in lower back, designated L1 to L5); and sacral (generally in the pelvis, designated S1 to S5). All peripheral nerves can be traced back (toward the spinal column) to one or more of the spinal nerve roots in either the cervical, thoracic, lumbar, or sacral regions of the spine. The neural impulses comprising pain felt in a given muscle or cutaneous region of the body pass through spinal nerves and (usually) one or more nerve plexuses. For this reason, the spinal nerves will sometimes be called in shorthand for the purpose of description "nerves of passage." The spinal nerves begin as roots at the spine, and can form trunks that divide by divisions or cords into branches that innervate skin and muscles.

Spinal nerves have motor fibers and sensory fibers. The motor fibers innervate certain muscles, while the sensory fibers innervate any structure or tissue that has sensation, which may include muscle. A skin area innervated by the sensory fibers of a single nerve root is known as a dermatome. A group of muscles primarily innervated by the motor fibers of a single nerve root is known as a myotome. Although slight variations do exist, dermatome and myotome patterns of distribution are relatively consistent from person to person. It is to be understood that, although muscles and skin are discussed as examples, nerves also innervate other nearby structures such as joints, bones, adipose tissue, connective tissue, etc. For example, portions or branches of the sciatic and femoral nerves do not innervate only the muscles and skin of the lower extremity, they also innervate the bone, joints, adipose tissue, connective tissue, etc., and treatment of pain therein is also contemplated hereby.

Each muscle in the body is supplied by a particular level or segment of the spinal cord and by its corresponding spinal nerve. The muscle, and its nerve make up a myotome. This is approximately the same for every person and are as follows:

C3, 4 and 5 supply the diaphragm (the large muscle between the chest and the belly that we use to breath).

C5 also supplies the shoulder muscles and the muscle that we use to bend our elbow.

C6 is for bending the wrist back.

C7 is for straightening the elbow.

C8 bends the fingers.

T1 spreads the fingers.

T1-T12 supplies the chest wall & abdominal muscles.

L2 bends the hip.

L3 straightens the knee.

L4 pulls the foot up.

L5 wiggles the toes.

S1 pulls the foot down.

S3, 4 and 5 supply the bladder, bowel, and sex organs and the anal and other pelvic muscles.

Dermatome is a Greek word which literally means "skin cutting". A dermatome is an area of the skin supplied by nerve fibers originating from the dorsal nerve root(s). The dermatomes are named according to the spinal nerve which supplies them. The dermatomes form into bands around the trunk (see FIGS. 2B and 2C), but in the limbs their organization can be more complex as a result of the dermatomes being "pulled out" as the limb buds form and develop into the limbs during embryological development.

In the diagrams or maps shown in FIGS. 2B and 2C, the boundaries of dermatomes are usually sharply defined. However, in life there is considerable overlap of innervation between adjacent dermatomes. Thus, if there is a loss of afferent nerve function by one spinal nerve sensation from the region of skin which it supplies is not usually completely lost as overlap from adjacent spinal nerves occurs; however, there may be a reduction in sensitivity.

B. Intercostal Nerves

Figure 3A:
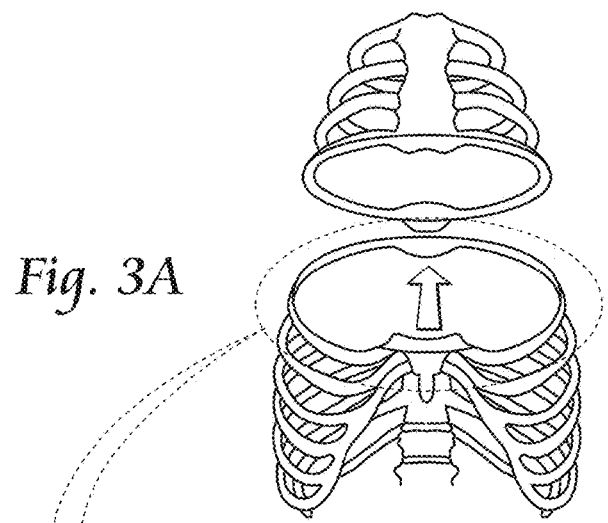
FIGS. 3A, 3B, and 3C are anatomic views of the intercostal spinal nerves of a human.
Figure 3B:
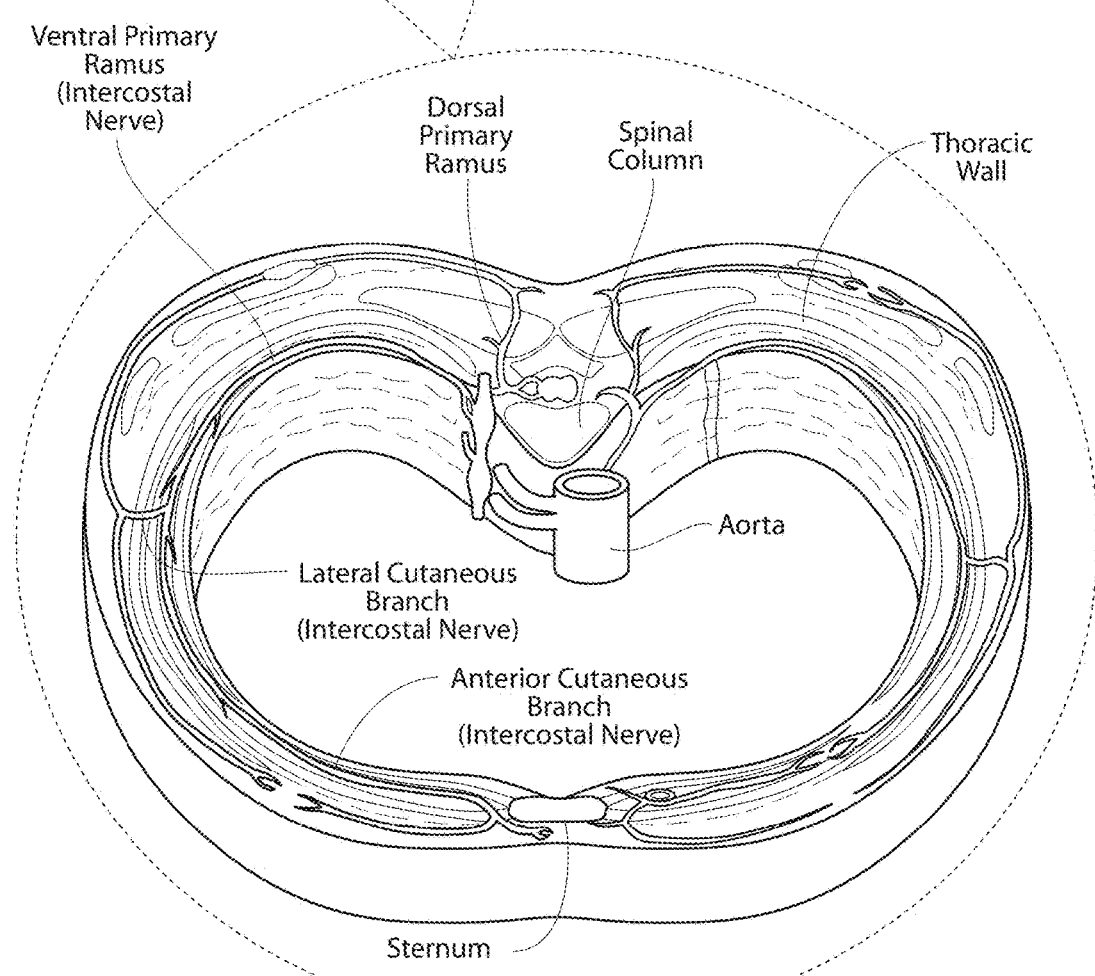
Figure 3C:
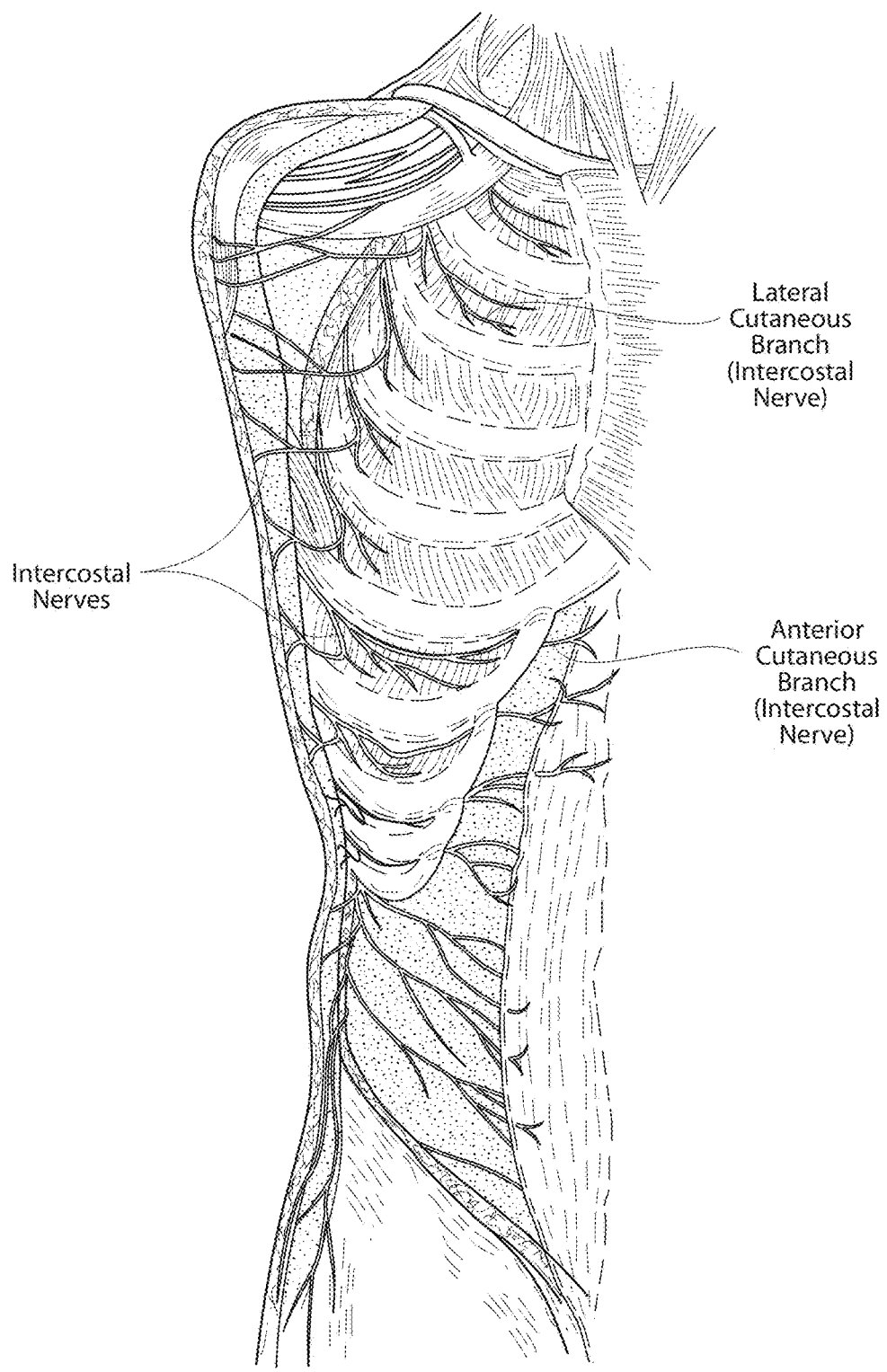

The intercostal nerves (see FIGS. 3A, 3B, and 3C) are the anterior divisions of the thoracic spinal nerves from the thoracic vertebrae T1 to T11. The intercostal nerves are distributed chiefly to the thoracic pleura and abdominal peritoneum and differ from the anterior divisions of the other spinal nerves in that each pursues an independent course without plexus formation.

The first two nerves supply fibers to the upper limb in addition to their thoracic branches; the next four are limited in their distribution to the parietes of the thorax; the lower five supply the parietes of the thorax and abdomen. The 7th intercostal nerve terminates at the xyphoid process, at the lower end of the sternum. The 10th intercostal nerve terminates at the umbilicus. The twelfth (subcostal) thoracic is distributed to the abdominal wall and groin.

Branches of a typical intercostal nerve include the ventral primary ramus; lateral cutaneous branches that pass beyond the angles of the rubs and innervate the internal and external intercostal muscles approximately halfway around the thorax; and the anterior cutaneous branches that supply the skin on the anterior aspect of the thorax and abdomen.

C. Spinal Nerve Plexuses

A nerve plexus is a network of intersecting anterior primary rami. The sets of anterior primary rami form nerve trunks that ultimately further divide through divisions and then into cords and then into nerve branches serving the same area of the body. The nerve branches are mixed, i.e., they carry both motor and sensory fibers. The branches innervate the skin, muscle, or other structures. One example of the entry of a terminal motor nerve branch into muscle is called a motor point.

As shown in FIGS. 1A and 1B, there are several nerve plexuses in the body, including (i) the brachial plexus, which serves the chest, shoulders, arms and hands; (ii) the lumbar plexus, which serves the back, abdomen, groin, thighs, knees, and calves; (iii) the sacral plexus, which serves the buttocks, thighs, calves, and feet; (iv) the cervical plexus, which serves the head, neck and shoulders; and (vi) the solar plexus, which serves internal organs. The following describes, from an anatomic perspective, the spinal nerves of passage passing through the various plexuses, and the muscle and/or skin regions they innervate and where pain can be felt.

1. The Brachial Plexus

Figure 4A:
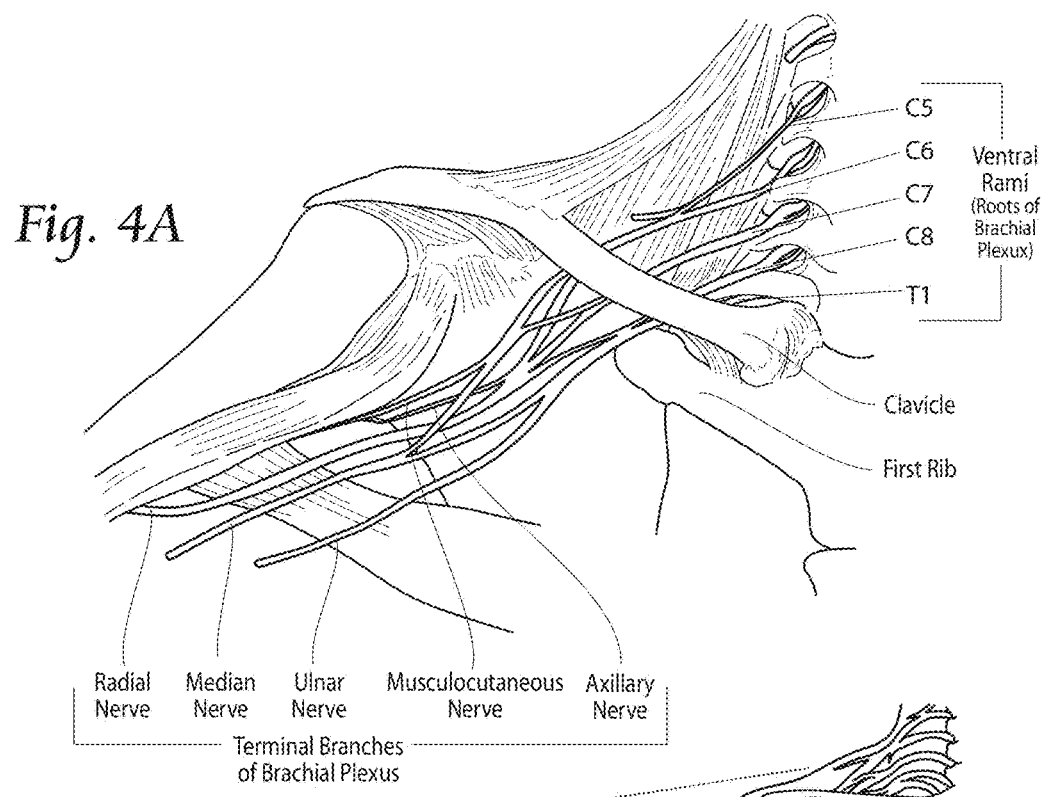
FIGS. 4A and 4B are anatomic views of the spinal nerves of the brachial plexus.
Figure 4B:
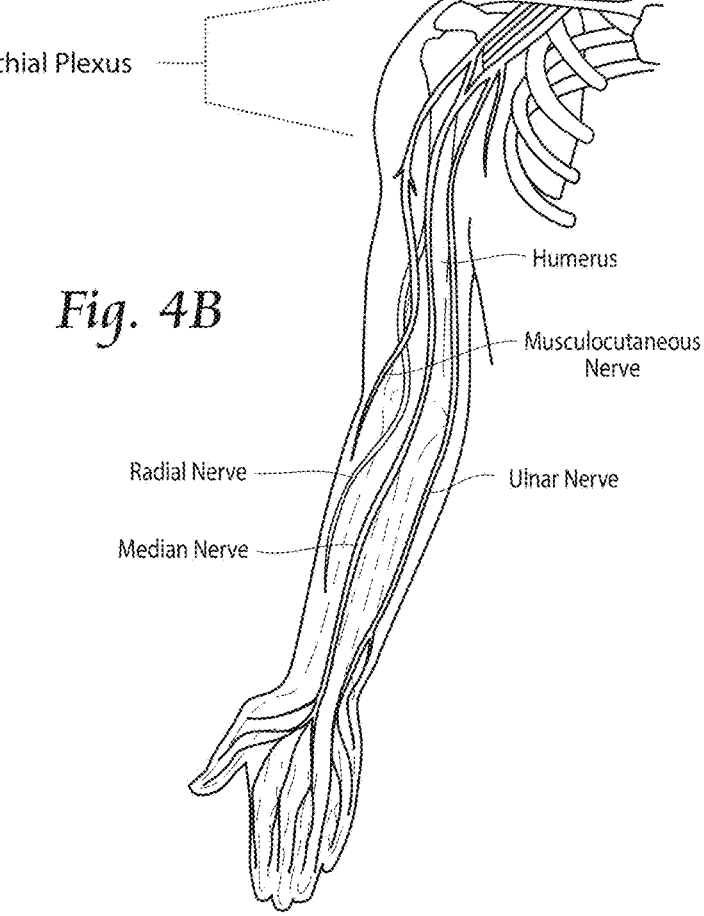

Most nerves in the upper limb arise from the brachial plexus, as shown in FIGS. 4A and 4B. The brachial plexus begins in the neck (vertebrae C5 through C7), forms trunks, and extends through divisions and cords into the axilla (underarm), where nearly all the nerve branches arise. Primary nerve branches of the brachial plexus include the musculocutaneous nerve; the median nerve; the ulnar nerve; the axillary nerve; and the radial nerve.

a. The Musculocutaneous Nerve

The musculocutaneous nerve arises from the lateral cord of the brachial plexus. Its fibers are derived from cervical vertebrae C5, C6. The musculocutaneous nerve penetrates the coracobrachialis muscle and passes obliquely between the biceps brachii and the brachialis, to the lateral side of the arm. Just above the elbow, the musculocutaneous nerve pierces the deep fascia lateral to the tendon of the biceps brachii continues into the forearm as the lateral antebrachial cutaneous nerve. In its course through the arm, the musculocutaneous nerve innervates the coracobrachialis, biceps brachii, and the greater part of the brachialis.

b. The Median Nerve

The median nerve is formed from parts of the medial and lateral cords of the brachial plexus, and continues down the arm to enter the forearm with the brachial artery. It originates from the brachial plexus with roots from cervical vertebrae C5, C6, C7 and thoracic vertebra T1. The median nerve innervates all of the flexors in the forearm, except flexor carpi ulnaris and that part of flexor digitorum profundus that supplies the medial two digits. The latter two muscles are supplied by the ulnar nerve of the brachial plexus. The median nerve is the only nerve that passes through the carpal tunnel, where it may be compressed to cause carpal tunnel syndrome.

The main portion of the median nerve supplies the following muscles: (i) the superficial group comprising pronator teres muscle; flexor carpi radialis muscle; palmaris longus muscle; and (ii) the intermediate group comprising flexor digitorum superficialis muscle.

The anterior interosseus branch of the median nerve supplies the deep group comprising flexor digitorum profundus muscle (lateral half); flexor pollicis longus muscle; and pronator quadratus.

In the hand, the median nerve supplies motor innervation to the 1st and 2nd lumbrical muscles. It also supplies the muscles of the thenar eminence by a recurrent thenar branch. The rest of the intrinsic muscles of the hand are supplied by the ulnar nerve of the brachial plexus.

The median nerve innervates the skin of the palmar side of the thumb, the index and middle finger, half the ring finger, and the nail bed of these fingers. The lateral part of the palm is supplied by the palmar cutaneous branch of the median nerve, which leaves the nerve proximal to the wrist creases. The palmar cutaneous branch travels in a separate fascial groove adjacent to the flexor carpi radialis and then superficial to the flexor retinaculum. It is therefore spared in carpal tunnel syndrome.

c. The Ulnar Nerve

The ulnar nerve comes from the medial cord of the brachial plexus, and descends on the posteromedial aspect of the humerus. It goes behind the medial epicondyle, through the cubital tunnel at the elbow (where it is vulnerable to injury for a few centimeters, just above the joint). One method of injuring the nerve is to strike the medial epicondyle of the humerus from posteriorly, or inferiorly with the elbow flexed. The ulnar nerve is trapped between the bone and the overlying skin at this point. This is commonly referred to as hitting one's "funny bone."

The ulnar nerve is the largest nerve not protected by muscle or bone in the human body. The ulnar nerve is the only unprotected nerve that does not serve a purely sensory function. The ulnar nerve is directly connected to the little finger, and the adjacent half of the ring finger, supplying the palmar side of these fingers, including both front and back of the tips, as far back as the fingernail beds.

The ulnar nerve and its branches innervate muscles in the forearm and hand. In the forearm, the muscular branches of ulnar nerve innervates the flexor carpi ulnaris and the flexor digitorum profundus (medial half). In the hand, the deep branch of ulnar nerve innervates hypothenar muscles; opponens digiti minimi; abductor digiti minimi; flexor digiti minimi brevis; adductor pollicis; flexor pollicis brevis (deep head); the third and fourth lumbrical muscles; dorsal interossei; palmar interossei. In the hand, the superficial branch of ulnar nerve innervates palmaris brevis.

The ulnar nerve also provides sensory innervation to the fifth digit and the medial half of the fourth digit, and the corresponding part of the palm. The Palmar branch of ulnar nerve supplies cutaneous innervation to the anterior skin and nails. The dorsal branch of ulnar nerve supplies cutaneous innervation to the posterior skin (except the nails).

d. The Axillary Nerve

The axillary nerve comes off the posterior cord of the brachial plexus at the level of the axilla (armpit) and carries nerve fibers from vertebrae C5 and C6. The axillary nerve travels through the quadrangular space with the posterior circumflex humeral artery and vein. It supplies two muscles: the deltoid (a muscle of the shoulder), and the teres minor (one of the rotator cuff muscles). The axillary nerve also carries sensory information from the shoulder joint, as well as from the skin covering the inferior region of the deltoid muscle, i.e., the "regimental badge" area (which is innervated by the superior lateral cutaneous nerve branch of the axillary nerve). When the axillary nerve splits off from the posterior cord, the continuation of the cord is the radial nerve.

e. The Radial Nerve

The radial nerve supplies the upper limb, supplying the triceps brachii muscle of the arm, as well as all twelve muscles in the posterior osteofascial compartment of the forearm, as well as the associated joints and overlying skin. The radial nerve originates from the posterior cord of the brachial plexus with roots from cervical vertebrae C5, C6, C7, C8 and thoracic vertebra T1.

Cutaneous innervation is provided by the following nerves: (i) posterior cutaneous nerve of arm (originates in axilla); (ii) inferior lateral cutaneous nerve of arm (originates in arm); and (iii) posterior cutaneous nerve of forearm (originates in arm). The superficial branch of the radial nerve provides sensory innervation to much of the back of the hand, including the web of skin between the thumb and index finger.

Muscular branches of the radial nerve innervate the triceps brachii; anconeus brachioradialis; and the extensor carpi radialis longus.

The deep branch of the radial nerve innervates the extensor carpi radialis brevis; supinator; posterior interosseous nerve (a continuation of the deep branch after the supinator): extensor digitorum; extensor digiti minimi; extensor carpi ulnaris; abductor pollicis longus; extensor pollicis brevis; extensor pollicis longus; and extensor indicis.

The radial nerve (and its deep branch) provides motor innervation to the muscles in the posterior compartment of the arm and forearm, which are mostly extensors.

2. Sacral and Lumbar Plexuses

Figure 5:
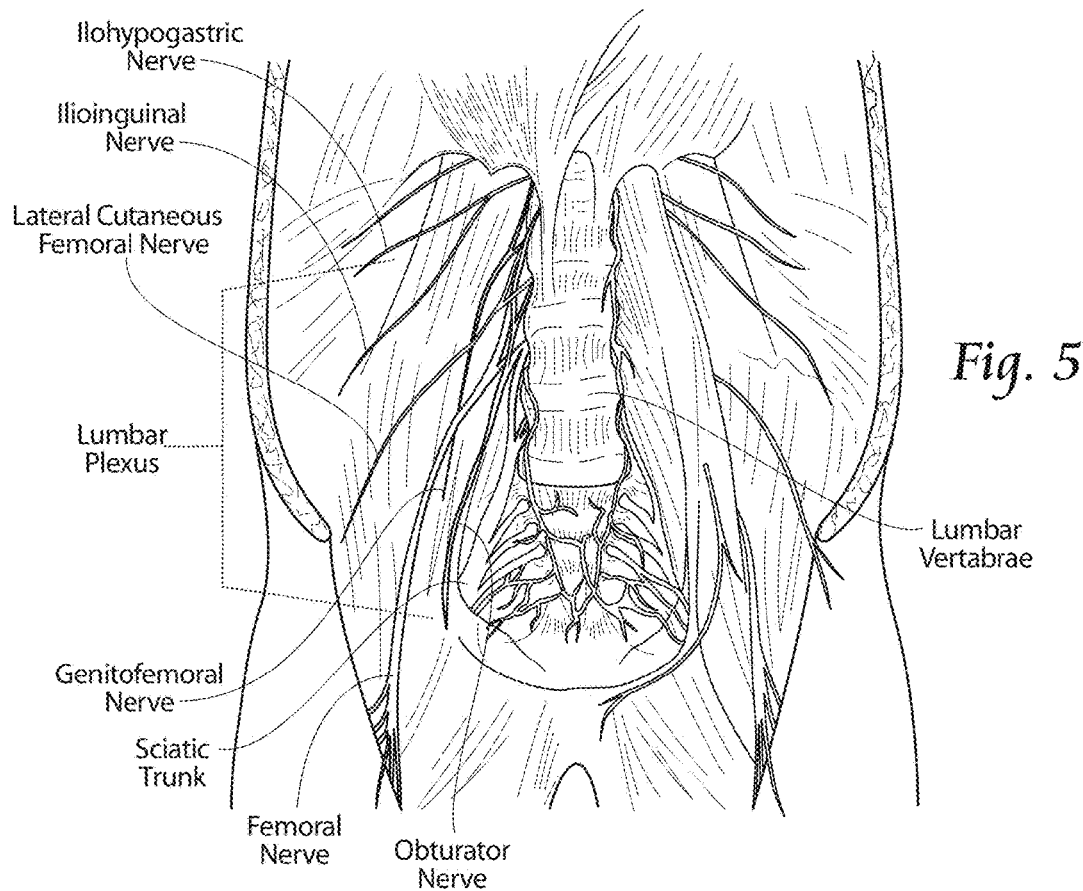
FIG. 5 is an anatomic views of the spinal nerves of the lumbar plexus.

The lumbar plexus (see FIG. 5) is a nervous plexus in the lumbar region of the body and forms part of the lumbosacral plexus. It is formed by the ventral divisions of the first four lumbar nerves (L1-L4) and from contributions of the subcostal thoracic nerve (T12), which is the last (most inferior) thoracic nerve.

Additionally, the ventral rami of sacral vertebrae S2 and S3 nerves emerge between digitations of the piriformis and coccygeus nuscles. The descending part of the lumbar vertebrae L4 nerve unites with the ventral ramus of the lumbar vertebrae L5 nerve to form a thick, cordlike lumbosacral trunk. The lumbosacral trunk joins the sacral plexus (see FIG. 6). The main nerves of the lower limbs arise from the lumbar and sacral plexuses.

a. Nerves of the Sacral Plexus

The sacral plexus provides motor and sensory nerves for the posterior thigh, most of the lower leg, and the entire foot.

(1) The Sciatic Nerve

Figure 6:
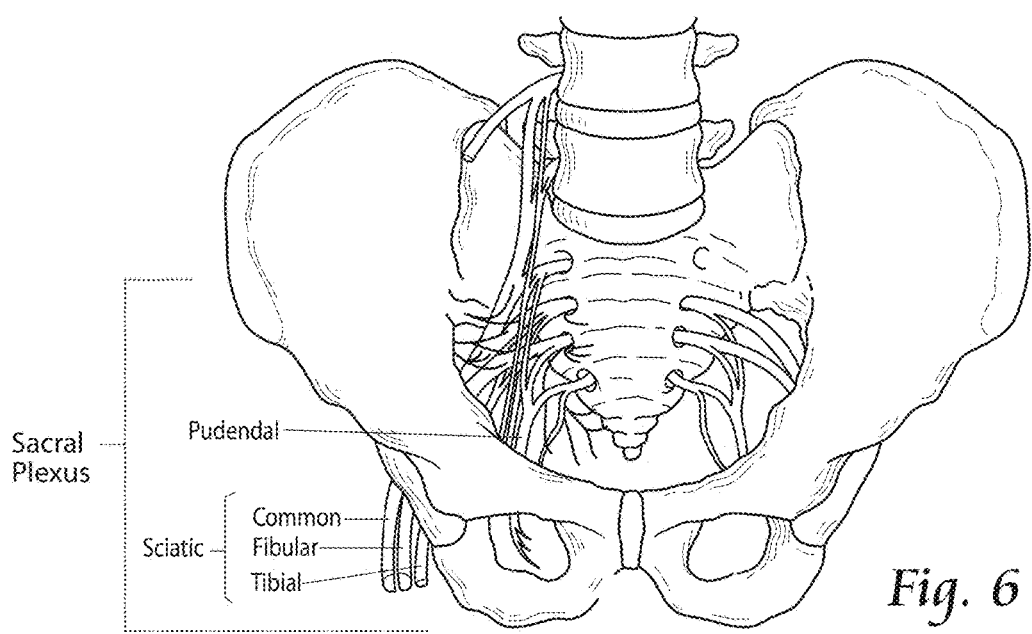
FIG. 6 is an anatomic view of the spinal nerves of the sacral plexus.

As shown in FIGS. 1A and 6, the sciatic nerve (also known as the ischiatic nerve) arises from the sacral plexus. It is the longest and widest single nerve in the human body. It begins in the lower back and runs through the buttock and down the lower limb. The sciatic nerve supplies nearly the whole of the skin of the leg, the muscles of the back of the thigh, and those of the leg and foot. It is derived from spinal nerves L4 through S3. It contains fibers from both the anterior and posterior divisions of the lumbosacral plexus.

The nerve gives off articular and muscular branches. The articular branches (rami articulares) arise from the upper part of the nerve and supply the hip-joint, perforating the posterior part of its capsule; they are sometimes derived from the sacral plexus. The muscular branches (rami musculares) innervate the following muscles of the lower limb: biceps femoris, semitendinosus, semimembranosus, and adductor magnus. The nerve to the short head of the biceps femoris comes from the common peroneal part of the sciatic, while the other muscular branches arise from the tibial portion, as may be seen in those cases where there is a high division of the sciatic nerve.

The muscular branch of the sciatic nerve eventually gives off the tibial nerve (shown in FIG. 1A) and common peroneal nerve (also shown in FIG. 1A), which innervates the muscles of the (lower) leg. The tibial nerve goes on to innervate all muscles of the foot except the extensor digitorum brevis (which is innervated by the peroneal nerve).

Two major branches of the sciatic nerve are the tibial and common peroneal nerves that innervate much of the lower leg (around and below the knee). For example, the tibial nerve innervates the gastrocnemius, popliteus, soleus and plantaris muscles and the knee joint. Most of the foot is innervated by the tibial and peroneal nerve.

b. Nerves of the Lumbar Plexus

The lumbar plexus (see FIG. 5) provides motor, sensory, and autonomic fibres to gluteal and inguinal regions and to the lower extremities. The gluteal muscles are the three muscles that make up the buttocks: the gluteus maximus muscle, gluteus medius muscle and gluteus minimus muscle. The inguinal region is situated in the groin or in either of the lowest lateral regions of the abdomen.

(1) The Iliohypogastric Nerve

The iliohypogastric nerve (see FIG. 5) runs anterior to the psoas major on its proximal lateral border to run laterally and obliquely on the anterior side of quadratus lumborum. Lateral to this muscle, it pierces the transversus abdominis to run above the iliac crest between that muscle and abdominal internal oblique. It gives off several motor branches to these muscles and a sensory branch to the skin of the lateral hip. Its terminal branch then runs parallel to the inguinal ligament to exit the aponeurosis of the abdominal external oblique above the external inguinal ring where it supplies the skin above the inguinal ligament (i.e. the hypogastric region) with the anterior cutaneous branch.

(2) The Ilioinguinal Nerve

The ilioinguinal nerve (see FIG. 5) closely follows the iliohypogastric nerve on the quadratus lumborum, but then passes below it to run at the level of the iliac crest. It pierces the lateral abdominal wall and runs medially at the level of the inguinal ligament where it supplies motor branches to both transversus abdominis and sensory branches through the external inguinal ring to the skin over the pubic symphysis and the lateral aspect of the labia majora or scrotum.

(3) The Genitofemoral Nerve

The genitofemoral nerve (see FIG. 5) pierces psoas major anteriorly below the former two nerves to immediately split into two branches that run downward on the anterior side of the muscle. The lateral femoral branch is purely sensory. It pierces the vascular lacuna near the saphenous hiatus and supplies the skin below the inguinal ligament (i.e. proximal, lateral aspect of femoral triangle). The genital branch differs in males and females. In males it runs in the spermatic cord and in females in the inguinal canal together with the teres uteri ligament. It then sends sensory branches to the scrotal skin in males and the labia majora in females. In males it supplies motor innervation to the cremaster.

(4) The Lateral Cutaneous Femoral Nerve

The lateral cutaneous femoral nerve (see FIG. 5) pierces psoas major on its lateral side and runs obliquely downward below the iliac fascia. Medial to the anterior superior iliac spine it leaves the pelvic area through the lateral muscular lacuna. In the thigh it briefly passes under the fascia lata before it breaches the fascia and supplies the skin of the anterior thigh.

(5) The Obturator Nerve

The obturator nerve (see FIG. 5) leaves the lumbar plexus and descends behind psoas major on it medial side, then follows the linea terminalis and exits through the obturator canal. In the thigh, it sends motor branches to obturator externus before dividing into an anterior and a posterior branch, both of which continues distally. These branches are separated by adductor brevis and supply all thigh adductors with motor innervation: pectineus, adductor longus, adductor brevis, adductor magnus, adductor minimus, and gracilis. The anterior branch contributes a terminal, sensory branch which passes along the anterior border of gracilis and supplies the skin on the medial, distal part of the thigh.

(6) The Femoral Nerve

Figure 16A:
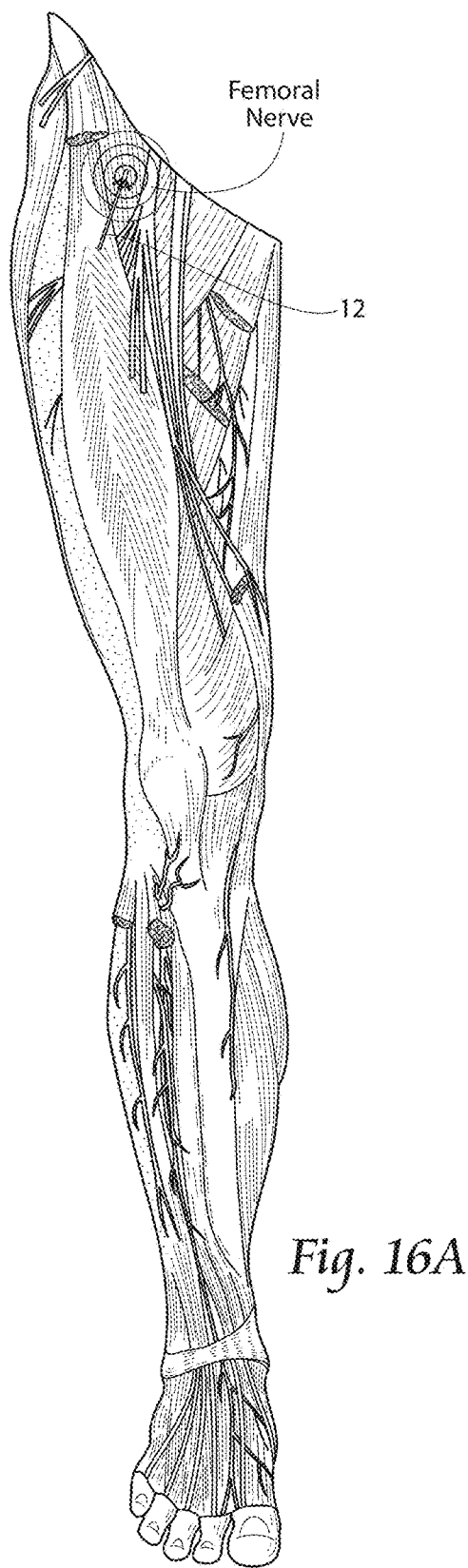
FIGS. 16A, 16B, and 16C are schematic anatomic views of a system for applying nerve of passage stimulation to a femoral nerve.

The femoral nerve (see FIG. 5 and also FIG. 16A) is the largest and longest nerve of the lumbar plexus. It gives motor innervation to iliopsoas, pectineus, sartorius, and quadriceps femoris; and sensory innervation to the anterior thigh, posterior lower leg, and hindfoot. It runs in a groove between psoas major and iliacus giving off branches to both muscles. In the thigh it divides into numerous sensory and muscular branches and the saphenous nerve, its long sensory terminal branch which continues down to the foot.

The femoral nerve has anterior branches (intermediate cutaneous nerve and medial cutaneous nerve) and posterior branches. The saphenous nerve (branch of the femoral nerve) provides cutaneous (skin) sensation in the medial leg. Other branches of the femoral nerve innervate structures (such as muscles, joints, and other tissues) in the thigh and around the hip and knee joints. As an example, branches of the femoral nerve innervate the hip joint, knee joint, and the four parts of the Quadriceps femoris (muscle): Rectus femoris (in the middle of the thigh) originates on the ilium and covers most of the other three quadriceps muscles. Under (or deep to) the rectus femoris are the other 3 of the quadriceps muscles, which originate from the body of the femur. Vastus lateralis (on the outer side of the thigh) is on the lateral side of the femur. Vastus medialis (on the inner part thigh) is on the medial side of the femur. Vastus intermedius (on the top or front of the thigh) lies between vastus lateralis and vastus medialis on the front of the femur. Braches of the femoral nerve often innervate the pectineus and Sartorius muscles arises.

3. The Cervical Plexus

Figure 7:
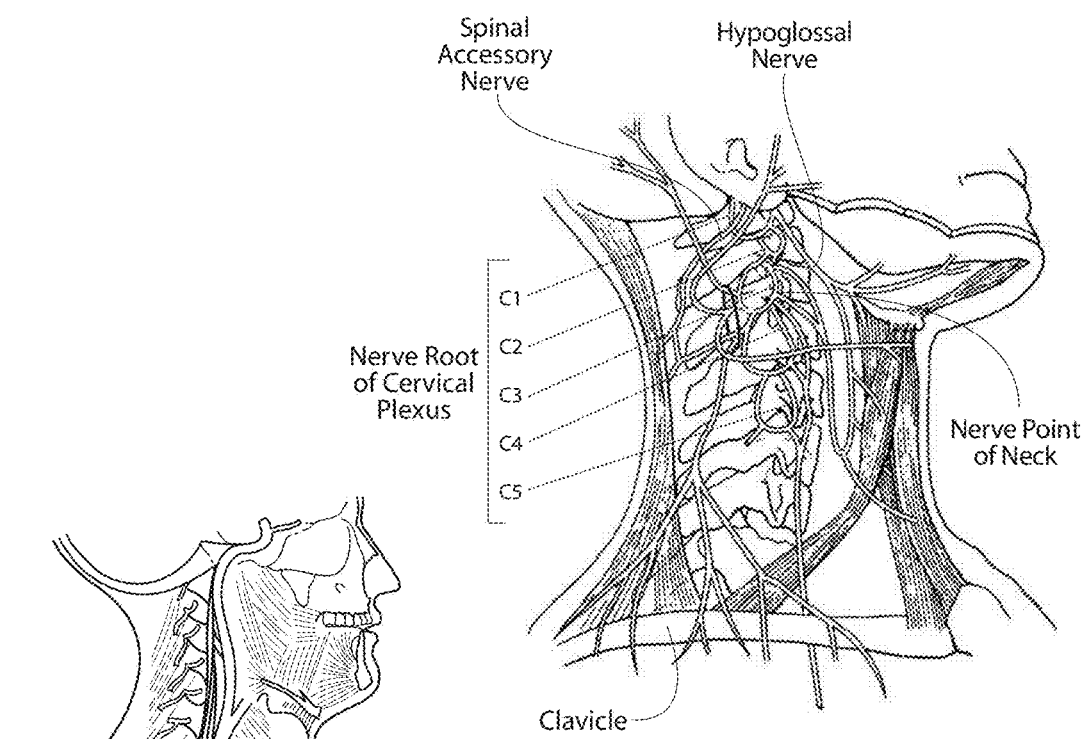
FIG. 7 is an anatomic view of the spinal nerves of the cervical plexus.

The cervical plexus (see FIG. 7) is a plexus of the ventral rami of the first four cervical spinal nerves which are located from C1 to C4 cervical segment in the neck. They are located laterally to the transverse processes between prevertebral muscles from the medial side and vertebral (m.scalenus, m.levator scapulae, m.splenius cervicis) from lateral side. Here there is anastomosis with accessory nerve, hypoglossal nerve and sympathetic trunk.

The cervical plexus is located in the neck, deep to sternocleidomastoid. Nerves formed from the cervical plexus innervate the back of the head, as well as some neck muscles. The branches of the cervical plexus emerge from the posterior triangle at the nerve point, a point which lies midway on the posterior border of the Sternocleidomastoid.

The nerves formed by the cervical plexus supply the back of the head, the neck and the shoulders. The face is supplied by a cranial nerve, the trigeminal nerve. The upper four posterior primary rami are larger than the anterior primary rami. The C1 posterior primary ramus does not usually supply the skin. The C2 posterior primary ramus forms the greater occipital nerve which supplies the posterior scalp. The upper four anterior primary rami form the cervical plexus. The cervical plexus supplies the skin over the anterior and lateral neck to just below the clavicle. The plexus also supplies the muscles of the neck including the scalenes, the strap muscles, and the diaphragm.

The cervical plexus has two types of branches: cutaneous and muscular.

The cutaneous branches include the lesser occipital nerve, which innervates lateral part of occipital region (C2 nerve only); the great auricular nerve, which innervates skin near concha auricle and external acoustic meatus (C2 and C3 nerves); the transverse cervical nerve, which innervates anterior region of neck (C2 and C3 nerves); and the supraclavicular nerves, which innervate region of suprascapularis, shoulder, and upper thoracic region (C3,C4 Nerves)

The muscular branches include the ansa cervicalis (loop formed from C1-C3), etc. (geniohyoid (C1 only), thyrohyoid (C1 only), sternothyroid, sternohyoid, omohyoid); phrenic (C3-C5 (primarily C4)), which innervates the diaphragm; the segmental branches (C1-C4), which innervate the anterior and middle scalenes.

4. The Solar Plexus

Figure 8:
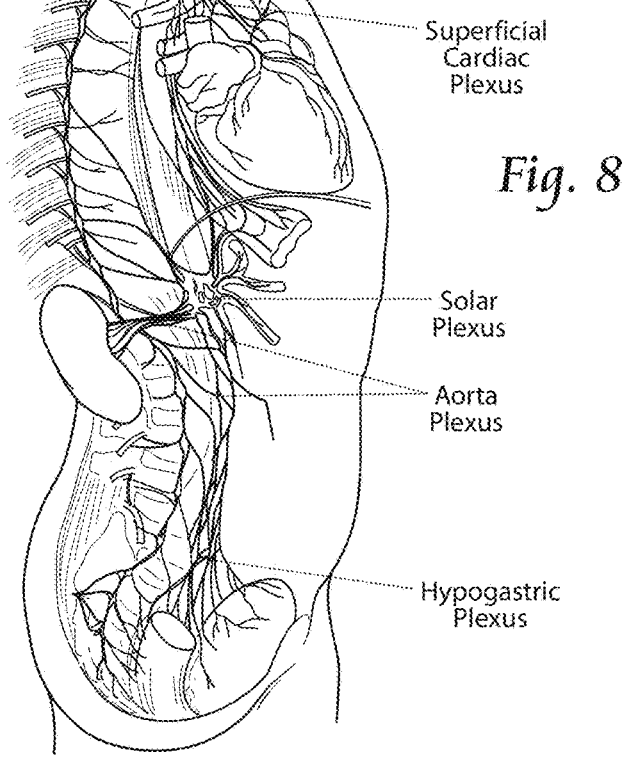
FIG. 8 is an anatomic view of the spinal nerves of the solar plexus.

The solar plexus (see FIG. 8) is a dense cluster of nerve cells and supporting tissue, located behind the stomach in the region of the celiac artery just below the diaphragm. It is also known as the celiac plexus. Rich in ganglia and interconnected neurons, the solar plexus is the largest autonomic nerve center in the abdominal cavity. Through branches it controls many vital functions such as adrenal secretion and intestinal contraction.

Derived from the solar plexus are the phrenic plexus (producing contractions of the diaphragm, and providing sensory innervation for many components of the mediastinum and pleura); the renal plexuses (affecting renal function); the spermatic plexus (affecting function of the testis); as well as the gastric plexus; the hepatic plexus; the splenic plexus; the superior mesenteric plexus; and the aortic plexus.

II. The System

The various aspects of the invention will be described in connection with the placement of one or more leads 12 having one or more electrodes 14, or leadless electrodes, in muscle or other tissue, and in electrical proximity but away from nerves, for improved recruitment of targeted nerves for therapeutic purposes, such as for the treatment of pain. That is because the features and advantages that arise due to the invention are well suited to this purpose. It is to be appreciated that regions of pain can include any or all portions of the body, whether or not such portion is physically present on the body at the time of stimulation according to the present invention, including arms, legs, and trunk in both humans and animals. A portion may not be physically present on the body due to amputation, resection, otherwise removed (e.g. trauma), or it may be congenitally missing.

A. Stimulation of Nerves of Passage

Figure 9:
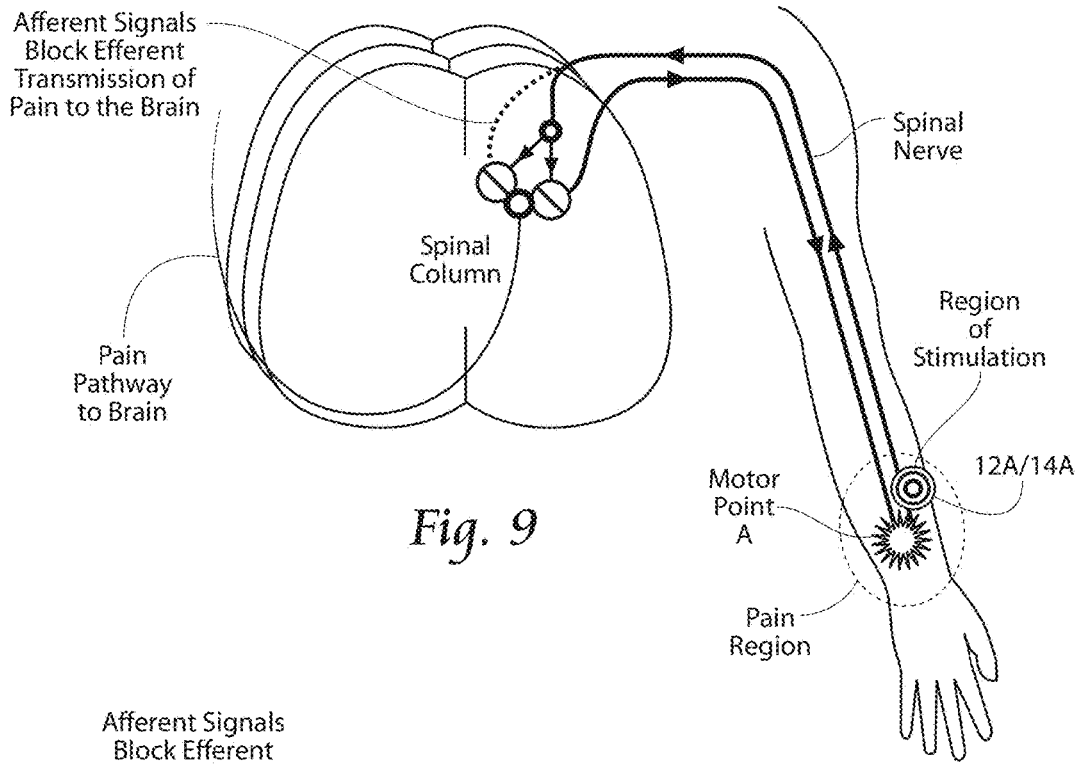
FIG. 9 is an idealized, diagrammatic view showing a motor point stimulation system.

FIG. 9 shows a typical "motor point" system and method for stimulating a nerve or muscle A by placing a lead 12(A) with its electrode 14(A) close to motor point A. As previously described, a motor point A is the location where the innervating spinal nerve enters the muscle. At that location, the electrical stimulation intensity required to elicit a full contraction is at the minimum. Any other electrode placement location in the muscle located further from the motor point would require more stimulation intensity to elicit the same muscle contraction.

Figure 10:
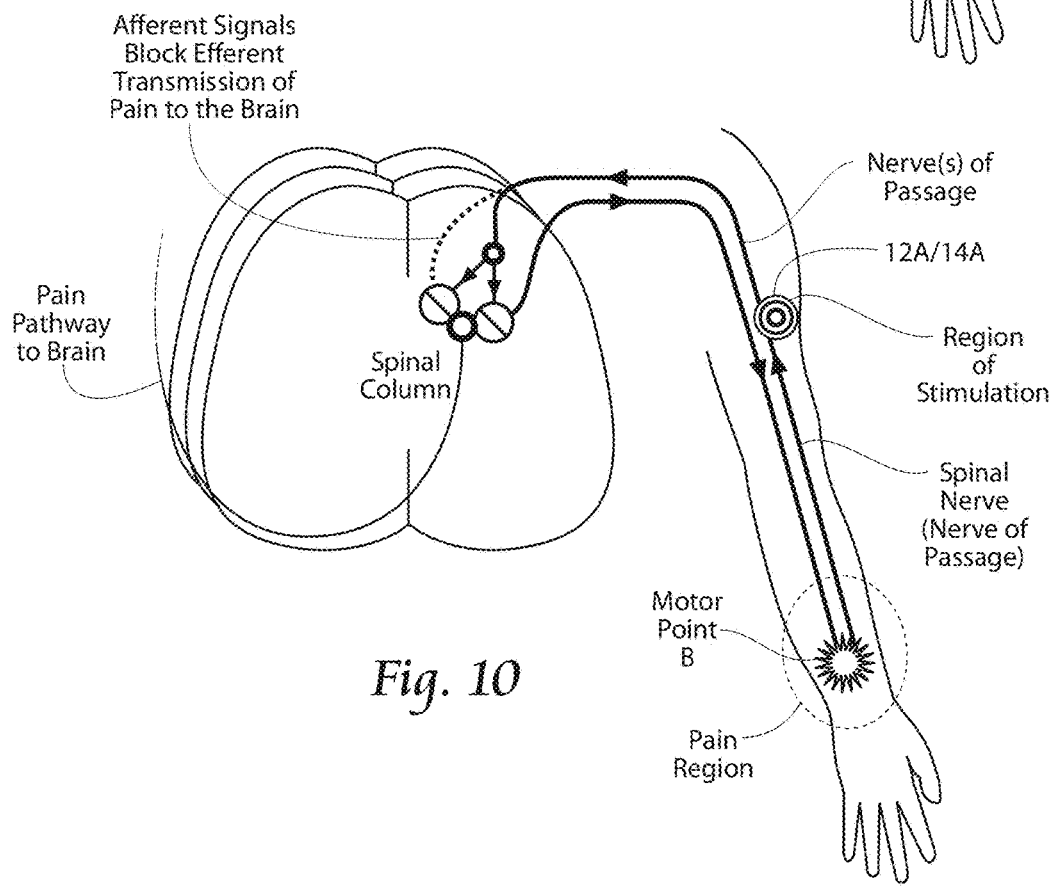
FIG. 10 is an idealized, diagrammatic view showing a nerve of passage stimulation system.

FIG. 10 shows a "nerves of passage" system and method, that is unlike the "motor point" system and method shown in FIG. 9, and which incorporates the features of the invention. As shown in FIG. 10, the system and method identifies a region where there is a local manifestation of pain. The region of pain can comprise, e.g., skin, bone, a joint, connective tissue, muscle, or other tissue or structure. The system and method identify one or more spinal nerves that are located anatomically upstream or cranial to the region where pain is manifested, through which neural impulses comprising the action potentials that will be interpreted as pain. A given spinal nerve that is identified can comprise a nerve trunk located in a nerve plexus, or a divisions and/or a cord of a nerve trunk, or a nerve branch, provided that it is upstream or cranial of where the nerve innervates the region affected by the pain. The given spinal nerve can be identified by medical professionals using textbooks of human anatomy along with their knowledge of the site and the nature of the pain or injury, as well as by physical manipulated and/or imaging, e.g., by ultrasound, fluoroscopy, or X-ray examination, of the region where pain is manifested. A desired criteria of the selection includes identifying the location of tissue (e.g. muscle, adipose, connective, or other tissue) in electrical proximity to but spaced away from the nerve or passage, which can be accessed by placement of one or more stimulation electrodes, aided if necessary by ultrasonic or electro-location techniques. The nerve identified comprises a targeted "nerve of passage." The muscle identified comprises the "targeted tissue" or "targeted muscle." In a preferred embodiment, the electrodes are percutaneously inserted using percutaneous leads.

The system and method place the one or more leads 12(B) with its electrode 14(B), or leadless electrodes, in the targeted tissue in electrical proximity to but spaced away from the targeted nerve of passage. The system and method apply electrical stimulation through the one or more stimulation electrodes to electrically activate or recruit the targeted nerve of passage that conveys the neural impulses comprising the pain to the spinal column.

The system and method can apply electrical stimulation to nerves of passage throughout the body. For example, the nerves of passage can comprise one or more spinal nerves in the brachial plexus, to treat pain in the chest, shoulders, arms and hands; and/or one or more spinal nerves in the lumbar plexus, to treat pain in the back, abdomen, thighs, knees, and calves; and/or one or more spinal nerves in the sacral plexus, to treat pain in the buttocks, thighs, calves, and feet; and/or one or more spinal nerves in the cervical plexus, to treat pain in the head, neck and shoulders; and/or one or more spinal nerves in the solar plexus, to treat pain or dysfunction in internal organs.

For example, if the pinky finger hurts, the system and method can identify and stimulate the ulnar nerve at a location that it is upstream or cranial of where the nerve innervates the muscle or skin of the pinky finger, e.g., in the palm of the hand, forearm, and/or upper arm. If electrical stimulation activates the target nerve of passage sufficiently at the correct intensity, then the patient will feel a comfortable tingling sensation called a paresthesia in the same region as their pain, which overlap with the region of pain and/or otherwise reduce pain.

It is to be appreciated that the sensation could be described with other words such as buzzing, thumping, etc. Evoking paresthesias in the region of pain confirms correct lead placement and indicates stimulus intensity is sufficient to reduce pain. Inserting a lead 12 percutaneously allows the lead 12 to be placed quickly and easily, and placing the lead 12 in a peripheral location, i.e., muscle, where it is less likely to be dislodged, addresses the lead migration problems of spinal cord stimulation that result in decreased paresthesia coverage, decreased pain relief, and the need for frequent patient visits for reprogramming.

Placing the lead 12 percutaneously in muscle in electrical proximity to but spaced away from the targeted nerve of passage minimize complications related to lead placement and movement. In a percutaneous system, an electrode lead 12, such as a coiled fine wire electrode lead may be used because it is minimally-invasive and well suited for placement in proximity to a nerve of passage. The lead can be sized and configured to withstand mechanical forces and resist migration during long-term use, particularly in flexible regions of the body, such as the shoulder, elbow, and knee.

B. The Lead

Figure 11A:
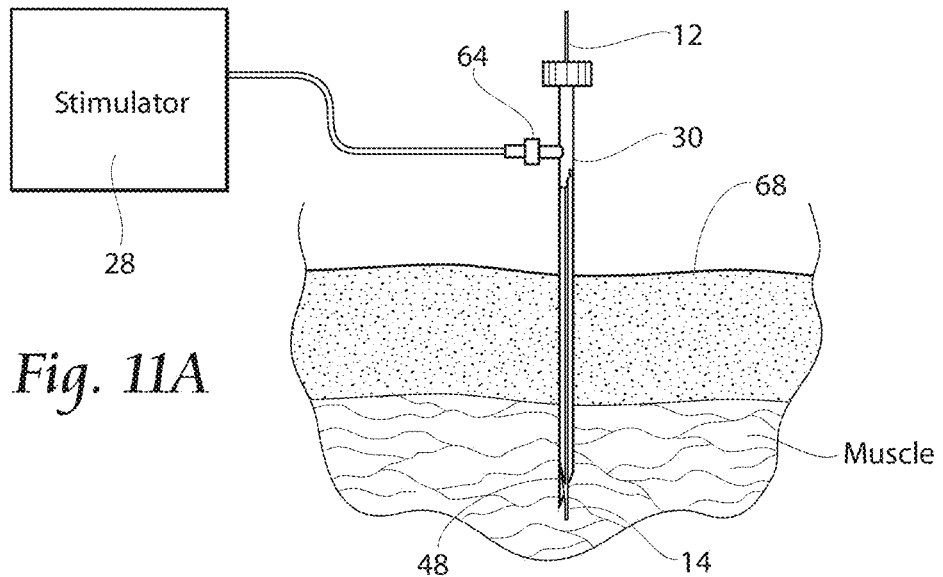
FIGS. 11A to 11D are views showing a percutaneous lead that can form a part of a nerve of passage stimulation system.
Figure 11B:
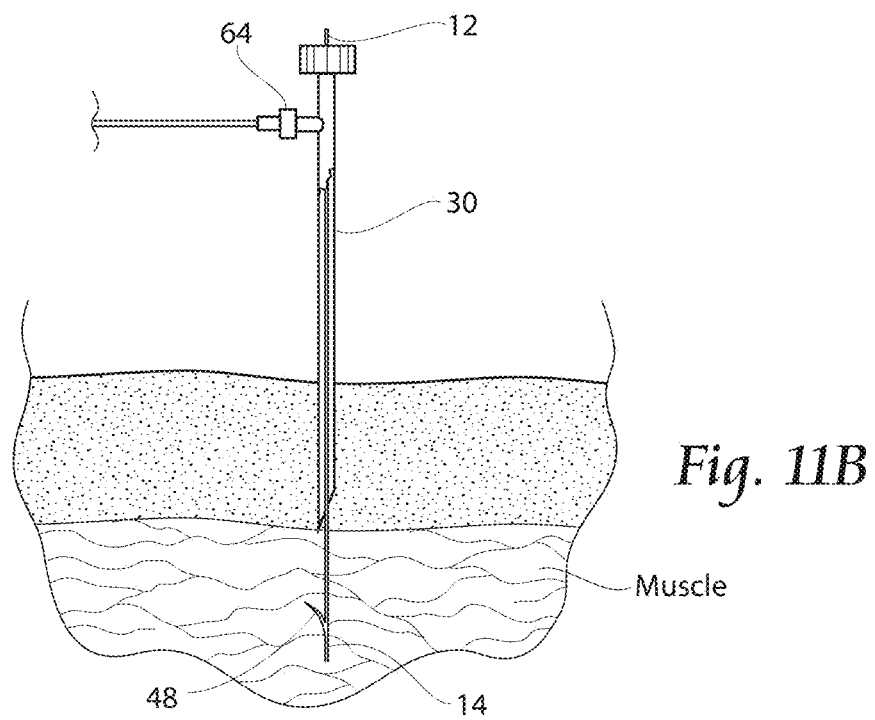
Figure 11C:
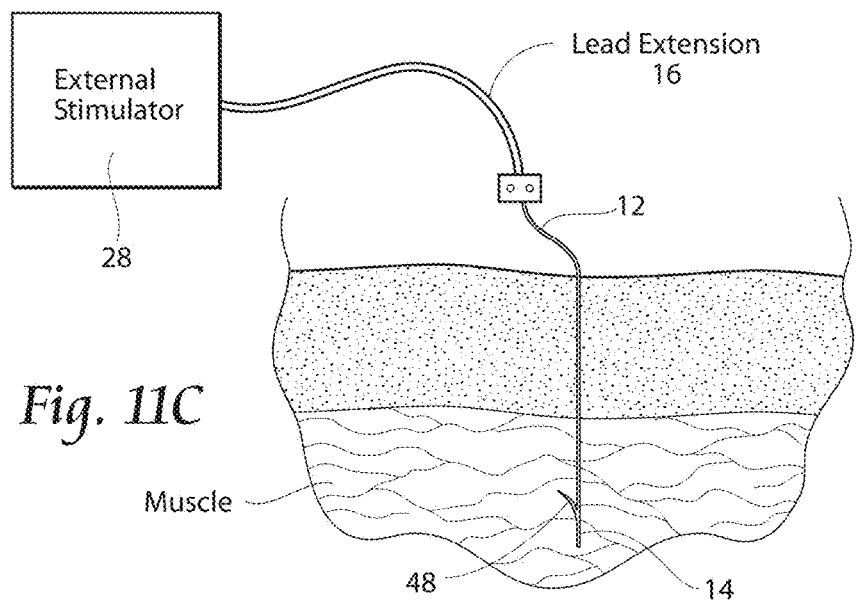

As FIG. 11A shows, the electrode lead can comprise, e.g., a fine wire electrode 14, paddle electrode, intramuscular electrode, or general-purpose electrode, inserted via a needle introducer 30 or surgically implanted in proximity of a targeted nerve of passage. Once proper placement is confirmed, the needle introducer 30 may be withdrawn (as FIGS. 11B and 11C show), leaving the electrode in place. Stimulation may also be applied through a penetrating electrode, such as an electrode array comprised of any number (i.e., one or more) of needle-like electrodes that are inserted into the target site. In both cases, the lead may placed using a needle-like introducer 30, allowing the lead/ electrode placement to be minimally invasive, though surgical placement could also be utilized.

In a representative embodiment, the lead 12 comprises a thin, flexible component made of a metal and/or polymer material. By "thin," it is preferred that the lead may be approximately 0.75 mm (0.030 inch) or less in diameter.

The lead 12 may comprise one or more conductors, e.g., one or more coiled metal wires, disposed within an open or flexible elastomer core. The wire can be insulated, e.g., with a biocompatible polymer film, such as polyfluorocarbon, polyimide, or parylene. The lead is desirably coated with a textured, bacteriostatic material, which helps to stabilize the lead in a way that still permits easy removal at a later date and increases tolerance.

The lead 12 may be electrically insulated everywhere except at one (monopolar), or two (bipolar), or three (tripolar) or more, for example, conduction locations near its distal tip. Each of the conduction locations may be connected to one or more conductors that run the length of the lead and lead extension 16 (see FIG. 11C), proving electrical continuity from the conduction location through the lead 12 to an external pulse generator or stimulator 28 (see FIG. 11C) or an implanted pulse generator or stimulator 28 (see FIG. 11D).

The conduction location or electrode 14 may comprise a de-insulated area of an otherwise insulated conductor that runs the length of an entirely insulated electrode. The de-insulated conduction region of the conductor can be formed differently, e.g., it can be wound with a different pitch, or wound with a larger or smaller diameter, or molded to a different dimension. The conduction location or the electrode 14 may comprise a separate material (e.g., metal or a conductive polymer) exposed to the body tissue to which the conductor of the wire is electrically coupled.

Figure 12:
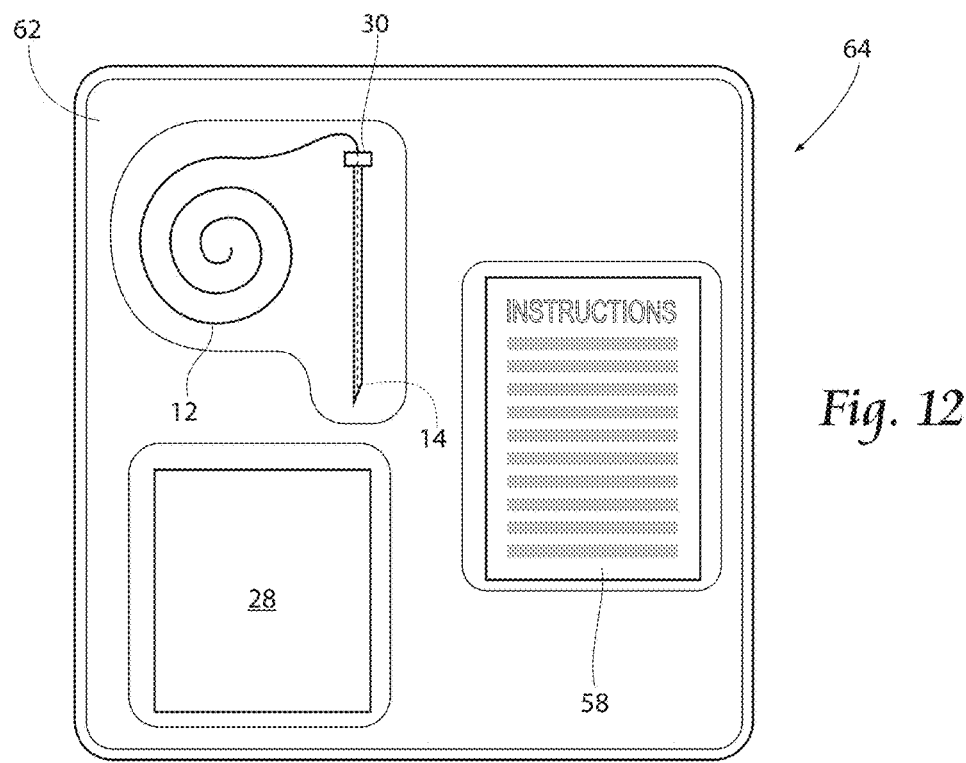
FIG. 12 is a view of a package containing a nerve of passage stimulation system.

The lead 12 is desirably provided in a sterile package 62 (see FIG. 12), and may be pre-loaded in the introducer needle 30. The package 62 can take various forms and the arrangement and contents of the package 62. As shown in FIG. 12, the package 62 comprises a sterile, wrapped assembly. The package 62 includes an interior tray made, e.g., from die cut cardboard, plastic sheet, or thermo-formed plastic material, which hold the contents. The package 62 also desirably includes instructions for use 58 for using the contents of the package to carry out the lead location and placement procedures, as will be described inb greater detail below.

The lead 12 desirably possess mechanical properties in terms of flexibility and fatigue life that provide an operating life free of mechanical and/or electrical failure, taking into account the dynamics of the surrounding tissue (i.e., stretching, bending, pushing, pulling, crushing, etc.). The material of the electrode 14 desirably discourages the in-growth of connective tissue along its length, so as not to inhibit its withdrawal at the end of its use. However, it may be desirable to encourage the in-growth of connective tissue at the distal tip of the electrode, to enhance its anchoring in tissue.

Figure 13A:
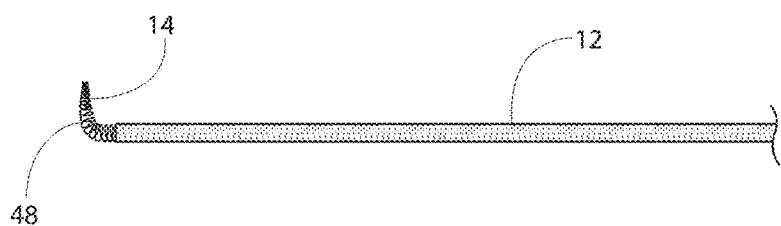
FIGS. 13A/B and 14A/B are representative leads that can form a part of a nerve of passage stimulation system.
Figure 13B:
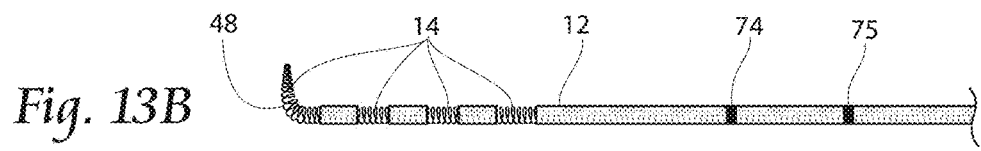

One embodiment of the lead 12 shown in FIG. 13A may comprise a minimally invasive coiled fine wire lead 12 and electrode 14. The electrode 14 may also include, at its distal tip, an anchoring element 48. In the illustrated embodiment, the anchoring element 48 takes the form of a simple barb or bend (see also FIG. 11C). The anchoring element 48 is sized and configured so that, when in contact with tissue, it takes purchase in tissue, to resist dislodgement or migration of the electrode out of the correct location in the surrounding tissue. Desirably, the anchoring element 48 is prevented from fully engaging body tissue until after the electrode 14 has been correctly located and deployed.

Figure 14A:
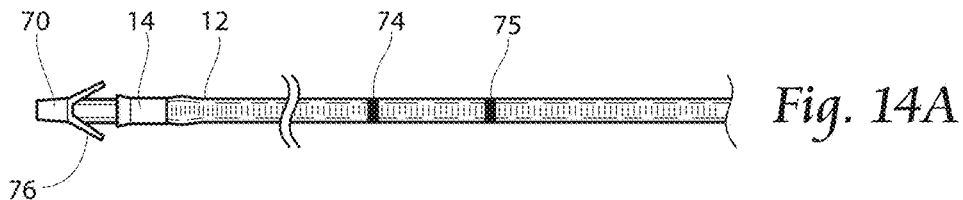
Figure 14B:
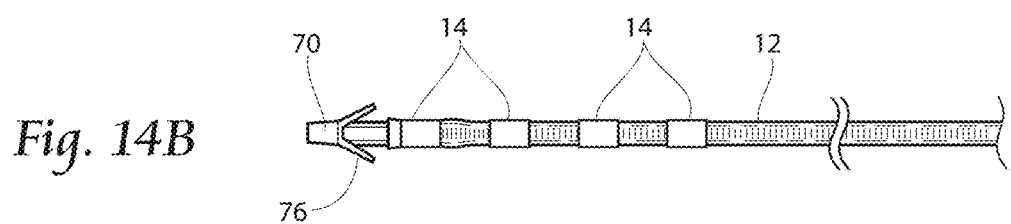

An alternative embodiment of an electrode lead 12 shown in FIGS. 14A and 14B, may also include, at or near its distal tip or region, one or more anchoring element(s) 70. In the illustrated embodiment, the anchoring element 70 takes the form of an array of shovel-like paddles or scallops 76 proximal to the proximal-most electrode 14 (although a paddle 76 or paddles could also be proximal to the distal most electrode 14, or could also be distal to the distal most electrode 14). The paddles 76 as shown are sized and configured so they will not cut or score the surrounding tissue. The anchoring element 70 is sized and configured so that, when in contact with tissue, it takes purchase in tissue, to resist dislodgement or migration of the electrode out of the correct location in the surrounding tissue (e.g., muscle 54). Desirably, the anchoring element 70 is prevented from fully engaging body tissue until after the electrode 14 has been deployed. The electrode is not deployed until after it has been correctly located during the implantation (lead placement) process, as previously described. In addition, the lead 12 may include one or more ink markings 74, 75 (shown in FIG. 14A) to aid the physician in its proper placement.

Alternatively, or in combination, stimulation may be applied through any type of nerve cuff (spiral, helical, cylindrical, book, flat interface nerve electrode (FINE), slowly closing FINE, etc.), paddle (or paddle-style) electrode lead, cylindrical electrode lead, and/or other lead that is surgically or percutaneously placed within tissue at the target site.

Figure 11D:
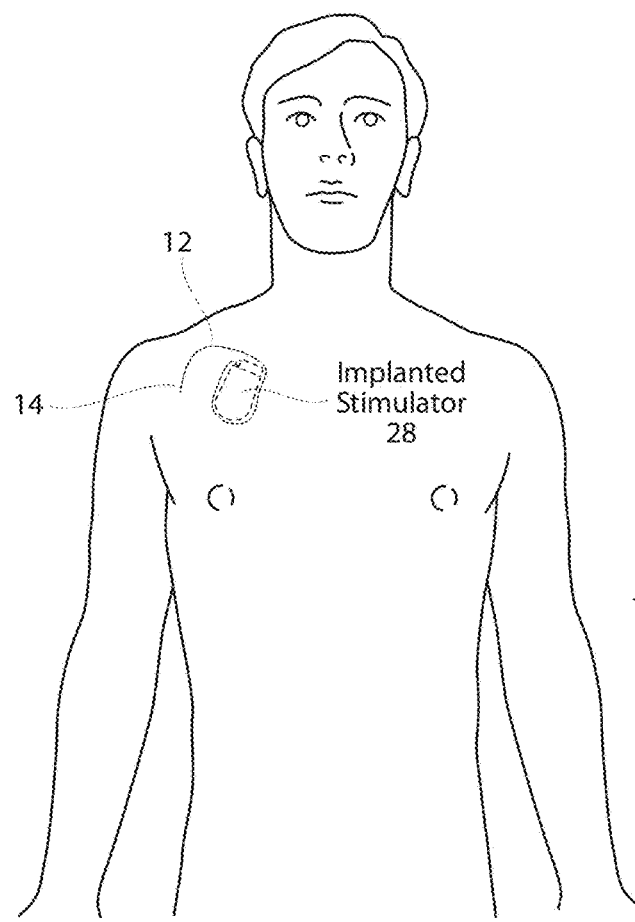

In all cases, the lead may exit through the skin and connect with one or more external stimulators 28 (shown in FIG. 11C), or the lead(s) may be routed subcutaneously to one or more implanted pulse generators 28 (shown in FIG. 11D), or they may be connected as needed to internal and external coils for RF (Radio Frequency) wireless telemetry communications or an inductively coupled telemetry to control the implanted pulse generator. As shown in FIG. 11D, the implanted pulse generator 28 may be located some distance (remote) from the electrode 14, or an implanted pulse generator may be integrated with an electrode(s) (not shown), eliminating the need to route the lead subcutaneously to the implanted pulse generator.

The introducer 30 (see FIG. 11A) may be insulated along the length of the shaft, except for those areas that correspond with the exposed conduction surfaces of the electrode 14 housed inside the introducer 30. These surfaces on the outside of the introducer 30 are electrically isolated from each other and from the shaft of the introducer 30. These surfaces may be electrically connected to a connector 64 at the end of the introducer body (see FIG. 11A). This allows connection to an external stimulator 28 (shown in FIG. 11A) during the implantation process. Applying stimulating current through the outside surfaces of the introducer 30 provides a close approximation to the response that the electrode 14 will provide when it is deployed at the current location of the introducer 30.

The introducer 30 may be sized and configured to be bent by hand prior to its insertion through the skin. This will allow the physician to place lead 12 in a location that is not in an unobstructed straight line with the insertion site. The construction and materials of the introducer 30 allow bending without interfering with the deployment of the lead 12 and withdrawal of the introducer 30, leaving the lead 12 in the tissue.

C. Insertion of the Lead

Representative lead insertion techniques will now be described to place an electrode lead 12 in a desired location in muscle in electrical proximity to but spaced away from a nerve of passage. It is this lead placement that makes possible the stimulation of the targeted nerve or nerves of passage with a single lead 12 to provide pain relief.

Instructions for use 58 (see FIG. 12) can direct use of system and method for the placement of a lead 12 in muscle in electrical proximity to but spaced away from the nerve or nerves of passage for improved recruitment of target nerves, e.g., with the placement of one or more leads 12. The instructions for use may include instructions for placing a lead 12 for the activation of the targeted nerve of passage in a system for the relief of pain, for example. The instructions for use may also include instructions for recording stimulus parameters, including intensity associated with a first sensation of stimulation, a first noticeable muscle contraction, and/or a maximum tolerable contraction at multiple locations, which can be used to aid in determining desired stimulation parameters for optimal stimulation.

The instructions 58 can, of course vary. The instructions 58 may be physically present in a kits holding the lead 12 (as FIG. 12 shows), but can also be supplied separately. The instructions 58 can be embodied in separate instruction manuals, or in video or audio tapes, CD's, and DVD's. The instructions 58 for use can also be available through an internet web page.

To determine the optimal placement for the lead 12, test stimulation may be delivered through needle electrodes, and muscle responses may be observed. The motor point(s) of the target muscle(s) may be located first in order to confirm that the muscles are innervated. Needle electrodes may be used because they can be easily repositioned until the optimal location to deliver stimulation is determined.

At least one electrode may be placed in muscle tissue at a therapeutically effective distance spaced from a targeted nerve of passage. By a "therapeutically effective distance" is meant that the electrode is not placed against the targeted nerve of passage, but rather spaced therefrom, electrically coupled to the nerve through other bodily tissue. The spacing is advantageous because it simplifies placement and stimulation procedures, reduces the risk of neurological injury to the patient, shortens the procedure time, makes the method of pain relief more robust and durable and less likely to fail or lose effectiveness over time. Such placement also allows the electrode to be placed in tissue more resistant to electrode migration or unwanted movement and more tolerant of motion and short and/or long-term changes in electrode position relative to the targeted nerve. The lead may be inserted via the introducer 30 in conventional fashion, which may be similar in size and shape to a hypodermic needle. The introducer 30 may be any size. In a preferred embodiment, the introducer 30 may range in size from 17 gauge to 26 gauge. Prior to inserting the introducer 30, the insertion site may be cleaned with a disinfectant (e.g. Betadine, 2% Chlorhexidine/80% alcohol, 10% povidone-iodine, or similar agent). A local anesthetic(s) may be administered topically and/or subcutaneously to the area in which the electrode and/or introducer will be inserted.

The position of the electrodes may be checked by imaging techniques, such as ultrasound, fluoroscopy, or X-rays. Following placement of the lead(s), the portion of the leads which exit the skin may be secured to the skin using covering bandages and/or adhesives.

Electrical stimulation may be applied to the targeted nerve of passage during and after placement of the electrode to determine whether stimulation of the targeted nerve of passage can generate comfortable sensations or paresthesias that overlap with the region of pain and/or reduce pain. The pain may be perceived to be contained within a specific part(s) of the body and/or it may be perceived to be located outside of the body, as may be the case in persons with amputations who have phantom limb pain or pain in the amputated (or phantom) limb(s).

In a percutaneous system 10 (as FIGS. 11A to 11D show, the lead 12 may be percutaneously placed near the targeted nerve of passage and exit at a skin puncture site 16. A trial or screening test may be conducted in a clinical setting (e.g. an office of a clinician, a laboratory, a procedure room, an operating room, etc.). During the trial, the lead is coupled to an external pulse generator 28 and temporary percutaneous and/or surface return electrodes, to confirm paresthesia coverage and/or pain relief of the painful areas.

If the clinical screening test is successful, the patient may proceed to a home-trial coupled to an external pulse generator 28 (as shown in FIG. 11C) and temporary percutaneous and/or surface return electrodes, to determine if pain relief can be sustained in the home environment. The trial period may range from minutes to hours to days to weeks to months. The preferred trial period may be between 3 and 21 days.

If either the screening test or home trial is unsuccessful, the lead 12 may be quickly and easily removed.

However, if the screening test and/or home-trial are successful, the patient's percutaneous system may be converted into a fully implanted system (as shown in FIG. 11D) by replacing the external pulse generator with an implantable pulse generator 28 (the housing of which serves as a return electrode).

Alternatively, it may be preferred to use a percutaneous system(s) as a therapy without proceeding to a fully implantable system. It is also to be appreciated that a home-trial is not a requirement for either the percutaneous system or a fully implanted system.

The duration of therapy for a percutaneous system may range from minutes to days to weeks to months to multiple years, but a preferred embodiment includes a duration ranging from 1 to 12 weeks.

Electrical stimulation is applied between the lead and return electrodes (uni-polar mode). Regulated current is the preferred type of stimulation, but other type(s) of stimulation (e.g. non-regulated current such as voltage-regulated) may also be used. Multiple types of electrodes may be used, such as surface, percutaneous, and/or implantable electrodes. The surface electrodes may be a standard shape or they may be tailored if needed to fit the contour of the skin.

In a preferred embodiment of a percutaneous system, the surface electrode(s) may serve as the anode(s) (or return electrode(s)), but the surface electrode(s) may be used as the cathode(s) (active electrode(s)) if necessary. When serving as a return electrod(e), the location of the electrode(s) is not critical and may be positioned anywhere in the general vicinity, provided that the current path does not cross the heart. If a surface electrode(s) serves as an active electrode(s), it (they) may be positioned near the target stimulation area(s) (e.g. on the skin surface over the target nerve or passage).

The electrode lead may be placed via multiple types of approaches. In one embodiment, the approach may be similar to needle placement for electromyography (EMG).

Figure 15A:
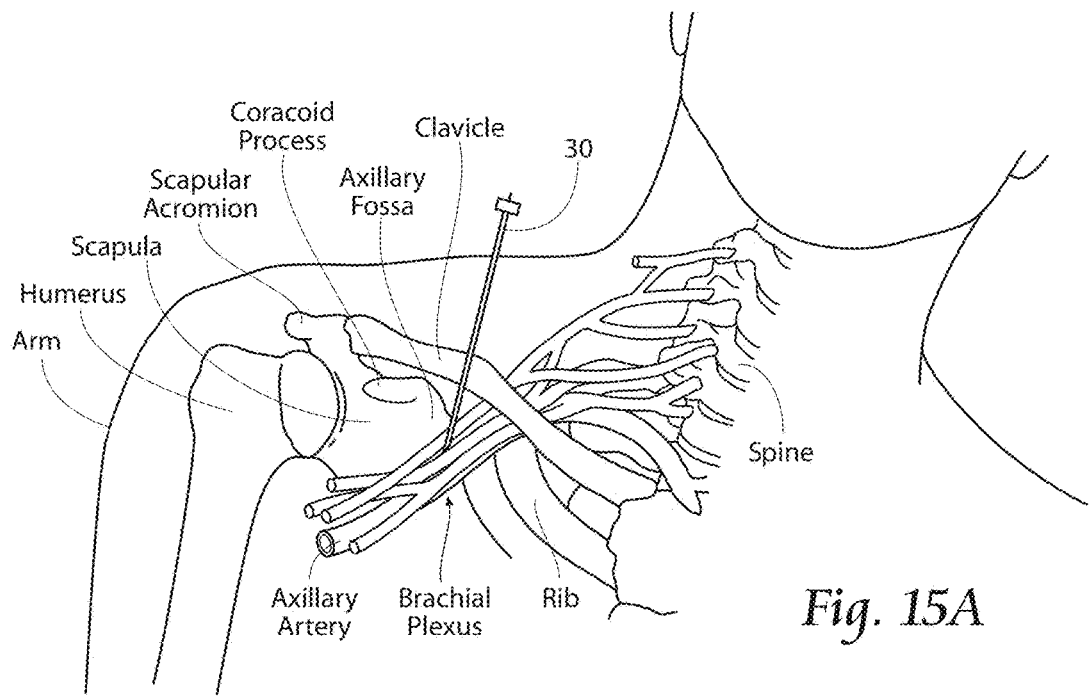
FIGS. 15A and 15B are schematic anatomic views of a system for applying nerve of passage stimulation to spinal nerves in the brachial plexus.

For example (as shown in FIG. 15A), if the targeted nerve of passage includes nerves of the brachial plexus, the approach can include:

1) Place the patient in a comfortable and/or appropriate position with head turned away from the lead insertion site.

2) Prepare the lead insertion site with antiseptic and local subcutaneous anesthetic (e.g., 2% lidocaine).

3) Locate the site of skin puncture with appropriate landmarks, such as the clavical, coracoid process, and axilla, as necessary.

4) Insert a sterile percutaneous electrode lead 12 preloaded in the introducer needle 30 at a predetermined angle based on landmarks used.

5) Place a surface stimulation return electrode in proximity of the area in which the percutaneous lead 12 has been placed. Test stimulation will be applied to the lead 12, with the surface electrode providing a return path. The surface electrode may be placed adjacent to the lead. Its position is not critical to the therapy and it can be moved throughout the therapy to reduce the risk of skin irritation.

6) Couple the lead 12 to the external pulse generator 28 and to the return electrode. Set the desired stimulation parameters. Test stimulation may be delivered using a current-regulated pulse generator, for example. The external pulse generator 28 may be programmed to about 0.1 to about 10 milliamps (mA), a pulse duration or width of about five to about fifty microseconds (v), a pulse frequency of about four to about 300 Hertz (Hz), and a preferred on-off duty cycle of about 25 to about 90 percent (on vs. off), as a non-limiting example. Alternatively, rather than have an on-off duty cycle, the stimulation can be delivered constantly for a predetermined treatment time, such as about two to six weeks.

7) Advance the introducer slowly until the patient reports the first evoked sensation in the region experiencing pain. Progressively reduce the stimulus amplitude and advance the introducer more slowly until the sensation can be evoked in the painful region at a predetermined stimulus amplitude (e.g., about 0.1-5.0 mA). Stop the advancement of the introducer, and increase the stimulus amplitude in small increments (e.g., about 0.1-0.5 mA) until the stimulation-evoked tingling sensation (paresthesia) expands to overlay the entire region of pain.

Figure 15B:
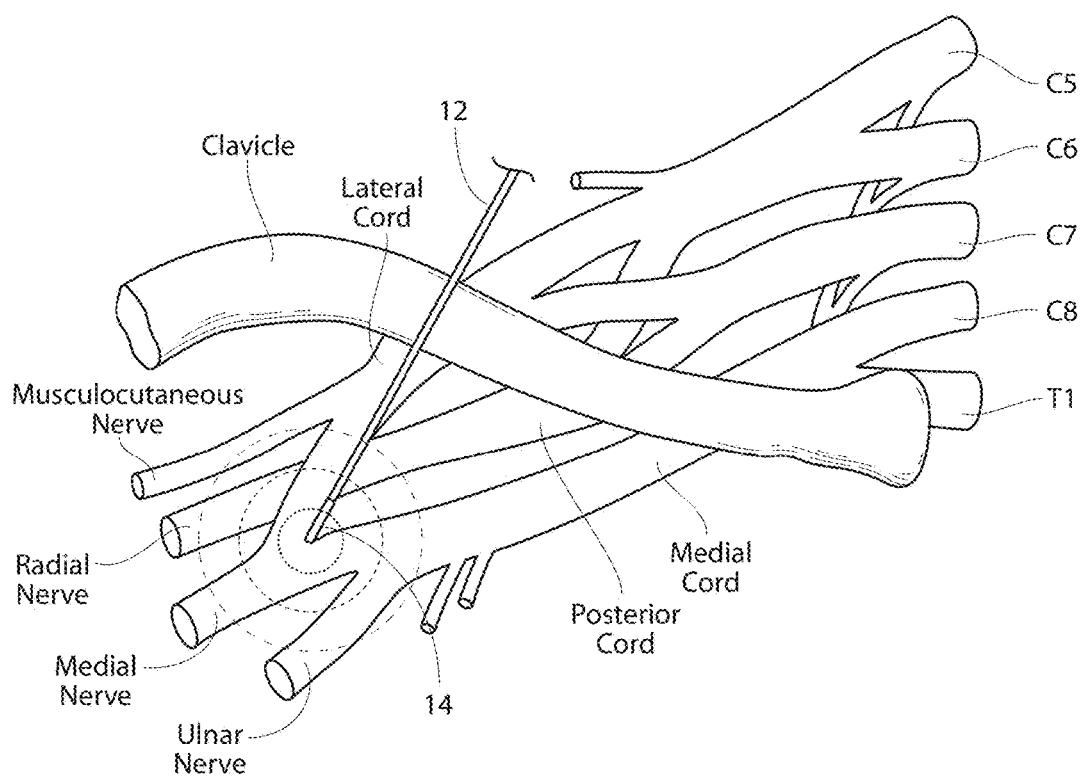

8) Withdraw the introducer 30, leaving the percutaneous lead 12 in proximity but away from the target nerve (see FIG. 15B).

9) Cover the percutaneous exit site and lead 12 with a bandage. A bandage may also be used to secure the external portion of the lead 12 (or an extension cable used to couple the lead 12 to the external pulse generator) to the skin. It is expected the length of time to place the lead 12 to be less than 10 minutes, although the process may be shorter or longer.

10) Vary the stimulus amplitude in small steps (e.g., 0.1-0.5 mA) to determine the thresholds at which stimulation evokes first sensation ($T_{SEN}$), sensation (paresthesia) superimposed on the region of pain ($T_{SUP}$), muscle twitch ($T_{MUS}$) of the target muscle (innervated or not innervated by the target nerve), and/or maximum comfortable sensation ($T_{MAX}$). Query the patient at each stimulus amplitude to determine sensation level, and visually monitor muscle response. Record the results.

11) It is possible that stimulation intensity may need to be increased slightly during the process due to causes such as habituation or the patient becoming accustomed to sensation, but the need for increased intensity is unlikely and usually only occurs after several days to weeks to months as the tissue encapsulates and the patient accommodates to stimulation. It is to be appreciated that the need for increased intensity could happen at any time, even years out, which would likely be due to either lead migration or habituation, but may also be due reasons ranging from nerve damage to plasticity/reorganization in the central nervous system.

12) If paresthesias cannot be evoked with the initial lead placement, redirect the introducer 30.

13) If sensations still cannot be evoked in a given patient, then the muscle twitch response of the muscle innervated or not innervated by the target nerve may be used to guide lead placement and then increase stimulus intensity until sufficient paresthesias are elicited in the painful region. Minimal muscle contraction may be acceptable if it is well tolerated by the patient in exchange for significant pain relief and if it does not lead to additional discomfort or fatigue.

14) If stimulation evokes muscle contraction at a lower stimulus threshold than paresthesia (e.g. if $T_{MUS} \leq T_{SUP}$p) and contraction leads to discomfort, then a lower stimulus frequency (e.g., 12 Hz) may be used because low frequencies (e.g., 4-20 Hz) have been shown to minimize discomfort due to muscle contraction and provide >50% relief of shoulder pain in stroke patients while still inhibiting transmission of pain signals in the central nervous system in animals. If continued muscle contraction leads to pain due to fatigue, change the duty cycle, using parameters shown to reduce muscle fatigue and related discomfort in the upper extremity (e.g. 5 s ramp up, 10 s on, 5 s ramp down, 10 s off).

15) If stimulation fails to elicit paresthesia in all areas of pain, then a second percutaneous lead (not shown) may need to be placed to stimulate the nerves that are not activated by the first lead 12.

16) If stimulation is successful, i.e., if the screening test and/or home-trial are successful, the patient's percutaneous system (see FIG. 1) may be converted into a fully implanted system by replacing the external pulse generator 28 with an implantable pulse generator that is implanted in a convenient area (see FIG. 11D) (e.g., in a subcutaneous pocket over the hip or in the subclavicular area). In one embodiment, the electrode lead 12 used in the screening test and/or home-trial may be totally removed and discarded, and a new completely implantable lead may be tunneled subcutaneously and coupled to the implantable pulse generator. In an alternative embodiment, a two part lead may be incorporated in the screening test and/or home-trial where the implantable part is completely under the skin and connected to a percutaneous connector (i.e., extension) that can be discarded after removal. The implantable part may then be tunneled and coupled to the implantable pulse generator, or a new sterile extension may be used to couple the lead to the implantable pulse generator.

Figure 17A:
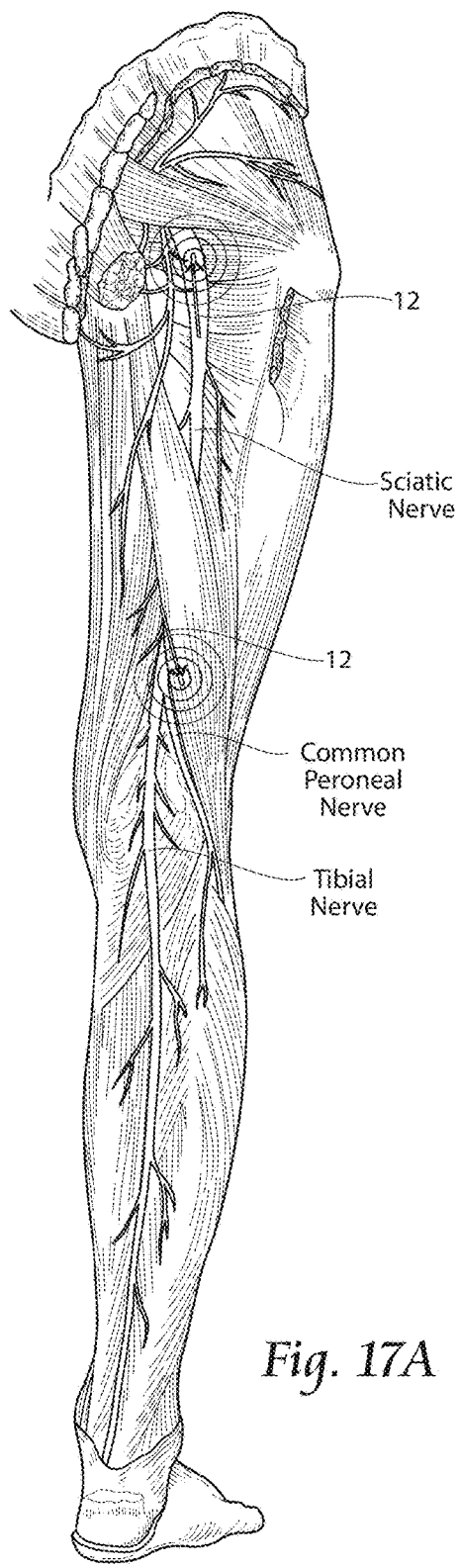
FIGS. 17A, 17B, and 17C are schematic anatomic views of a system for applying nerve of passage stimulation to a sciatic/tibial nerve.

Alternatively, when the targeted nerve of passage includes one or more nerves of the lumbar plexus or sacral plexus, the approach may be either a posterior (shown in FIG. 16A) or an anterior approach (shown in FIG. 17A), similar to those used for regional anesthesia of the same targeted nerve of passage, except that the approach is used for placement through an introducer of stimulation lead(s) or electrode(s) in electrical proximity to but spaced away from a nerve of passage, and not for chemically-induced regional anesthesia. Unlike regional anesthesia, the approach to nerves of the lumbar plexus or sacral plexus do not involve the application of anesthesia to the nerve, and, when the introducer is withdrawn, the lead(s) or electrode(s) may be left behind to provide the desired stimulation of the target nerve of passage.

Figure 18A:
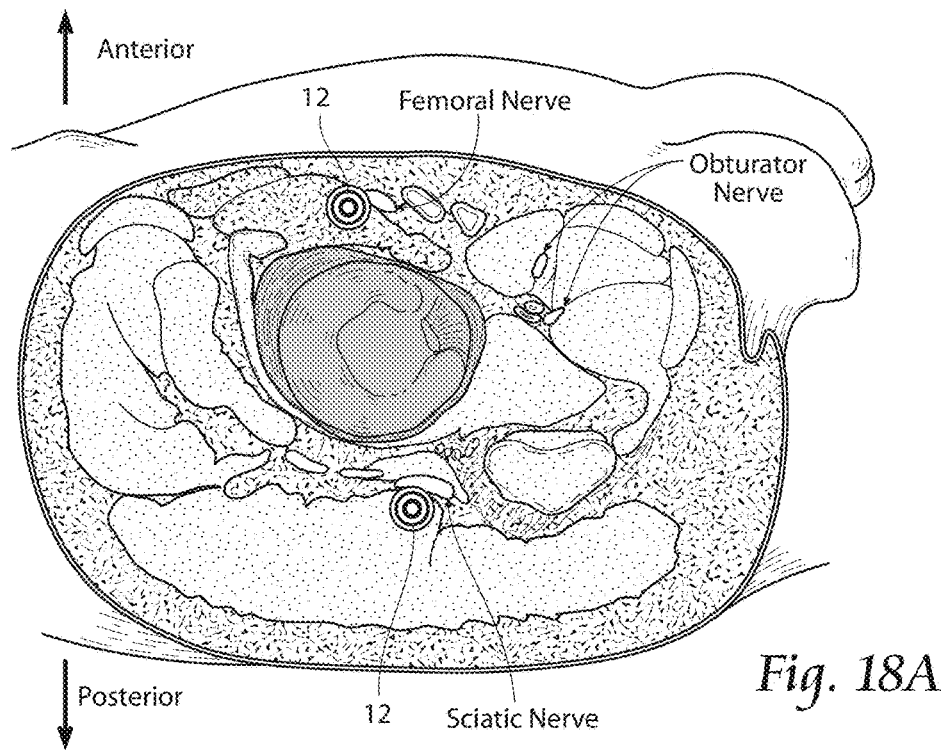
FIGS. 18A and 18B are schematic sectional anatomic views of systems for applying nerve of passage stimulation to a femoral nerve and a sciatic/tibial nerve.

For example, when the targeted nerve of passage includes the sciatic nerve (see FIG. 18A), the introducer(s) 30 and/or lead(s) 12 may be directed towards the sciatic nerve using a posterior approach, such as the transgluteal approach or subgluteal approach, which are both well described and commonly used in regional anesthesiology (Dalens et al. 1990; Bruelle et al. 1994; di Benedetto et al. 2001; Gaertner et al. 2007).

Alternatively, an adapted approach may also be used which is similar to approaches used in regional anesthesiology but may be adapted to minimize patient discomfort or damages or complications related to the therapy and/or system. As an example, the introducer(s) and/or lead(s) may be inserted from a more lateral insertion site (or another site that is more desirable) than is typically used for regional anesthesiology because it has been found that a more lateral (or other) insertion site minimizes patient discomfort. The insertion site and/or path may be adapted or an alternative insertion site and/or path may be selected with an understanding of the type of tissue, muscle and other tissue planes, compartments, innervation of the tissue, muscle orientation, muscle fiber directionality, vascular and/or lymphatic vessels and structures, and other considerations below, surrounding, or near the insertion site or path. As non-limiting examples, it may be desirable to minimize the number of muscle planes that are transversed or crossed with the introducer(s) and/or lead(s), or it may be desirable to use an insertion site and/or insertion path that is not densely innervated by non-target sensory nerve fibers, maximizing the comfort of the placement procedure and the therapy following removal of the introducer, or it may be desirable to orient the direction of the introducer(s) and/or lead(s) relative to the directionality of the muscle fibers, placing the lead(s) in line with (e.g. parallel to) or orthogonal to the muscle fibers or any variation between parallel or orthogonal to the muscle fibers.

This approach allows lead placement near a targeted nerve of passage with a simple, quick (e.g. less than 10 minutes) outpatient procedure that may be performed in a standard community-based clinic. This makes possible widespread use and provides a minimally-invasive screening test to determine if patients will benefit from the device before receiving a fully implanted system.

The landmarks for the transgluteal approach may include the greater trochanter and the posterior superior iliac spine. The introducer 30 may be inserted distal or proximal (e.g. approximately up to about 12 cm in a preferred embodiment) and/or medial or lateral (e.g. approximately up to about 12 cm in a preferred embodiment) to the midpoint between the greater trochanter and the posterior iliac spine. Alternatively, the introducer 30 may be inserted at the midpoint between the greater trochanter and the posterior iliac spine. As a non-limiting example of patient positioning, the patient may be in a lateral decubitus position and tilted slightly forward in a preferred embodiment.

The landmarks for the subgluteal approach may include the greater trochanter and the ischial tuberosity. The introducer may be inserted distal or proximal (e.g. approximately up to about 12 cm in a preferred embodiment) and/or medial or lateral (e.g. approximately up to about 12 cm in a preferred embodiment) to the midpoint between the greater trochanter and the ischial tuberosity. Alternatively, the introducer 30 may be inserted at the midpoint between the greater trochanter and the ischial tuberosity.

For any approach targeting the sciatic nerve (e.g. the transgluteal, subgluteal, and/or another or adapted approach), it may be beneficial to insert the introducer lateral to the midpoint between the relevant landmarks. A more lateral insertion point may maximize safety to the patient and/or the system, and it may increase patient comfort and minimize risk of damage to the lead or migration of the lead. As a non-limiting example of lateral placement, the introducer may be inserted lateral to the midpoint between the greater trochanter and the ischial tuberosity. The introducer may be inserted anywhere between the midpoint and the greater trochanter. The introducer may be inserted proximal or distal to the line between the greater trochanter and ischial tuberosity. It may be beneficial to insert the introducer distal to this line.

For example, when the targeted nerve of passage includes the femoral nerve (see FIG. 18A), percutaneous leads 12 may be directed towards the femoral nerve using an anterior approach. The landmarks may include the inguinal ligament, inguinal crease, and femoral artery. The patient may be in the supine position with ipsilateral extremity slightly (approximately 10 to 20 degrees) abducted. The introducer may be inserted near or below the femoral or inguinal crease and approximately 1 cm or more lateral to the pulse of the femoral artery. More detail on placement of a percutaneous lead 12 for stimulation of the femoral nerve may be found below.

The size and shape of tissues, such as the buttocks, surrounding the target nerves may vary across patients, and the approach may be modified as needed to accommodate various body sizes and shapes to access the target nerve.

In non-amputee patients, introducer placement can be often guided by muscle response to electrical stimulation, but the muscle response may not be available in amputees, or may not be available and/or be unreliable in other situations (e.g., a degenerative diseases or condition such as diabetes of impaired vascular function in which the nerves are slowly degenerating, progressing from the periphery, or due to trauma).

In these situations, placement may be guided by the individual's report of stimulus-evoked sensations (paresthesias) as the introducer is placed during test stimulation. Additionally, the response of remaining muscles to stimulation may also be used to guide placement of the introducer and electrode.

Figure 18B:
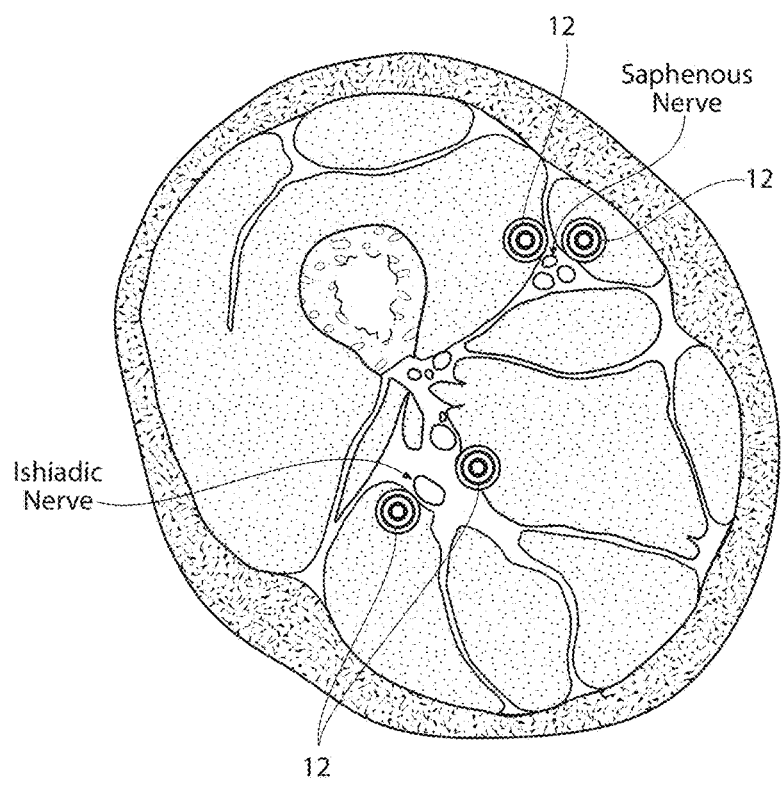

As shown in FIG. 18B, more than a single lead 12 may be placed around or in the vicinity of a given nerve of passage, using either an anterior approach (e.g., femoral nerve) or a posterior approach (e.g., sciatic nerve). As FIGS. 19A, B, and C show, one or more leads 12 can be placed at different superior-inferior postions along a nerve of passage and/or along different nerves of passage.

Figure 16B:
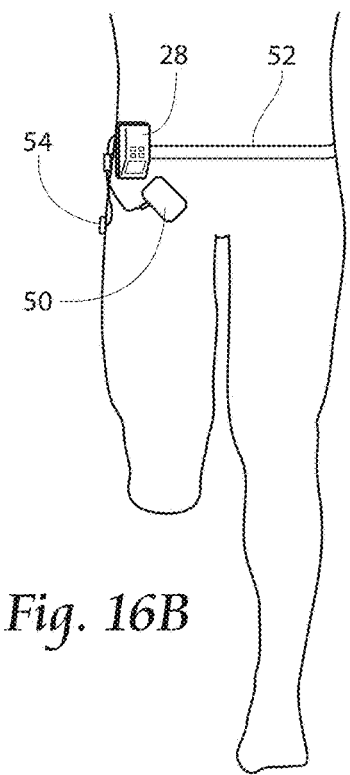
Figure 16C:
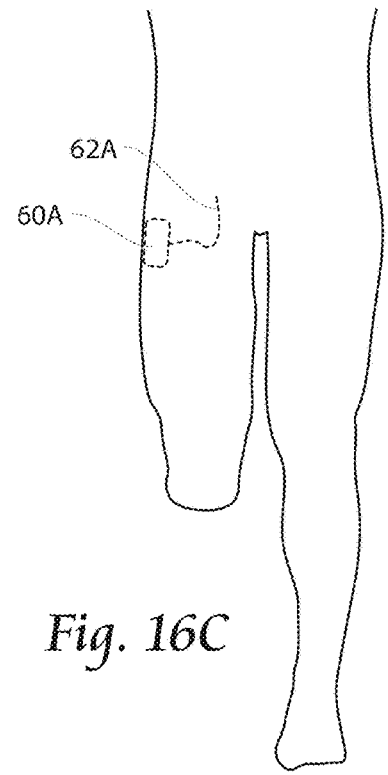
Figure 17B:
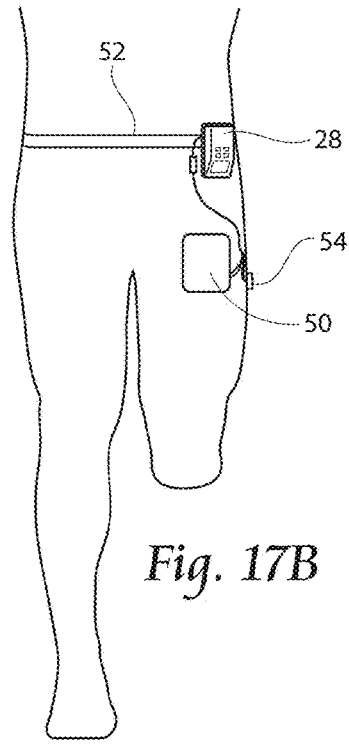
Figure 17C:
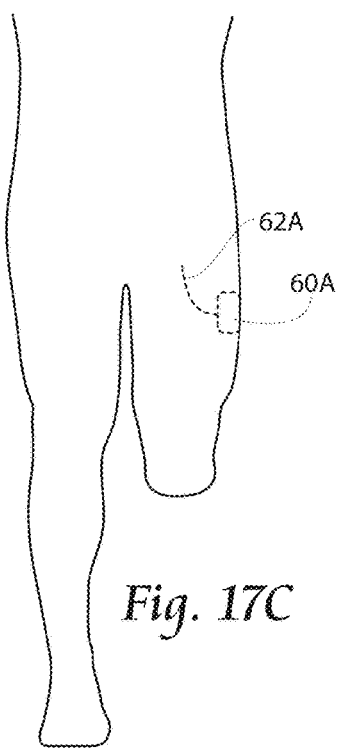

As FIG. 16B (anterior approach, e.g., femoral nerve) and 17B (posterior approach, e.g., sciatic nerve) show, the lead 12 can be coupled to an external pulse generator 28 worn, e.g., on a belt 52, for a trial or temporary stimulation regime. In this arrangement, the lead 12 is covered with a bandage 50, and a surface electrode 54 serves as a return electrode. The external/percutaneous system shown in FIGS. 16B and 17B may be replaced by an implanted system using an implanted pulse generator 60 and intramuscular and/or adipose and tunneled leads 62, as shown in FIGS. 16C and 17C, respectively. In this arrangement, the case of the implanted pulse generator 60A comprises the return electrode.

D. Stimulation Parameters

Control of the stimulator and stimulation parameters may be provided by one or more external controllers. In the case of an external stimulator, the controller may be integrated with the external stimulator. The implanted pulse generator external controller (i.e., clinical programmer) may be a remote unit that uses RF (Radio Frequency) wireless telemetry communications (rather than an inductively coupled telemetry) to control the implanted pulse generator. The external or implantable pulse generator may use passive charge recovery to generate the stimulation waveform, regulated voltage (e.g., 10 mV to 20 V), and/or regulated current (e.g., about 10 µA to about 50 mA). Passive charge recovery is one method of generating a biphasic, charge-balanced pulse as desired for tissue stimulation without severe side effects due to a DC component of the current.

The neurostimulation pulse may by monophasic, biphasic, and/or multi-phasic. In the case of the biphasic or multi-phasic pulse, the pulse may be symmetrical or asymmetrical. Its shape may be rectangular or exponential or a combination of rectangular and exponential waveforms. The pulse width of each phase may range between e.g., about 0.1 µsec. to about 1.0 sec., as non-limiting examples. The preferred neurostimulation waveform is cathodic stimulation (though anodic will work), biphasic, and asymmetrical.

Pulses may be applied in continuous or intermittent trains (i.e., the stimulus frequency changes as a function of time). In the case of intermittent pulses, the on/off duty cycle of pulses may be symmetrical or asymmetrical, and the duty cycle may be regular and repeatable from one intermittent burst to the next or the duty cycle of each set of bursts may vary in a random (or pseudo random) fashion. Varying the stimulus frequency and/or duty cycle may assist in warding off habituation because of the stimulus modulation.

The stimulating frequency may range from e.g., about 1 Hz to about 300 Hz, and the frequency of stimulation may be constant or varying. In the case of applying stimulation with varying frequencies, the frequencies may vary in a consistent and repeatable pattern or in a random (or pseudo random) fashion or a combination of repeatable and random patterns.

In a representative embodiment, the stimulator is set to an intensity (e.g. 0.1-20 mA (or 0.05-40 mA, or 0.01-200 mA), a pulse duration or width 1-300 µs (or 5-1000 µs, or 1-10,000 µs)) sufficient to activate the targeted nerve of passage at some therapeutically effective distance (e.g. 1 mm or more) away (from the targeted nerve of passage). If the stimulus intensity is too great, it may generate muscle twitch(es) or contraction(s) sufficient to disrupt correct placement of the lead. If stimulus intensity is too low, the lead may be advanced too close to the targeted nerve of passage (beyond the optimal position), possibly leading to incorrect guidance, nerve damage, mechanically evoked sensation (e.g. pain and/or paresthesia) and/or muscle contraction (i.e. when the lead touches the nerve of passage), inability to activate the target nerve fiber(s) without activating non-target nerve fiber(s), improper placement, and/or improper anchoring of the lead (e.g. the lead may be too close to the nerve and no longer able to anchor appropriately in the muscle tissue).

In a representative embodiment, the stimulator is set to a frequency (e.g. 0.5-12 Hz (or 0.1-20 Hz, or 0.05-40 Hz)) low enough to evoke visible muscle twitches (i.e. non-fused muscle contraction) and/or muscle contraction(s) of the targeted muscle(s) innervated by the target nerve of passage, but high enough that that the targeted nerve of passage will be activated before the lead is advanced beyond the optimal position.

As an alternative to using muscle twitch(es) or contraction(s) as indicator(s) of lead placement (distance from the nerve of passage to electrode contact), patient sensation could instead be used to indicate lead location relative to the targeted nerve of passage. Any combination of stimulus parameters that evoke sensation(s) may be used. Some stimulus parameters may evoke a more desirable response (e.g. more comfortable sensation, or a sensation that may be correlated with or specific to the specific target nerve fiber(s) within the targeted nerve of passage. As an example, higher frequencies (e.g. ≥12 Hz, or ≥4 Hz, or ≥0.1 Hz) may evoke sensation(s) or comfortable paresthesia(s) in the region(s) of pain or in alternate target region(s) (real or phantom) and though they may (or may not) also evoke muscle contraction(s), the muscle contraction(s) may not be noticeable (e.g. stimulus intensity may not be sufficient to evoke a contraction or a twitch from the present lead location or stimulus intensity may be sufficient to evoke contraction but the muscle contraction is fused (and no longer visually twitching), making it difficult to observe visually, unless EMG is used). To take advantage of both potential indicator responses (muscle twitch and patient sensation), higher frequencies may be applied intermittently (at lower frequencies), where the higher frequencies (e.g. 20-120 Hz, or 12-200 Hz) would normally caused fused muscle contraction if they were applied continuously but they are applied at an intermittent frequency (e.g. 0.5-4 Hz, or 0.1-11 Hz) that is low enough to allow the muscle to relax during the gaps between the bursts of stimulation, making it easier to visualize while still generating patient sensation at a higher frequency, allowing both muscle twitch and patient sensation to be used simultaneously as indicators of lead location relative to the targeted nerve of passage.

While stimulation is being applied, the lead (non-limiting examples of the lead could include a single or multi-contact electrode that is designed for temporary (percutaneous) or long-term (implant) use or a needle electrode (used for in-office testing only)) may be advanced (e.g. slowly advanced) towards the targeted nerve of passage until the desired indicator response (e.g. muscle twitch, muscle contraction, patient sensation, and/or some combination) is obtained at a first location X1. The intensity may then be decreased (e.g. gradually decreased) as the lead is advanced (e.g. advanced slowly) closer to the targeted nerve of passage until the desired indicator response(s) may be obtained at smaller intensity(ies) within the target range (e.g. 0.1-20 mA (or 0.09-39 mA, or 0.009-199 mA), 1-300 μs (or 5-1000 μs, or 1-10,000 μs)) at some distance (e.g. X2 mm, where X2<X1, and (as a non-limiting example) X1 may be multiple times larger than X2, such as X1≥2*X2, or X1≥5*X2, or X1≥20*X2) from the target nerve. If specific response(s) (e.g. desired response(s) and/or undesired response(s)) can be obtained at a range of intensities that are too low, then the lead may be located in a non-optimal location (e.g. too close to the target nerve(s)). Non-limiting examples of ranges of intensities that may be considered too low include those that are a fraction (e.g. <⅔, or <⅕, or <1/10) of the intensities that obtained the desired response(s) at X1.

Additionally or alternatively, preferably with stimulation turned off, a needle electrode (e.g., an EMG monitoring electrode connected to a stimulator) may be inserted a predetermined distance, such as approximately 0.1 to about 5.0 centimeters, and more preferably 0.5 to about 3.0 centimeters, from a target neural structure. The initial placement is preferably confirmed by the use of ultrasound imaging, including biological landmark identification. Such landmarks may include one or more of the femoral vein and/or femoral artery. Once inserted to an initial position, a test stimulation may be delivered by the needle electrode at a desired intensity (e.g., a pulse duration or width of about 5 to about 50 μs, a frequency of about 4 to about 200 Hz, and an amplitude of about 0.1 mA delivered constantly). If no neurological response is reported by the patient and no neurological response is observed or detected by the clinician, the amplitude of the test stimulation may be increased until a neurological response is reported, observed, or detected. A neurological response may be reported, observed, or detected at a location that is local to the stimulation delivery location (e.g. near the needle electrode). If a sensation is reported by the patient or a muscle contraction is observed at such location, the needle electrode may be too superficial and the electrode may be advanced further towards the target neural structure. In this case, the electrode is preferably advanced while the stimulation is turned off. Advancement may occur in the range of 0.1-2 cm, and the test stimulation process may be repeated. If a sensation is reported by the patient and the sensation is an uncomfortable sensation perceived to be originating at a point distal to the location of the electrode, or if a neurological response of muscle contraction is observed or detected as occurring distal to the electrode, it is an indication that the needle electrode is too close to the target neural structure, and the electrode is slightly withdrawn in the range of 0.1-2 cm while maintaining the needle electrode in vivo. During this slight withdrawal of the electrode, the stimulation is preferably off, and the test stimulation process may be repeated after electrode relocation. If in vivo readjustment or relocation of the electrode does not result in the goal of comfortable paresthesia in an area of pain, the needle electrode insertion trajectory and/or insertion site may be adjusted and the process repeated. Once an appropriate electrode location has been determined, the depth and trajectory is noted and used for guiding and/or informing the insertion of the treatment stimulation electrode to be anchored for a predetermined treatment duration.

The preferred stimulus intensities are a function of many variables, are meant to serve as non-limiting examples only, and may need to be scaled accordingly. As an example, if electrode shape, geometry, or surface area were to change, then the stimulus intensities may need to change appropriately. For example, if the intensities were calculated for a lead with an electrode surface area of approximately 20 mm², then they may need to be scaled down accordingly to be used with a lead with an electrode surface area of 0.2 mm² because a decrease in stimulating surface area may increase the current density, increasing the potential to activate excitable tissue (e.g. target and non-target nerve(s) and/or fiber(s)). Alternatively, if the intensities were calculated for a lead with an electrode surface area of approximately 0.2 mm², then the intensities may need to be scaled up accordingly to be used with a lead with an electrode surface area of 20 mm². Alternatively, stimulus intensities may need to be scaled to account for variations in electrode shape or geometry (between or among electrodes) to compensate for any resulting variations in current density. In a non-limiting example, the electrode contact surface area may be 0.1-20 mm², 0.01-40 mm², or 0.001-200 mm². In a non-limiting example, the electrode contact configuration may include one or more of the following characteristics: cylindrical, conical, spherical, hemispherical, circular, triangular, trapezoidal, raised (or elevated), depressed (or recessed), flat, and/or borders and/or contours that are continuous, intermittent (or interrupted), and/or undulating.

Stimulus intensities may need to be scaled to account for biological factors, including but not limited to patient body size, weight, mass, habitus, age, and/or neurological condition(s). As a non-limiting example, patients that are older, have a higher body-mass index (BMI), and/or neuropathy (e.g. due to diabetes) may need to have stimulus intensities scaled higher (or lower) accordingly.

As mentioned above, if the lead is too far away from the targeted nerve of passage, then stimulation may be unable to evoke the desired response (e.g. muscle contraction(s), comfortable sensation(s) (or paresthesia(s)), and/or pain relief) in the desired region(s) at the desired stimulus intensity(ies). If the lead is too close to the targeted nerve of passage, then stimulation may be unable to evoke the desired response(s) (e.g. muscle contraction(s), comfortable sensation(s) (or paresthesia(s)), and/or pain relief) in the desired region(s) at the desired stimulus intensity(ies) without evoking undesirable response(s) (e.g. unwanted and/or painful muscle contraction(s), sensation(s) (or paresthesia(s)), increase in pain, and/or generation of additional pain in related or unrelated area(s)). In some cases, it may difficult to locate the optimal lead placement (or distance from the targeted nerve of passage and/or it may be desirable to increase the range stimulus intensities that evoke the desired response(s) without evoking the undesired response(s) so alternative stimulus waveforms and/or combinations of leads and/or electrode contacts may be used. A non-limiting example of alternative stimulus waveforms may include the use of a pre-pulse to increase the excitability of the target fiber(s) and/or decrease the excitability of the non-target fiber(s).

Those skilled in the art will recognize that, for simplicity and clarity, the full structure and operation of all devices and processes suitable for use with the present invention is not being depicted or described herein. Instead, only so much of an implantable pulse generator and supporting hardware as is unique to the present invention or necessary for an understanding of the present invention is depicted and described. The remainder of the construction and operation of the IPGs described herein may conform to any of the various current implementations and practices known in the art.

III. Representative Indications for Chronic or Temporary Pain Therapy

Localized pain in any area of the body (e.g., the skin, bone, joint, or muscle) can be treated by applying electrical stimulation to tissue (e.g. muscle, adipose, connective or other tissue) in electrical contact with but spaced from a targeted nerve of passage. Electrical stimulation of nerves of passage works by interfering with or blocking pain signals from reaching the brain, as FIG. 10 schematically shows.

Many pain indications can be treated by nerves of passage stimulation.

Pain in the leg may occur in areas such as the thigh, calf, hip, shin, knee, foot, ankle, and toes. There may be multiple causes of leg pain, including but not limited to injury (e.g. traumatic) to a muscle, joint, tendon, ligament or bone; muscle or ligament damage; ligament sprain, muscle or tendon strain; disease or disorders; phlebitis, swelling, or inflammation; claudication; insufficient blood flow into (arterial insufficiency) or away from (venous insufficiency) a part of the leg or foot; ischemia; peripheral artery disease; arthritis; tumor (malignant or benign); peripheral neuropathy; diabetic peripheral neuropathy; and post herpetic neuralgia.

For example, peripheral artery disease can cause pain (especially during activity such as walking or running) because the effective narrowing of the arteries leads to a decrease in the supply of blood and therefore in the supply of nutrients such as oxygen to the active muscles, leading to pain. This phenomenon can occur in almost in area of the body but may be more common in the leg, especially parts of the lower leg, such as the calf. Activity is not always required to elicit pain and pain may occur even at rest (without activity or exercise). Nerve entrapment, compression, injury or other types of damage may cause pain in the areas innervated by the damaged nerve, which can lead to referred pain in an area distal to the injury.

For example, claudication pain (occurring in the calf muscle) could be treated by nerves of passage stimulation by placing the lead in the gluteus muscle near the sciatic nerve, which passes by the gluteus muscle on its way to innervate the calf muscle.

In general pain due to poor blood flow to an area or damage to an area can be relieved by stimulation of the nerve innervating that area. Since diabetic neuropathy typically leads to pain in the more distal areas (toes/foot), stimulation of the sciatic nerve can relive that pain. Pain in the skin of the medial (inner) calf can be relieved by stimulation of the femoral nerve. Pain in the front of the thigh (quad's) can be relieved by stimulation of the femoral nerve. If pain overlaps more than one area, stimulation of multiple nerves (e.g., sciatic and femoral nerves) can be beneficial.

Stimulation of the intercostal nerves (originating from the Thoracic nerve roots (T1-12)) can relieve pain in regions innervated by the intercostal nerves such as pain from intercostal neuralgia or post herpetic neuralgia. The pain may be confined to the area (e.g. dermatomic area) innervated by 1 or 2 nerves and may follow outbreak (and recovery) of herpes zoster. The pain may last up to several months or years in some patients and may be caused by nerve irritation or damage due to herpes zoster.

Post-amputation (e.g. including residual limb and/or phantom limb) pain can also be treated by nerves of passage stimulation. For example, upper extremity stimulation of spinal nerves passing through the brachial plexus can relive residual limb pain and/or phantom limb pain that results from amputation of an upper limb. Likewise, lower extremity stimulation of spinal nerves passing through the lumber plexus sacral plexus (e.g., the sciatic nerve or the femoral nerve) can relive residual limb pain and/or phantom limb pain that results from amputation of a lower limb.

Figure 23A:
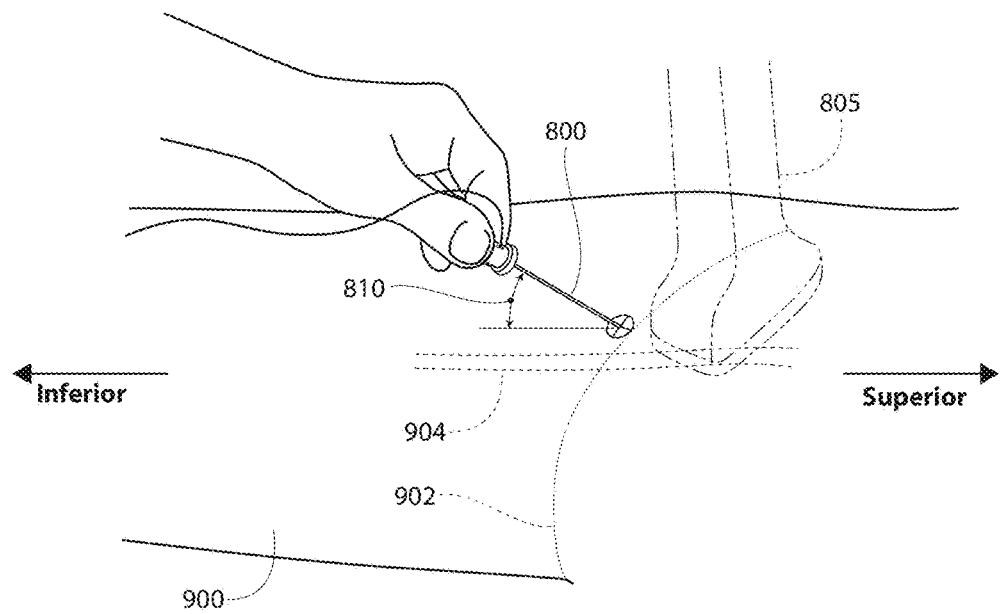
FIG. 23A is a perspective view of an EMG needle insertion towards a human femoral nerve.
Figure 23B:
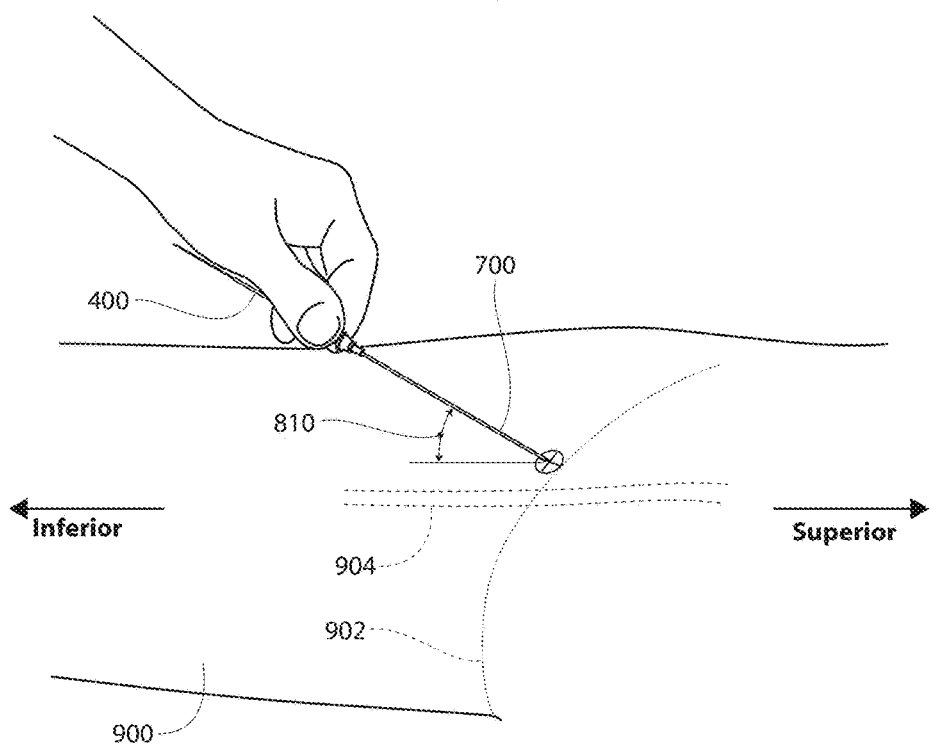
FIG. 23B is a perspective view of an insertion of the embodiment of FIG. 22 towards a human femoral nerve.

In one case study performed according to the present invention, in the treatment of post-amputation pain, the patient was a 49 year old African-American male who complained of severe residual limb pain (RLP) secondary to a below-the-knee amputation of his right leg (900 in FIGS. 23A and 23B) following a motor vehicle accident 33 years prior to enrollment into the study. The patient reported that the RLP remained severe despite a history of using narcotic analgesics, anticonvulsants, non-steroidal anti-inflammatory drugs (NSAIDs), physical therapy, and nerve blocks.

Inclusion criteria for enrollment in the case study included a well healed unilateral lower extremity amputation, residual limb pain and/or phantom limb pain score ≥4 on an 11-point numerical rating scale on the Brief Pain Inventory-Short Form (BPI-SF) Question #3 (BPI3), Beck Depression Inventory (BDI) score of ≤20 and age ≥18 years. Exclusion criteria included the absence of sepsis, infection; diabetes mellitus type I and II, implanted electronic devices, anticoagulation therapy (aside from aspirin therapy), history of valvular heart disease, pregnancy and any previous allergy to skin contact materials and or anesthetic agents. Also consistent with the exclusion criteria, the patient had not had a botulinum toxin injection within the last 6 months in the affected limb, had not had a steroid injection within the last 6 weeks in the affected limb, and had not participated in any drug or device trial in the past 30 days.

The patient was provided with a diary and asked to record medication usage and worst-pain levels every day for the duration of the 8-week study. Throughout the study, the patient reported taking the following medications daily: one multivitamin (1 time/day), ibuprofen (800 mg, 3 times/day), and gabapentin (600-800 mg, 3 times/day). At the end of a 2-week baseline period, the patient requested that his dose of gabapentin be increased from 600 mg to 800 mg in response to a recent back injury unrelated to the study. The patient continued to take the 800 mg dose of gabapentin for the remaining 6 weeks of the study.

After completing the 2-week baseline period, the patient returned for electrical stimulation lead placement and electrical stimulation testing (Visit 2). The electrical lead was a fine-wire helical coil wound from a seven-strand, type 316L stainless steel wire with a single anchoring barb and a single electrode contact, such as that shown in FIG. 20.

Figure 20:
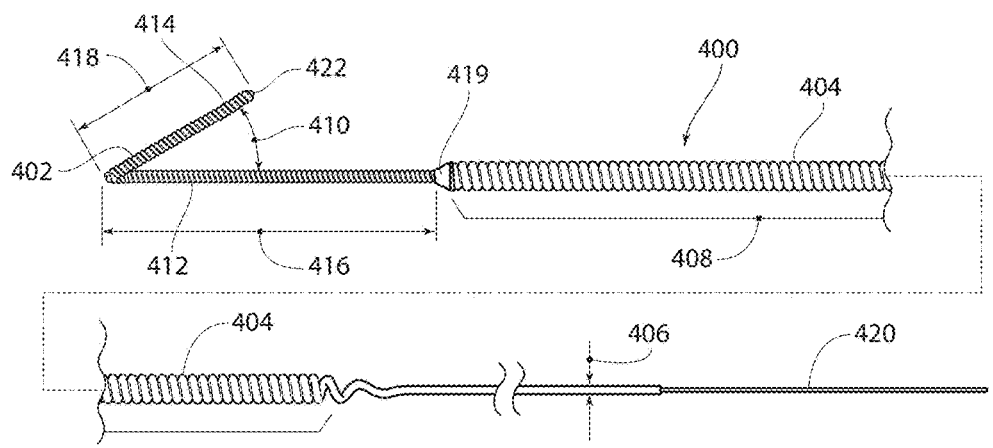
FIG. 20 is an elevation view of an embodiment of a percutaneous lead according to the present invention.

Turning now to FIG. 20, a preferred percutaneous lead 400 may be described. This lead 400 is a suitable lead 12 to be used as described herein. The lead 400 preferably includes an electrode 402 that extends from preferably an insulated conductor 404 having an insulated diameter 406 of about 10 mils. The insulated conductor 404 is preferably 4250 PFA coated 7-strand 316L stainless steel, which is preferably wound about a mandrel to form an insulated coiled portion 408 of a desired length, such as about seven to about nine inches. A portion of a distal end of the conductor 404 is stripped to form the electrode 402. The stripped portion is preferably coiled on a mandrel to an outside diameter of about 10 mils to about 15 mils, and then bent at an electrode angle 410 of about 20 degrees to about 70 degrees. The electrode 402 includes an extension 412 and a barb 414. The extension 412 has an electrode extension length 416 of about 350 mils to about 450 mils, and the barb 414 has a barb length 418 of about half that of the extension length 416, of about 160 mils to about 240 mils. At the juncture of the electrode 402 and the coiled insulated portion 408, a fillet of silicon adhesive 419, such as Nusil Med 1511, is preferably provided circumferentially about the lead 400. A test portion 420 of a proximal end of the lead 400 may also be stripped and tinned, and a maximum end-to-end resistance of the lead 400 is preferably about 150 ohms. Provided at a tip 422 of the barb 414 of the electrode 402 is preferably a weld to maintain the conductors of the lead 400 in a desired position. An electrically conductive path in which the lead 400 is used preferably has a maximum resistance of about 1300 ohms.

Figure 21:
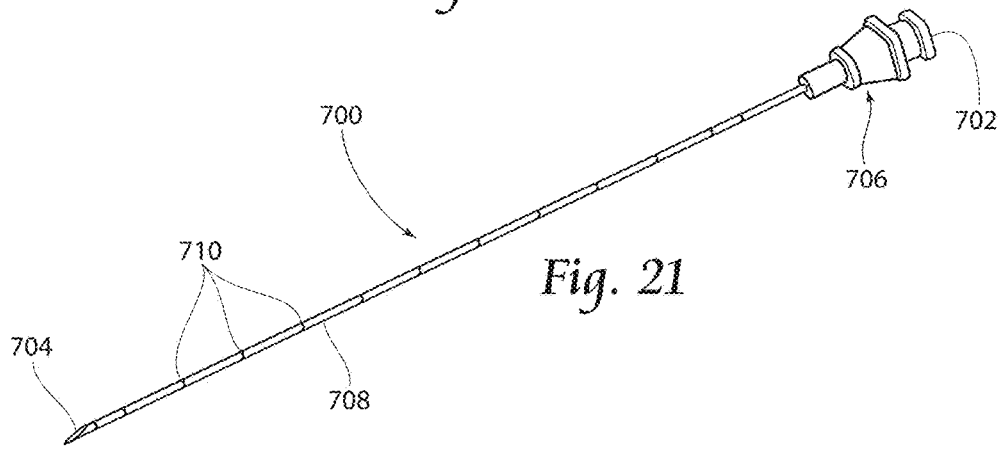
FIG. 21 is a perspective view of an introducer according to the present invention.
Figure 22:
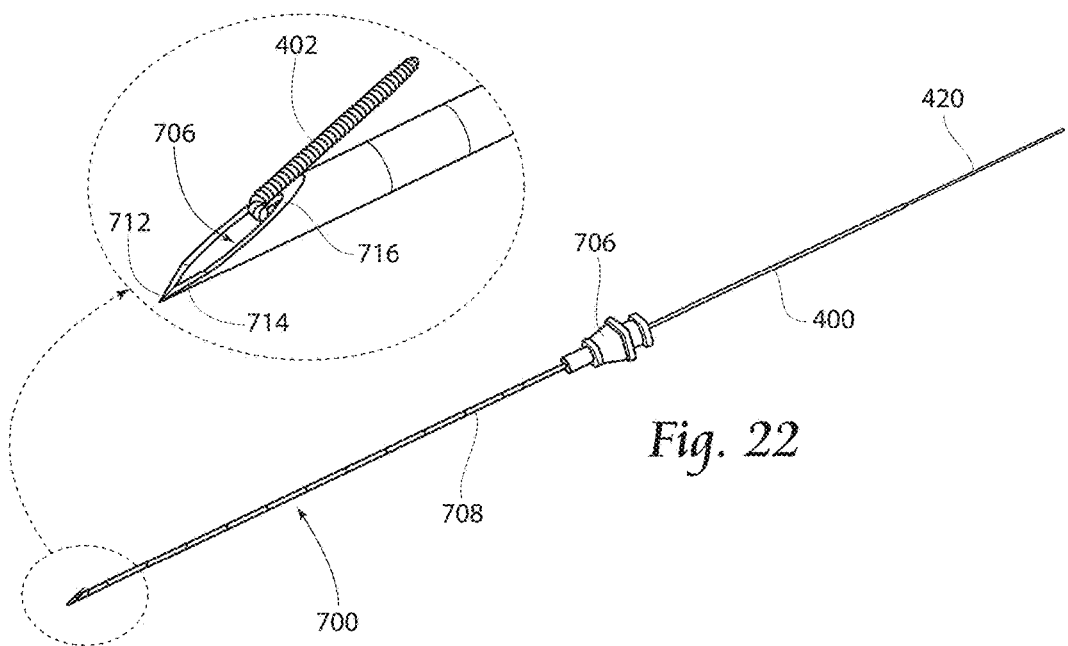
FIG. 22 is a perspective view of the introducer of FIG. 21 loaded with the lead of FIG. 20.

The lead 400 described may be used percutaneously, i.e. introduced and operatively extending through the epidermis of an animal, thus providing an insulated, electrically conductive path through such epidermis. To accomplish such introduction, a lead introducer 700 may be used, such as that shown in FIGS. 21-22. This introducer 700 is a suitable introducer 30 to be used as described herein. The introducer 700 extends from a proximal end 702 to a distal end 704, with a lumen 706 extending therethrough. Provided at the proximal end 702 may be preferably a locking Luer hub 706, which may be electroless nickel plated brass 360 having a Luer taper conforming to ISO 594-1:1986. Extending from the hub 706 towards the distal end 704 is an introducer needle 708 made from 20 gauge 304 full hard stainless steel thin wall hypodermic tubing with an outside diameter of about 35 to about 36 mils and an inside diameter of about 25 to about 30 mils. The Luer hub 706 and needle 708 are preferably coated with 0.1 to 0.2 mils of electrically insulative SCS Parylene C conformal coating applied to external surfaces. The electrically insulative coating preferably provides at least 100 volt minimum dielectric strength. A plurality of depth markings 710 are preferably provided along the length of the needle 708. Preferably, twelve such markings 710 are provided at a spacing of about 400 mils.

The markings 710 may be formed, e.g., by laser etching.

At the distal end 704, the needle 708 is preferably ground to a three-face lancet formation, including a point 712, a bevel portion 714, and a non-coring heel portion 716. The cuts to form the bevel 714 and heel portion 716 are all preferably provided at an angle of about 18 degrees from longitudinal parallels to the exterior surface of the needle 708.

The lead was insulated with perfluoroalkoxy and preloaded in a 20 gauge, insulated hypodermic needle introducer. During Visit 2, the patient was placed in a supine position to allow access to the femoral nerve using an anterior approach. The insertion site was cleansed using aseptic technique and local anesthesia was administered.

Prior to placing the fine-wire lead, a monopolar needle electrode 800 (24 gauge, Jari Electrode Supply, Gilroy, Calif.) was inserted below the femoral (or inguinal) crease and lateral (as opposed to medial) to the right femoral artery to within about 0.5 centimeters to about 1 centimeter of the femoral nerve under ultrasound guidance 805, preferably prior to delivering test stimulation. (See FIG. 23A.) The insertion site can be at the level of the inguinal (or femoral) crease 902 or it could be above or below it. While a preferred insertion site may be a few centimeters (1-5 cm, but typically no more than 10 cm) in either direction, good results may still be obtained if the insertion site is more than 10 cm away from the crease 902. The location of the nearby blood vessels (femoral artery 904 & vein) may also be used as landmarks, and the lead is typically inserted lateral (some distance, typically 1 mm to approximately 5 cm, but usually no more than 10 cm) to the femoral artery. The artery can be visualized on ultrasound and/or located by palpating (feeling) the pulse. Although the insertion site may be placed on either (lateral or medial) side of the femoral nerve or directly above (superficial to) the nerve (or the artery or vein), the insertion site (and the electrode) is preferably positioned lateral to the artery to minimize the risk of puncturing a blood vessel. Test stimulation (40 µs, 1 mA, 50 Hz) was delivered with a regulated-current stimulator (Maxima II, Empi, Inc., St. Paul, Minn.) to confirm that the angle of insertion 810 (about 40° from skin surface) and the length of needle under the skin (about 3.6 centimeters) was sufficient to evoke a comfortable paresthesia in a region of pain innervated by the femoral nerve. The angle of insertion may be less than or greater than the 40 degrees used in this study. Where greater lateral resolution is desired, that is, where fine lateral adjustment is desirable, lower angles of insertion may be utilized such that less lateral electrode translation occurs for a given longitudinal movement of the percutaneous lead. For instance, while a 90-degree entry angle would correspond to a 1:1 lateral translation of the electrode during lead movement (e.g. 1 mm lateral electrode translation would require 1 mm longitudinal lead movement), a 15-degree entry angle would correspond to approximately a 1:4 lateral translation (e.g. 1 mm lateral electrode translation would require 4 mm longitudinal lead movement). Steeper insertion angles may be required if a target nerve is less superficial and shallower insertion angles may be used if the target nerve is more superficial. One goal may be to have the electrode disposed in the vicinity of the femoral nerve near its trunk (cranial to the portion where it begins to fan out & separate into multiple branches). However, it may be acceptable if the electrode is disposed in another location (e.g. below the point where the nerve has begun to fan out into multiple branches), sufficient activation of the target fibers within the nerve can still be obtained even if the electrode placement is not ideal.

Another advantage to a more shallow insertion angle is that it can allow more of the lead to be located under the skin (near shallow nerves, such as the femoral nerve), increasing its ability to resist unwanted movement, dislodgement, and migration. A shallow angle of insertion capitalizes on these mechanical advantages without compromising the electrical advantages of this approach (to activate selectively the target fibers for pain relief without generating unwanted or noxious sensations (such as pain, discomfort) or unwanted muscle contraction). The shallow angle is less critical when the target nerve is located deeper under the skin, such as with the sciatic nerve. In the case of the sciatic nerve, it may be preferable to use a more perpendicular angle (even 90 degrees).

While it is preferred that the electrode and/or lead are disposed almost parallel to the femoral artery, good results can be obtained even if the electrode and/or lead are not so oriented; however, the closer to parallel (& the less perpendicular) to the artery the direction of needle insertion, there exists less risk of puncturing a blood vessel. That said, a slightly non-parallel (relative to the nerve) insertion angle could be advantageous in some circumstances because advancement/withdrawal of the electrode (along the length/direction of the introducer) will bring the electrode closer to/farther away from the nerve and/or where precise placement along the length of a nerve is desired or required.

Figure 24:
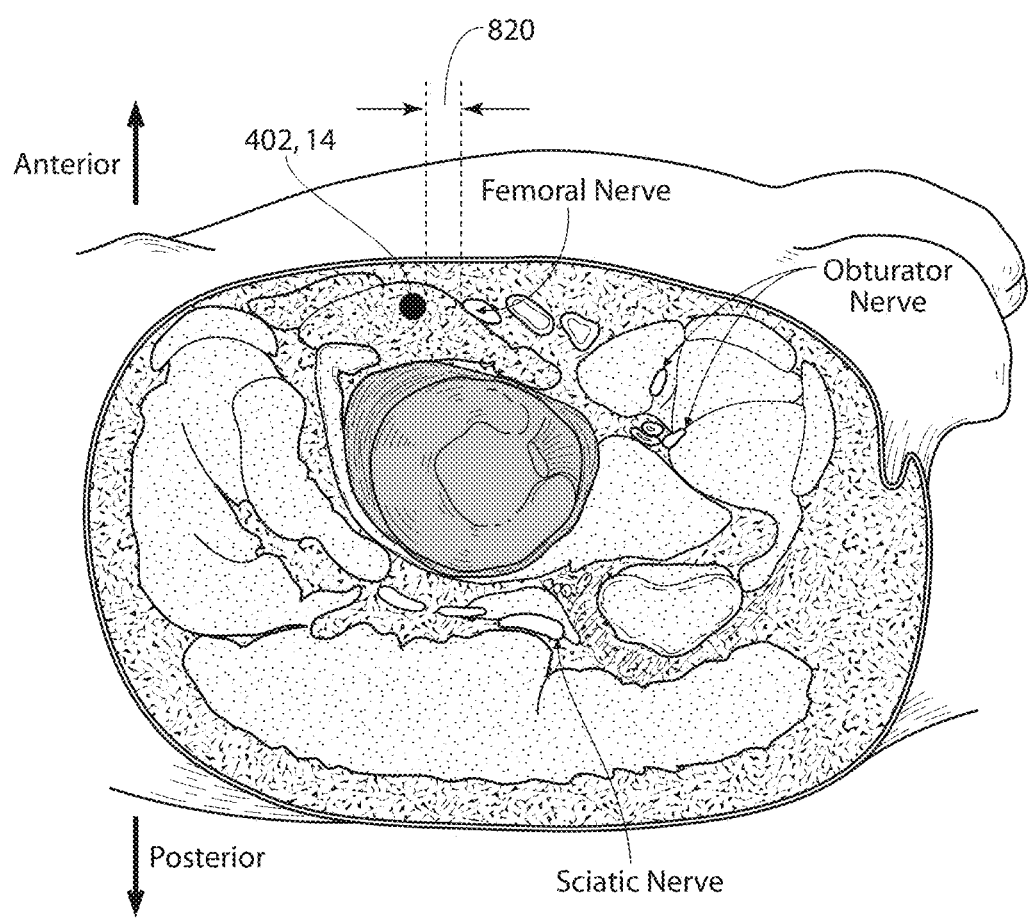
FIG. 24 is a superior cross-sectional view of a right human leg after electrode insertion.

The monopolar needle electrode was withdrawn and replaced with the fine-wire lead 400 using at least substantially the same insertion site and at least substantially the same approach except that the introducer was inserted a shorter distance than the test stimulation needle electrode was, preferably about two centimeters under the skin, placing the electrode a remote distance 820 (more than 1 centimeter away) from the nerve. (See FIGS. 23B and 24.)

Correct lead placement was confirmed by evoking a comfortable paresthesia with stimulation (50 µs, 1 mA, 50 Hz) that covered 75% of the painful area without evoking muscle contractions, qualifying the patient to proceed to the 2-week home trial. The stimulator was replaced with a regulated-voltage stimulator (Rehabilicare NT2000, Empi, Inc., St. Paul, Minn.). Stimulation pulse width was set (30 µs) and amplitude was increased to evoke the maximum comfortable paresthesia coverage (≥75%). The lead was deployed by withdrawing the introducer needle while maintaining pressure at the skin surface. A portion of the lead was coiled outside the skin to create a strain-relief loop, and the exit site was bandaged with waterproof bandages (Tegaderm by 3M, St. Paul, Minn.). The patient was instructed on the use of the stimulator and care of the bandages before progressing to the first week of the home trial.

The patient returned as planned (Visit 3) to the clinic after the first week of the home trial for bandage change, exit site inspection, and a small increase in stimulus pulse width from 30 µs to 40 µs. The patient reported improved comfort in response to the change in pulse width, and the patient progressed to the second week of the home trial.

The patient returned as planned after the second week of the home trial for lead removal (Visit 4), and again for the 1-week (Visit 5) and 4-week (Visit 6) follow-up visits after lead removal.

During lead placement (Visit 2) and the following 2-week home trial, the patient reported comfortable paresthesia coverage of greater than or equal to 50% (e.g. greater than or equal to 75%) of the region of residual limb pan (RLP), and no muscle contractions were observed in response to electrical stimulation.

Electrical stimulation of the femoral nerve reduced the RLP of the patient by 60% from baseline by the end of the 2-week home trial (see FIG. 25). The 3-day average of the BPI3 (daily worst pain) score during baseline was 7.7 prior to stimulation. This same score decreased to 3.7 after the first week of stimulation, and further decreased to 3 by the end of the second week of stimulation. Following the end of stimulation and lead removal, pain returned within 24 hours to a BPI3 score of 6 remained at approximately this level for the duration of the 4-week follow up.

The sum of the pain interference scores for the Brief Pain Inventory-Short Form (BPI-SF) decreased from 44 at baseline to 12 (71% improvement) after the first week of stimulation and to 0 (100% improvement) after the second week of stimulation (see FIG. 26). Following the end of stimulation and lead removal, the pain interference scores increased to 10 (76% change from baseline) at the 1-week follow-up visit and to 13 (69% change from baseline) at the 4-week follow-up visit.

At baseline, the sum of the Pain Disability Index (PDI) scores was 42, which decreased to 23 (45% improvement) after the first week of stimulation and further decreased to 11 (74% improvement) after the second week of stimulation. Following the end of stimulation and lead removal, the sum of the PDI scores remained at 11 at the 1-week follow-up visit and increased to 20 (53% change from baseline) at the 4-week follow-up visit.

The sum of scores on the Beck Depression Inventory (BDI-II) was 0 at baseline and at the end of the 2-week stimulation home trial. The score fluctuated by 1 point (3% of the total possible score) during the other visits.

Relative to baseline, the patient reported on the Patient Global Impression of Change (PGIC) scale that he felt "Much Improved" after the first week of stimulation and "Very Much Improved" after the second week of stimulation. Following the end of stimulation and lead removal, the patient reported feeling "Much Improved" at the 1-week follow-up visit and "Minimally Improved" at the 4-week follow-up visit.

The patient reported no phantom limb pain throughout the study with the exception of one diary entry on a single day during the baseline period. The lead was removed, intact, during Visit 4, and no adverse events were reported.

The present implementation demonstrates the first time peripheral nerve stimulation (PNS) has generated clinically significant relief of post-amputation pain using a lead placed percutaneously a remote distance away from a nerve. During the 2-week home trial of stimulation, 60% improvement was observed in the BPI3 (worst daily pain), which translated into a reduction in pain classification from severe pain (score ≥7) to minor pain (score ≤3) and correlated with similar improvements in quality of life measures.

The 2-week home trial produced complete resolution (100%) of the interference of pain on daily activities and moods as measured by the Brief Pain Inventory-Short Form (BPI-SF), and it greatly reduced (74%) the impact of pain on physical functioning and activities of daily living as measured by the Pain Disability Index (PDI). Emotional functioning was not impaired by pain at baseline, and it did not change significantly throughout the study as measured by the Beck Depression Inventory (BDI-II). The patient reported that his overall quality of life (activity limitations, symptoms, and emotions) related to his pain was "Very much improved" (the maximum score possible) by the end of the 2-week home trial relative to baseline as measured by the Patient Global Impression of Change (PLIC).

The method of PNS used in the present study is distinct from peripheral nerve field stimulation or subcutaneous stimulation in which the lead is placed in the region of pain to activate nearby nerve branches and provide pain relief to the local surrounding area. In contrast to such prior methods, in the present study, the lead was placed outside of the area of pain to activate the femoral nerve trunk and provide relief to distal areas of pain, or areas perceived to be experiencing pain that are located more distally from the central nervous system than the location of the nerve trunk activation.

The present study complements previous studies of spinal cord stimulation and peripheral nerve stimulation (PNS) that indicate electrical stimulation has the potential to provide significant relief of post-amputation pain when stimulation generates >50% paresthesia coverage of the painful region. Contrary to prior studies, in the present study, the patient reported ≥75% paresthesia coverage and >60% pain relief during the 2-week trial.

PNS offers the potential to deliver therapeutic stimulation to the nerve innervating the region of pain and limit the distribution of paresthesia to the area in which it is needed. However, PNS has not generally been used to treat post-amputation pain because conventional knowledge indicated that presently available PNS systems can be technically challenging to place in close proximity to the nerve. Traditionally, electrical stimulation of a large peripheral nerve trunk, such as the femoral nerve, has required surgical access and dissection to place a cuff-, paddle-, or plate-style lead in intimate contact with the nerve. However, recent studies have shown that cylindrical leads can be placed percutaneously in close proximity (≤2 mm) thought to be required for adequate efficacy, to the nerve under ultrasound guidance. The present invention builds on prior methodologies by demonstrating that a stimulation electrode may be placed percutaneously and remotely (>1 cm away) from a nerve and still obtain significant paresthesia coverage and pain relief.

The ability to generate significant paresthesia coverage and pain relief with a single lead, and indeed a single electrode even, inserted percutaneously and disposed remotely from a target nerve holds promise for providing relief of post-amputation pain.

Case Series

In addition to the study described above, an additional study including multiple patients has been conducted to determine, among other things, whether surgical access could be avoided by inserting a single-contact lead remote (0.5-3 cm away) from the large nerve trunks.

This further study was a case series of lower-extremity amputees with moderate to severe post-amputation pain. Residual limb pain (RLP) and phantom limb pain (PLP) were measured and assessed independently on a 0-10 scale for each individual. A fine-wire lead was inserted percutaneously under ultrasound guidance to within 0.5-3 cm of the sciatic and/or femoral nerve trunks. Correct lead placement was confirmed by evoking a comfortable paresthesia that covered >50% of the painful area without evoking muscle contractions, qualifying the individual to proceed to a 2-week home trial of stimulation, prior to which the individual was instructed on how to maintain a diary of their respective pain levels. For instance, the individual was instructed to record maximum pain levels every day, preferably at approximately the same time each day. For instance, for patients with RLP, the patient was instructed to record, on a scale of 0-10 where 0 indicates no pain and 10 indicates a level of pain as bad as the individual can imagine, his or her maximum amount of residual limb pain typically felt over the past 24 hours. For patients with PLP, the patient was instructed to record, on a scale of 0-10 where 0 indicates no pain and 10 indicates a level of pain as bad as the individual can imagine, his or her maximum amount of phantom limb pain typically felt over the past 24 hours. For patients with both RLP and PLP, they were instructed to answer each question, i.e., they were instructed to record maximum daily pain levels in their diaries for both types of pain. Additionally or alternatively, patients may be instructed to record their average level of perceived pain over the prior 24 hour period.

Results

Sufficient paresthesia coverage (average: >90%) and clinically-significant pain relief was obtained in 14 of the 16 (88%) amputees who completed the lead-placement visit. Of the 9 amputees who completed the 2-week home trial, the average improvements in the primary outcome measure (7-day mean worst pain intensity recorded in daily diaries) was approximately 59% for RLP (n=6) and 60% for PLP (n=3) at the end of treatment (EOT) relative to baseline. Many subjects continued to experience pain relief after the leads were removed and stimulation was turned off. At the last follow-up visit (4-wk post-EOT) the average improvement was approximately 66% for RLP and 52% for PLP. The results may be seen in FIGS. 27-30.

Figure 27:
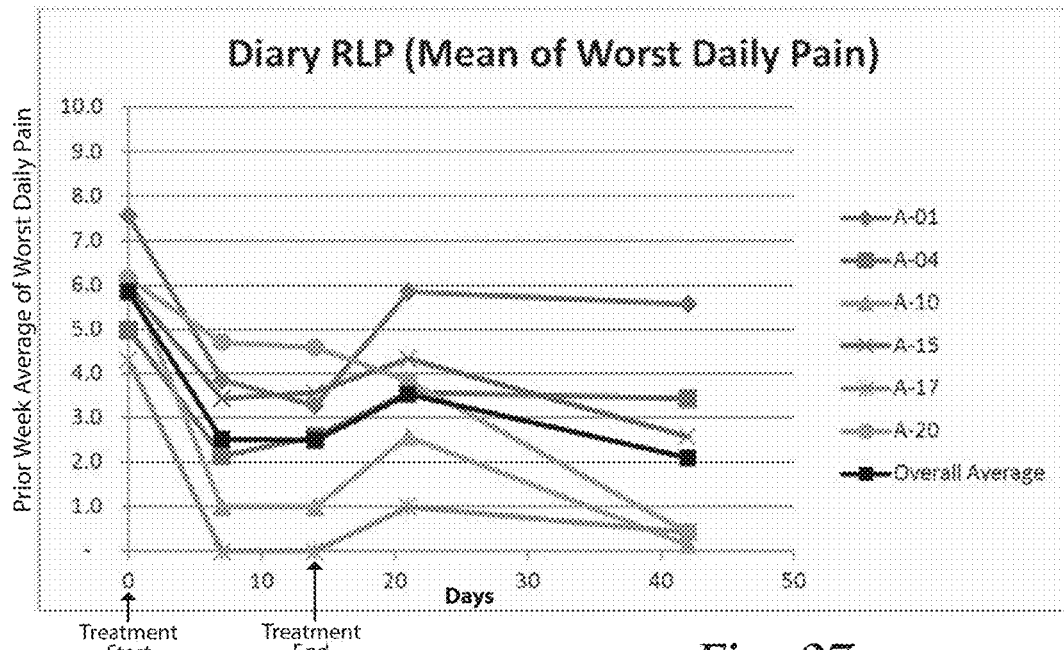
FIG. 27 is a graph showing a progression of self-reported residual limb pain intensities for six patients averaged over seven days up to forty-two days from start of a pain relief method according to the present invention.
Figure 28:
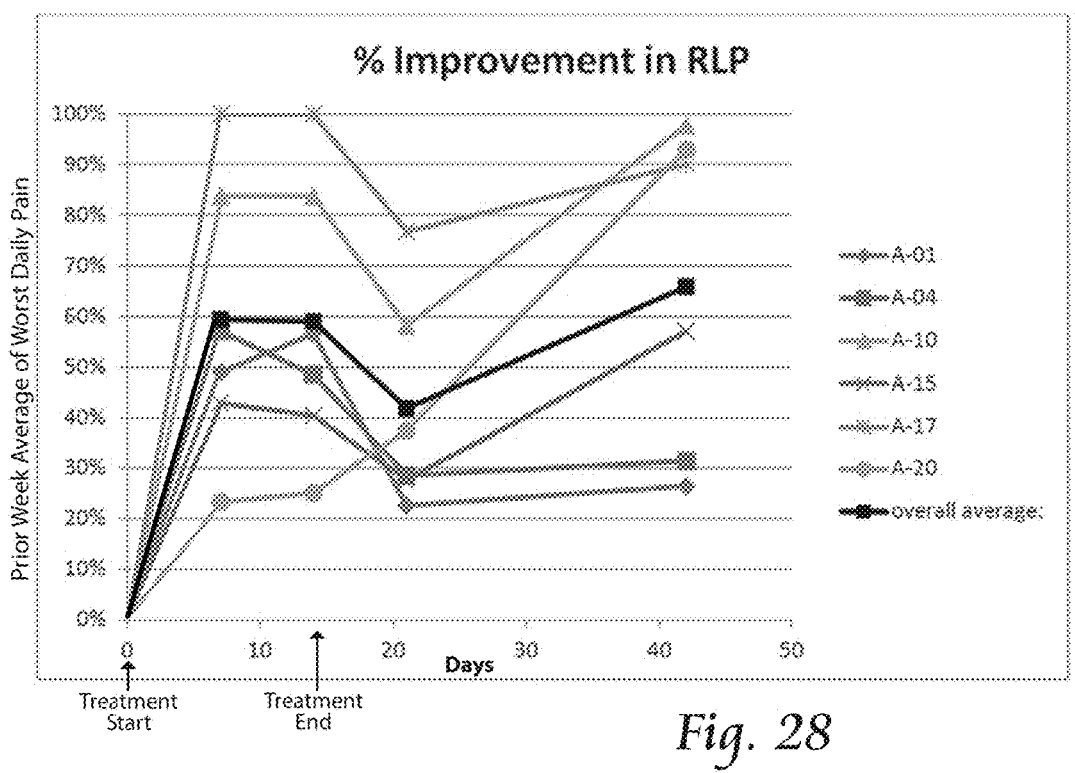
FIG. 28 is a graph showing a percent of improvement, i.e., percent reduction, of residual limb pain for the six patients whose pain intensities were diagrammed in FIG. 27.
Figure 29:
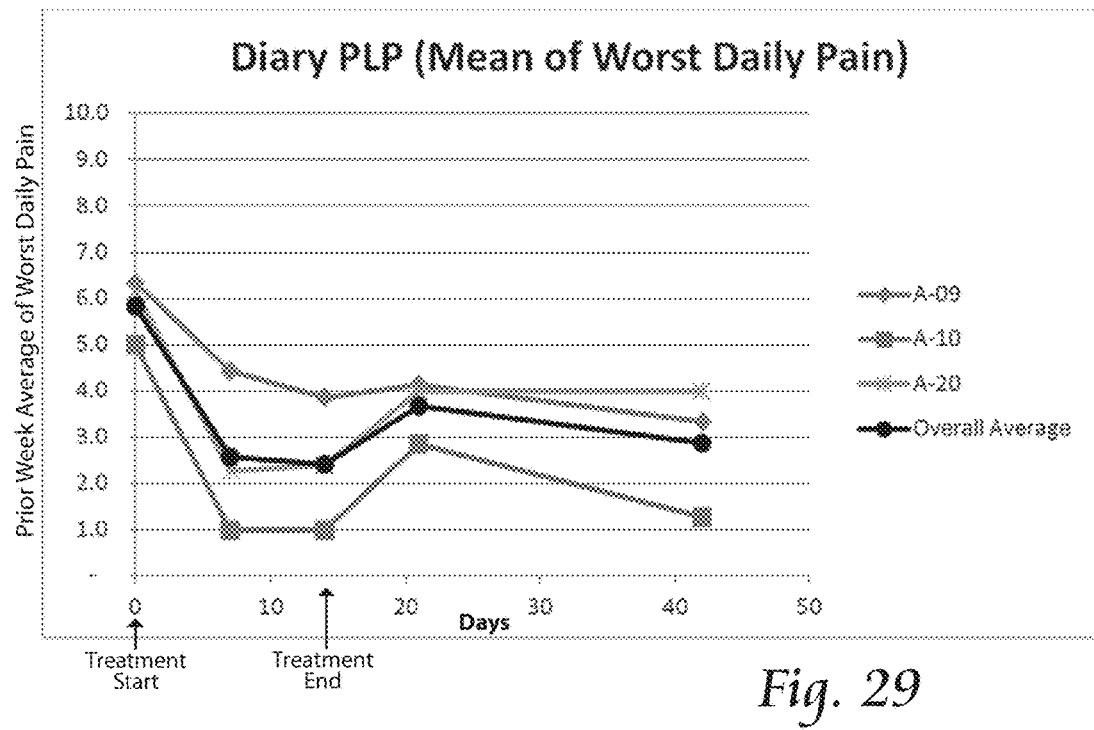
FIG. 29 is a graph showing a progression of self-reported phantom limb pain intensities for three patients (two of which were also diagrammed in FIG. 27) averaged over seven days up to forty-two days from start of a pain relief method according to the present invention.
Figure 30:
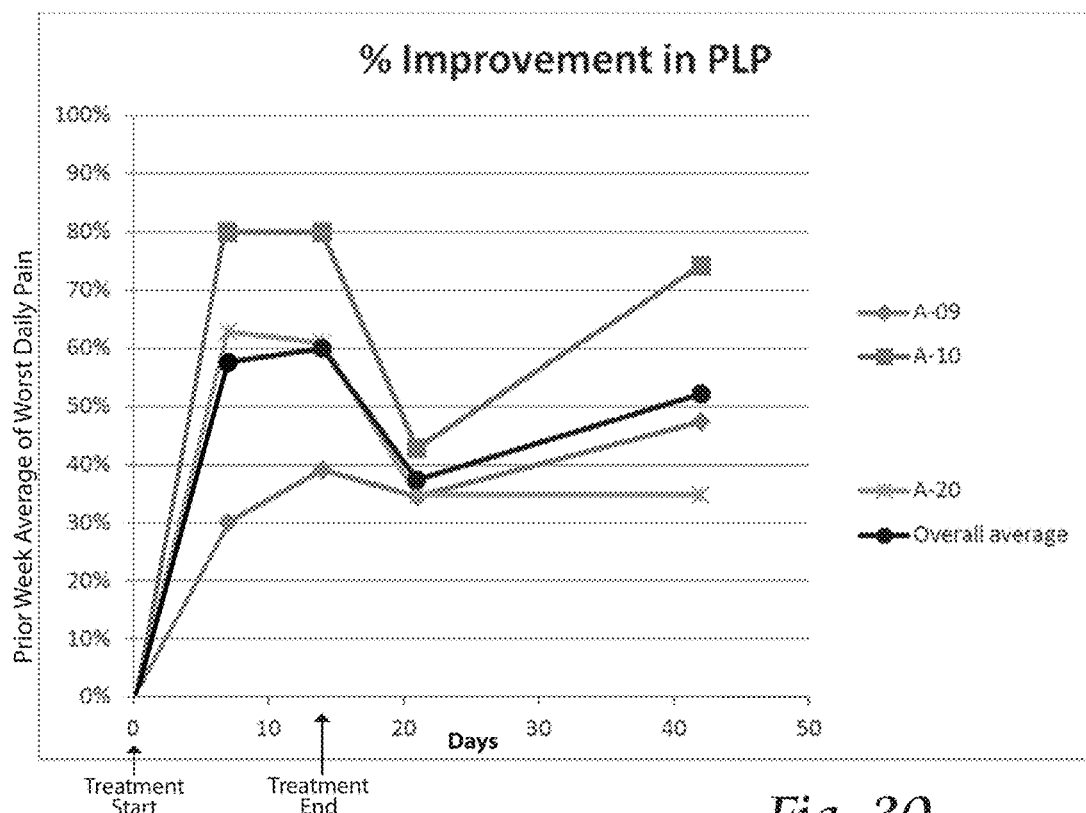
FIG. 30 is a graph showing a percent of improvement, i.e., percent reduction, of phantom limb pain for the three patients whose pain intensities were diagrammed in FIG. 29.

FIGS. 27 and 29 depict the average of the worst daily pain levels felt by the patients during the study for residual limb pain (RLP) and phantom limb pain (PLP), respectively. As can be seen in FIG. 27, there was up to a 5-point reduction in RLP during the treatment period (days 0-14) and each patient had sustained RLP relief for at least four weeks after the treatment ended. Thus, the RLP relief lasted at least twice as long as the treatment method. As can be seen in FIG. 29, there was up to a 4-point reduction in PLP during the treatment period (days 0-14) and each patient had sustained PLP relief for at least four weeks after the treatment ended. Thus, the PLP relief lasted at least twice as long as the treatment method. For the two patients that had both RLP and PLP (A-10, A-20), each had a relief of RLP by at least ninety percent at 4 weeks past end of treatment and about 35 to about 75 percent relief of PLP, as can be seen in FIGS. 28 and 30, respectively.

Improvements were also reported in secondary outcome measures: Pain Interference Scores of the Brief Pain Inventory-Short Form (EOT: 88%, 4-wk post-EOT: 63%), the Pain Disability Index (EOT: 73%, 4-wk post EOT: 67%), and the Beck Depression Inventory (EOT: 47%, 4-wk post-EOT: 61%). Improvements were also reported in the patient global impression of change (PLIC).

Case Series Conclusions

A method according to the present invention is the first to generate clinically-significant pain relief with a single-contact lead inserted percutaneously to stimulate the large nerve trunks of the sciatic and/or femoral nerves. The data also suggest the temporary percutaneous system may produce a significant carry-over effect that persists after EOT.

Figure 31:
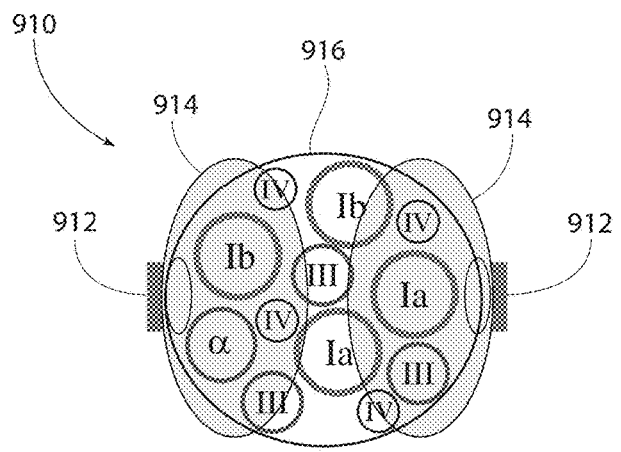
FIG. 31 is a diagrammatic representation of conventional peripheral nerve stimulation electrode placement on a nerve trunk.
Figure 32:
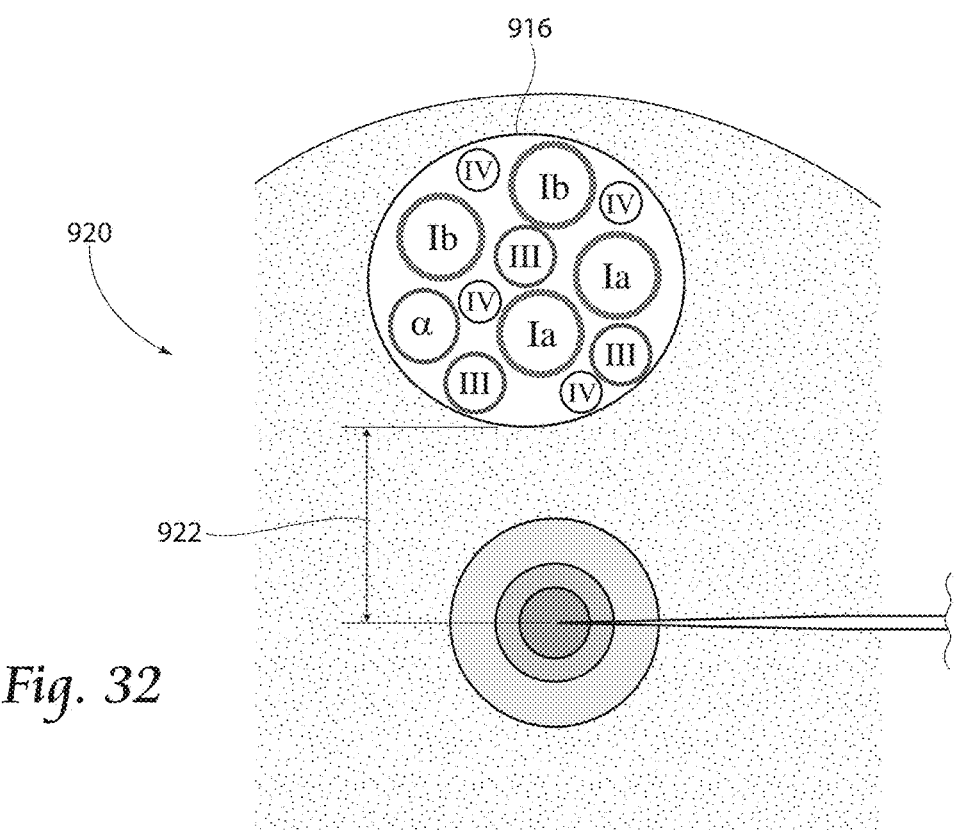
FIG. 32 is a diagrammatic representation of an electrode placement according to the present invention.

Perhaps more generally, what has been discovered is that placement of an electrode at a therapeutically effective distance away from a nerve bundle allows for selective recruitment of certain fibers within the bundle. Stated alternatively, an electrode spaced from a nerve widens the therapeutic window for providing beneficial electrical stimulation to relieve pain. Conventional placement 910 of electrodes 912 for peripheral nerve stimulation can be seen in FIG. 31. Electrical stimulation 914 is applied to a nerve bundle 916, such as a nerve trunk including multiple nerve fiber sizes and/or types, and is likely to recruit activation of both targeted fibers (such as Ia and Ib afferent fibers) and untargeted or undesirable nerve fibers (such as the other fiber types illustrated therein; i.e., III, IV, etc.). FIG. 32 depicts an electrode placement 920 according to the present invention at some therapeutically effective distance 922 away from the nerve bundle or trunk 916, which includes all of the nerve fiber types (i.e., Type Ia, Ib, III, and IV), as well as their sizes relative to one another, as illustrated in FIG. 32.

Figure 33:
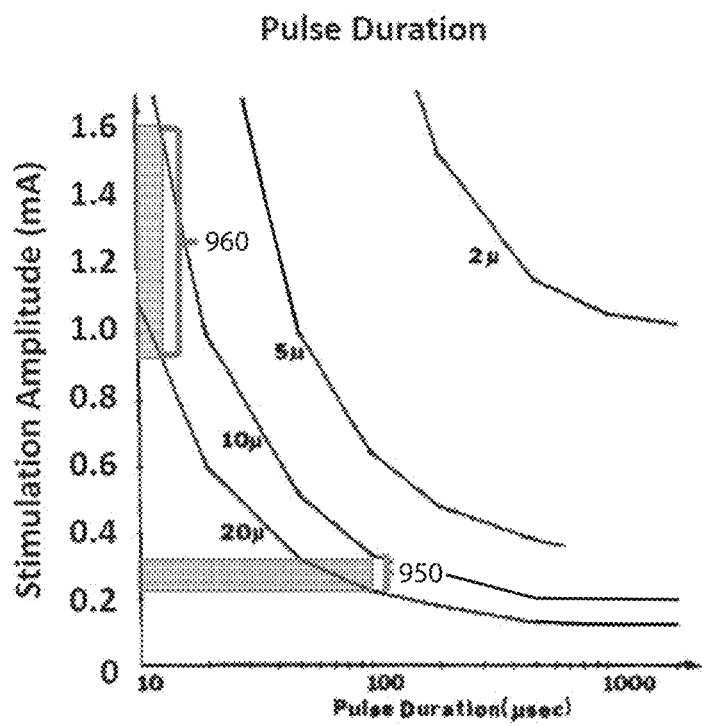
FIG. 33 is a first graph depicting a widening therapeutic window for stimulation amplitude variability of methods according to the present invention.

It is known that for activation of a neural fiber having a particular fiber diameter with an electrode placed at a predetermined distance from the fiber, the relationship between electrical stimulation amplitude and the pulse duration of such stimulation is generally inversely logarithmically proportional. However, across fiber diameters, the relationships are convergent, as can be seen in FIG. 33. Conventional peripheral nerve stimulation is usually provided at a stimulation amplitude of less than 2 mA (often about 0.2 mA to about 0.3 mA or less), so as to avoid causing pain or damage to the neural tissue, usually against which electrodes are positioned. At this stimulation amplitude level, it can be seen that conventional PNS 950 has a very narrow window in which to operate before such stimulation leads to recruitment of activation of smaller, perhaps undesirable nerve fibers. However, if nerve fibers such as afferent nerve fibers having a diameter of about 20 µm are bundled at a stimulation location with other smaller nerve fibers, such as efferent nerve fibers, methods according to the present invention expand the window of stimulation amplitude 960 so as to minimize the chances of recruiting activation of the undesirable, smaller nerve fibers. That is, using a method according to the present invention with an electrode spaced at 1 mm from a targeted nerve fiber, instead of being constrained to an amplitude of about 0.2 to about 0.3 mA (e.g. providing a window of about 0.1 mA), an amplitude in the range of about 0.9 to about 1.6 mA may be used, thus expanding the acceptable stimulation variability up to seven fold (e.g. providing a window of about 0.7 mA). While modeled numbers have been used to demonstrate the concept of a wider or less sensitive therapeutic window provided by methods according to the present invention, it is to be understood that the exact extent of an increase in the therapeutic window as described will vary depending upon patient biological factors, electrode properties, nerve fiber composition, and clinician technique.

Figure 34:
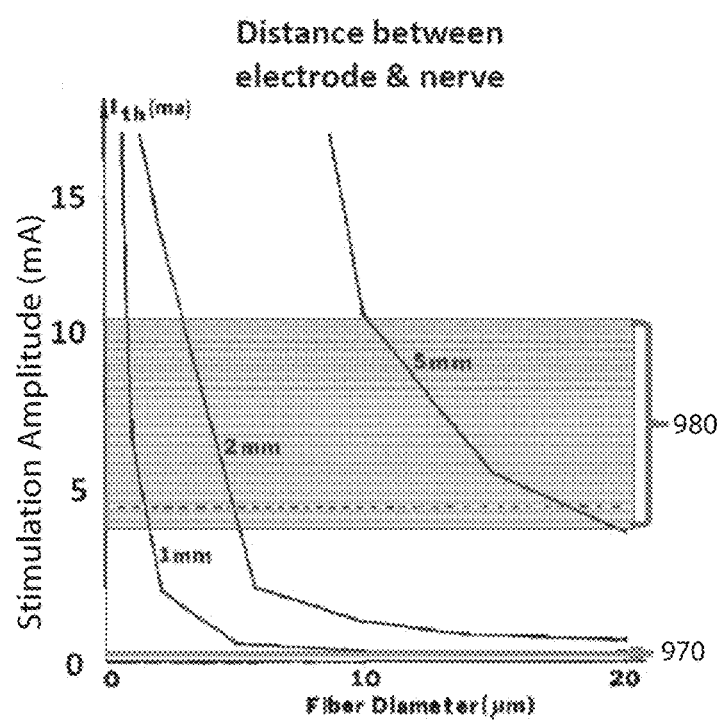
FIG. 34 is a second graph depicting a widening therapeutic window for stimulation amplitude variability of methods according to the present invention.

Likewise, for activation at a given electrode spacing from a neural fiber, the relationship between stimulation current required for activation of the fiber and the neural fiber diameter is generally inversely logarithmically proportional given a fixed pulse duration or width. However, across electrode placement spacing distances, the relationships are convergent, as can be seen in FIG. 34. As stated, conventional peripheral nerve stimulation is usually provided at a stimulation amplitude of about 0.2 mA to about 0.3 mA, so as to avoid causing pain or damage to the neural tissue, usually against which electrodes are positioned. At this stimulation amplitude level, it can be seen that conventional PNS 970 has a very narrow window in which to operate before such stimulation leads to recruitment of activation of smaller, perhaps undesirable nerve fibers. However, if nerve fibers such as afferent nerve fibers having a diameter of about 20 µm are bundled at a stimulation location with other smaller nerve fibers, such as efferent nerve fibers or smaller afferent nerve fibers, methods according to the present invention expand the window of stimulation amplitude 980 so as to minimize the chances of recruiting activation of the undesirable, smaller nerve fibers. Thus, systems and methods according to the present invention provide one or more advantages, such as less risk of neural injury to a patient and greater or wider variability in stimulation delivery.

IV. Conclusion

In "nerves of passage" stimulation, the lead is placed in tissue (e.g. muscle, adipose, connective, or other connective tissue) by which the targeted nerve passes, but stimulation actually relieves pain that is felt distal (downstream) from where the lead is placed. In "nerves of passage" stimulation, the lead can be placed in tissue (e.g. muscle, adipose, connective, or other tissue) that is conveniently located near a nerve trunk that passes by the lead on the way to the painful area. The key is that the lead is placed in tissue (e.g. muscle, adipose, connective, or other tissue) that is not the target (painful) muscle, but rather tissue (e.g. muscle, adipose, or other connective tissue) that is proximal (upstream) from the painful region because the proximal tissue (e.g. muscle, adipose, connective, or other tissue) is a more convenient and useful location to place the lead.

The advantages of nerves of passage stimulation can be recognized by anesthesiologists who are used to placing needles deeper in the tissue (e.g. muscle, adipose, connective, or other tissue) near nerves of passage Anesthesiologists are accustomed to placing needles proximal (upstream) from the areas of pain to numb the areas downstream. Anesthesiologists already use ultrasound and the electrolocation techniques that would be needed to place leads to access nerves of passage.

Nerves of passage stimulation provides stimulation-generated paresthesias (that ideally overlap with the area of pain) but does not require evoking a muscle contraction to place the lead correctly. The target regions in which pain is felt and which are targeted for generation of paresthesia are not the same region in which the lead is placed. This is an advantage because physicians (e.g. anesthesiologists, physiatrists, neurosurgeons, and/or other pain specialists) who will typically be placing the lead are accustomed to using paresthesias (sensory feedback description of from the patient) to guide lead placement and tuning of stimulation parameters.

Evoking muscle contraction with stimulation is not required for pain relief or lead location. Evoking muscle contraction with stimulation may help in relieving pain or placing the lead, but it is not required. It is an advantage that muscle contraction is not required because it allows this method to treat pains in which muscle contraction cannot be evoked (e.g. in the case of amputation pain in which the target area has been amputated and is no longer physically present or other cases of nerve damage either due to a degenerative diseases or conditions such as diabetes of impaired vascular function, in which the nerves are slowly degenerating, progressing from the periphery, or due to trauma.

In nerves of passage stimulation, the primary targeted pain area is distal to the lead, meaning that the lead is in between the major area in which pain (e.g. the worst, most troubling, or most interfering pain) is felt and the center of the body (e.g. the spinal cord)).

Imaging (e.g., ultrasound or an alternate imaging technique, e.g. fluoroscopy) may be used to improve lead placement near nerves of passage. Ultrasound may improve lead placement in the form of increasing the total speed of the procedure (shortening the procedure's duration, not necessarily increasing the speed at which the lead is advanced in the form of locating the lead in a more optimal location (to improve recruitment of the target fibers in the target nerve and minimize recruitment of non-target fibers (e.g. c fibers, other non-target sensory fibers, motor fibers, etc.) in either the target nerve and/or in non-target nerve(s); in the form of minimizing risk and/or damage to the patient during placement of the lead (by avoiding blood vessels, organs, bones, ligaments, tendons, lymphatic vessels, &/or other structures) that may be damaged. One reason that imaging may be useful is that some nerves of passage are (but do not have to be) located relatively deeply. Fluoroscopy is not required to place the lead. It may help, but it is not required. Imaging is not required.

The patient is not required to give verbal, written, or other type of feedback or indication of what they feel as the lead is being advanced towards the nerve of passage if muscle contraction or imaging is used to guide lead placement, but patient feedback during lead advancement may improve lead placement in some patients, especially in cases where (distal) muscle contraction cannot be used to confirm correct lead placement (e.g. amputees, nerve injury, nerve degeneration (e.g. due to vascular dysfunction, diabetes, etc), stimulation of a sensory nerve). The patient may indicate sensations during tuning of stimulus intensity (but this is a different step in the process and is performed after the lead has been correctly positioned). As non-limiting examples, those sensations reported by the patient may include first sensation (minimum stimulus intensity that evokes a sensation), level of comfort, maximum tolerable sensation, pain, qualities &/or descriptions of the sensations.

The region in which the patient perceives stimulation-induced sensations and/or paresthesias may be an important indicator of the potential success of the therapy (e.g. used in screening potential candidates), and the stimulation parameters (including but not limited to lead location) may be adjusted so that the region in which paresthesias are perceived overlaps with the region of pain.

As an alternative to using perception of stimulation induced sensations and/or paresthesia, the level of pain and/or change in the intensity of pain during and/or due to stimulation may be used to adjust stimulation parameters (including but not limited to lead location).

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:

1. A method of reducing a perception of pain by a human body, the method comprising the steps of:
    placing an electrode at a therapeutically effective distance spaced from a neural fiber bundle within said body, wherein said neural fiber bundle comprises at least one of a Type Ia and Ib afferent nerve fiber with at least one of Type III and Type IV nerve fibers; and
    delivering electrical stimulation from said electrode to said neural fiber bundle to reduce a perception of pain by said human, wherein said
    at least one Type Ia and Ib afferent nerve fiber of said neural fiber bundle are selectively activated while
    minimizing recruitment of activation of said at least one of Type III and Type IV nerve fiber of said neural fiber bundle due to the electrode being at the therapeutically effective distance.

2. A method according to claim 1, wherein said placing step is performed without incising a skin surface of said human body.

3. A method according to claim 1, wherein said electrode is disposed on a lead comprising at least one conductive wire.

4. A method according to claim 3, wherein during said delivering step, said conductive wire extends through a skin surface of said body.

5. A method according to claim 4, wherein said delivering step is performed for a predetermined amount of time and said conductive wire remains extended through said skin surface throughout said predetermined amount of time.

6. A method according to claim 5, wherein said predetermined amount of time comprises about two weeks to about four weeks.

7. A method according to claim 5, wherein said electrode is removed from said body after said predetermined amount of time.

8. A method according to claim 5, wherein said reduction in perception of pain continues beyond said predetermined amount of time.

9. A method according to claim 8, wherein said reduction in perception of pain continues for at least as long as said predetermined amount of time beyond said predetermined amount of time.

10. A method according to claim 9, wherein said reduction in perception of pain continues for at least twice as long as said predetermined amount of time beyond said predetermined amount of time.

11. A method according to claim 1, wherein the reduction in perception of pain comprises an at least thirty percent reduction in pain.

12. A method according to claim 1, wherein said therapeutically effective distance is greater than one centimeter.

13. A method according to claim 1, wherein said therapeutically effective distance is about 0.2 centimeters to about 3.0 centimeters.

14. A method according to claim 13, wherein said therapeutically effective distance is about five millimeters to about twenty millimeters.

15. A method according to claim 1, wherein said neural fiber bundle comprises said Type Ia and Ib afferent nerve fibers and Type III and Type IV nerve fibers.

16. A method according to claim 1, wherein said neural fiber bundle comprises said Type Ia afferent nerve fiber.

17. A method according to claim 1, wherein said neural fiber bundle comprises said Type III nerve fiber.

18. A method according claim 1, wherein said nerve fiber bundle includes an efferent nerve fiber and further comprises minimizing recruitment of activation of said efferent nerve fiber of said neural fiber bundle.

19. A method of reducing a perception of pain by a human body, the method comprising the steps of:
    placing an electrode at a therapeutically effective distance spaced from a neural fiber bundle within the body, wherein said neural fiber bundle comprises at least one of a Type Ia and Ib afferent nerve fiber plus an efferent nerve fiber; and
    delivering electrical stimulation from said electrode to said neural fiber bundle to reduce a perception of pain by said human, wherein said
    at least one of Type Ia and Ib afferent nerve fiber of said neural fiber bundle are selectively activated while
    minimizing recruitment of activation of said efferent nerve fiber of said neural fiber bundle due to the electrode being at the therapeutically effective distance.

20. A method according to claim 19, wherein selectively activating at least one of said Type Ia and Ib afferent nerve fibers includes selectively activating both of said Type Ia and Ib afferent nerve fibers.

21. A method according to claim 19, wherein minimizing recruitment of activation includes minimizing recruitment of activation of at least one of a Type III and Type IV nerve fiber of said neural fiber bundle.

22. A method according to claim 21, wherein minimizing recruitment of activation includes minimizing recruitment of activation of both said Type III and Type IV nerve fibers of said neural fiber bundle.

23. A method according to claim 19, wherein said electrode is a monopolar electrode.

24. A method according to claim 19, wherein said electrode is operably coupled with a coiled fine wire lead.

25. A method according to claim 19, wherein said electrode is a multi-contact electrode whereby only a single electrode delivers electrical stimulation.

26. A method according to claim 19, wherein said electrode includes a distal end whereby said distal end encourages in-growth of connective tissue.

27. A method of reducing a perception of pain by a human body, the method comprising the steps of:
- placing an electrode at a therapeutically effective distance spaced from a neural fiber bundle within said body, wherein said neural fiber bundle comprises more than one type of nerve fiber, wherein said therapeutically effective distance is about 0.2 centimeters to about 3.0 centimeters from said neural fiber bundle; and
- delivering electrical stimulation from said electrode to said neural fiber bundle to reduce a perception of pain by said human, wherein
- a first of said type of nerve fiber is selectively activated while
- minimizing recruitment of activation of a second of said type of nerve fiber due to the electrode being at the therapeutically effective distance, wherein said second of said type of nerve fiber includes at least one of a Type III, Type IV and efferent nerve fiber.

28. A method according to claim 27, wherein said first of said type of nerve fiber includes at least one a Type Ia and Type IB afferent nerve fiber.

29. A method according to claim 28, wherein said second of said type of nerve fiber includes said Type III and Type IV nerve fibers.

30. A method according to claim 29, wherein said first of said type of nerve fiber includes Type Ia and Type IB afferent nerve fibers.

31. A method according to claim 27, wherein said therapeutically effective distance is about five millimeters to about twenty millimeters.

32. A method according claim 27, wherein said second of said type of nerve fiber includes said efferent nerve fiber.

* * * * *